(12) United States Patent
Condon et al.

(10) Patent No.: US 7,985,735 B2
(45) Date of Patent: Jul. 26, 2011

(54) DIMERIC IAP INHIBITORS

(75) Inventors: Stephen M. Condon, Glenmoore, PA (US); Matthew G. LaPorte, Honeybrook, PA (US); Yijun Deng, Dresher, PA (US); Susan R. Rippin, Wilmington, DE (US)

(73) Assignee: Tetralogic Pharmaceuticals Corporation, Malvern, PA (US)

( * ) Notice: Subject to any disclaimer, the term of this patent is extended or adjusted under 35 U.S.C. 154(b) by 811 days.

(21) Appl. No.: 11/782,360

(22) Filed: Jul. 24, 2007

(65) Prior Publication Data

US 2008/0020986 A1 Jan. 24, 2008

Related U.S. Application Data

(60) Provisional application No. 60/820,156, filed on Jul. 24, 2006.

(51) Int. Cl.
*A61K 38/05* (2006.01)

(52) U.S. Cl. ....... 514/18.9; 514/19.3; 514/2.4; 514/20.2

(58) Field of Classification Search .................. None
See application file for complete search history.

(56) References Cited

U.S. PATENT DOCUMENTS

| | | | |
|---|---|---|---|
| 3,832,253 A | 8/1974 | DiPalma et al. | |
| 3,854,480 A | 12/1974 | Zaffaroni | |
| 4,278,793 A | 7/1981 | Durckheimer et al. | |
| 4,452,775 A | 6/1984 | Kent | |
| 4,667,014 A | 5/1987 | Nestor, Jr. et al. | |
| 4,748,034 A | 5/1988 | deRham | |
| 5,075,109 A | 12/1991 | Tice et al. | |
| 5,239,660 A | 8/1993 | Ooi | |
| 5,660,811 A | 8/1997 | Mills | |
| 5,766,572 A | 6/1998 | Hasegawa et al. | |
| 6,110,691 A | 8/2000 | Wang et al. | |
| 6,133,437 A | 10/2000 | Korneluk et al. | |
| 6,187,557 B1 | 2/2001 | Rothe et al. | |
| 6,338,835 B1 | 1/2002 | Shochat et al. | |
| 6,608,026 B1 | 8/2003 | Wang et al. | |
| 6,911,426 B2 | 6/2005 | Reed et al. | |
| 6,992,063 B2 | 1/2006 | Shi et al. | |
| 7,217,688 B2 | 5/2007 | Reed et al. | |
| 7,244,851 B2 | 7/2007 | Cohen et al. | |
| 7,309,792 B2 | 12/2007 | Harran et al. | |
| 7,517,906 B2 * | 4/2009 | Condon et al. ............ | 514/415 |
| 7,579,320 B2 | 8/2009 | Boudreault et al. | |
| 7,589,118 B2 | 9/2009 | Laurent et al. | |
| 2002/0132786 A1 | 9/2002 | Alnemri | |
| 2002/0160975 A1 | 10/2002 | Alnemri | |
| 2002/0177557 A1 | 11/2002 | Shi | |
| 2004/0054148 A1 | 3/2004 | Alnemri et al. | |
| 2005/0197403 A1 | 9/2005 | Harran et al. | |
| 2005/0234042 A1 | 10/2005 | Palermo et al. | |
| 2005/0261203 A1 | 11/2005 | Cohen et al. | |
| 2006/0014700 A1 | 1/2006 | Cohen et al. | |
| 2006/0025347 A1 | 2/2006 | Condon et al. | |
| 2006/0052311 A1 | 3/2006 | Sharma et al. | |
| 2006/0128632 A1 | 6/2006 | Sharma et al. | |
| 2006/0167066 A1 | 7/2006 | Cohen et al. | |
| 2006/0194741 A1 | 8/2006 | Condon et al. | |
| 2006/0258581 A1 | 11/2006 | Reed et al. | |
| 2006/0264379 A1 | 11/2006 | Jarvis et al. | |
| 2007/0003535 A1 | 1/2007 | Reed et al. | |
| 2007/0042428 A1 | 2/2007 | Springs et al. | |
| 2007/0093428 A1 | 4/2007 | Laurent | |
| 2007/0093429 A1 | 4/2007 | Laurent et al. | |
| 2008/0089896 A1 | 4/2008 | Wang et al. | |
| 2009/0005411 A1 | 1/2009 | Jensen et al. | |
| 2009/0104151 A1 | 4/2009 | Hanson et al. | |
| 2009/0123480 A1 | 5/2009 | Wang et al. | |
| 2009/0142334 A1 | 6/2009 | Korneluk et al. | |
| 2009/0192140 A1 | 7/2009 | Laurent et al. | |
| 2009/0221630 A1 | 9/2009 | Koehler et al. | |
| 2010/0130539 A1 | 5/2010 | Koehler | |

FOREIGN PATENT DOCUMENTS

| | | |
|---|---|---|
| WO | WO 99/15657 A2 | 4/1999 |
| WO | WO 02/16418 A1 | 2/2002 |
| WO | WO 02/26775 A2 | 4/2002 |
| WO | WO 02/30959 A2 | 4/2002 |
| WO | WO 02/096930 A2 | 12/2002 |
| WO | WO 03/018014 A2 | 3/2003 |
| WO | WO 2004/005248 A1 | 1/2004 |
| WO | WO 2004/007529 A2 | 1/2004 |
| WO | WO 2004/072105 A2 | 8/2004 |
| WO | WO 2005/069888 A2 | 8/2005 |
| WO | WO 2005/069894 A2 | 8/2005 |
| WO | WO 2005/078989 A2 | 8/2005 |
| WO | WO 2005074989 | 8/2005 |
| WO | WO 2005/084317 A2 | 9/2005 |
| WO | WO 2005/094818 A1 | 10/2005 |
| WO | WO 2005/097791 A1 | 10/2005 |
| WO | WO 2006/010118 A2 | 1/2006 |
| WO | WO 2006/014361 A1 | 2/2006 |
| WO | WO 2006/017295 A2 | 2/2006 |
| WO | WO 2006/020060 A2 | 2/2006 |
| WO | WO 2006/069063 A1 | 6/2006 |
| WO | WO 2006/091972 A2 | 8/2006 |

(Continued)

OTHER PUBLICATIONS

Kohli et al., SMAC/Diablo-dependent apoptosis induced by nonsteroidal anti-inflammatory drugs (NSAIDs) in colon cancer cells, 2004, PNAS 101(48):16897-16902.

Ripka et al., Peptidomimetic design, 1998, Curr. Op. Chem. Biol. 2:441-452.

Hruby et al., Synthesis of oligopeptide and peptidomimetic libraries, 1997, Curr. Op. in Chem. Biol. 1:114-119.

Hruby et al., Conformational and Topographical Considerations in Designing Agonist Peptidomimetics from Peptide Leads, 2000, Curr. Med. Chem. 7(9):945-970.

Nikolovska-Coleska et al., Development and optimization of a binding assay for the XIAP BIR3 domain using fluorescence polarization, 2004, Anal. Biochem. 332:261-273.

Macor et al., The Synthesis of a Conformationally Restricted Analog of the Anti-Migraine Drug Sumatriptan, 1992, Tetrahedron Lett. 33(52):8011-8014.

(Continued)

*Primary Examiner* — Christopher R. Tate
*Assistant Examiner* — Roy Teller
(74) *Attorney, Agent, or Firm* — Banner & Witcoff, Ltd.

(57) ABSTRACT

Smac mimetics that inhibit IAPs.

40 Claims, No Drawings

FOREIGN PATENT DOCUMENTS

| | | |
|---|---|---|
| WO | WO 2006/122408 A1 | 11/2006 |
| WO | WO 2006/128455 A2 | 12/2006 |
| WO | WO 2006/133147 A2 | 12/2006 |
| WO | WO 2007/021825 | 2/2007 |
| WO | WO 2007/101347 A1 | 9/2007 |
| WO | WO 2007/106192 A2 | 9/2007 |
| WO | WO 2007101347 | 9/2007 |
| WO | WO 2007/130626 A2 | 11/2007 |
| WO | WO 2007/136921 | 11/2007 |
| WO | WO 2008/016893 | 2/2008 |
| WO | WO 2008057172 | 5/2008 |
| WO | WO 2008134679 | 11/2008 |

OTHER PUBLICATIONS

Remington's Pharmaceutical Sciences, Mack Pub. Co., Easton, PA (TOC).

Craig et al., Modern Pharmacology with Clinical Applications, 6$^{th}$ Ed., Lippincott Williams & Wilkins, Philadelphia, pp. 639-656, 2004.

Hansen et al., Re-examination and further development of a precise and rapid dye method for measuring cell growth/cell kill, 1989, J. Immunol. Methods 119:203-210.

Chawla-Sarkar, Preferential Induction of Apoptosis by Interferon (IFN)-β Compared with IFN-α2: Correlation with TRAIL/Apo2L Induction in Melanoma Cell Lines, 2001, Clin. Can. Res. 7:1821-1831.

Sun et al., Structure-based Design of Potent, Conformationally Constrained Smac Mimetics, 2004, J. Am. Chem. Soc. 126:16686-16687.

Park et al., Non-peptide small molecule inhibitors of XIAP, 2004, Bioorganic & Med. Chem. Lett. 15:771-775.

Lang's Handbook of Chemistry, Dean ed., Table 7-2, 1985.

Ambrosini et al., Induction of Apoptosis and Inhibition of Cell Proliferation by Surviving Gene Targeting, 1998, J. Biol. Chem. 273(18):11177-11182.

Chai et al., Structural and biochemical basis of apoptotic activation by Smac/DIABLO, 2000, Nature 406:855-862.

Zuckerman et al., Efficient Method for the Preparation of Peptoids [Oligo(N-substituted glycines)] by Submonomer Solid-Phase Synthesis, 1992, J. Am. Chem. Soc. 114:10646-10647.

Weinstein ed., Chemistry and Biochemistry of Amino Acids, Peptides, and Proteins, 1983, Marcel Dekker, Inc., New York, New York (TOC).

Wyllie et al., Cell Death: the significance of apoptosis, 1980, Int. Rev. Cytol. 68:251-306.

Wyllie, Glucocorticoid-induced thymocyte apoptosis is associated with endogenous endonuclease activation, 1981, Nature 284:555-556.

Fulda et al., Smac agonists sensitize for Apo2L/TRAIL-or anticancer drug-induced apoptosis and induce regression of malignant glioma in vivo, 2002, Nat. Med. 8(8):808-815.

Deveraux et al., IAP family proteins-suppressors of apoptosis, 1999, Genes & Devel. 13:239-252.

Kasof et al., Livin, a Novel Inhibitor of Apoptosis Protein Family Member, 2001, J. Biol. Chem. 276(5):3238-3246.

Vucic et al., ML-IAP, a novel inhibitor of apoptosis that is preferentially expressed in human melanomas, 2000, Curr. Biol. 10:1359-1366.

Ashhab et al., two splicing variants of a new inhibitor of apoptosis gene with different biological properties and tissue distribution pattern, 2001, FEBS Lett. 495:56-60.

Du et al., Smac, a mitochondrial Protein that Promotes Cytochrome c-Dependent Caspase Activation by Eliminating IAP Inhibitiion, 2000, Cell 102:33-42.

Verhagen et al., Identification of DIABLO, a Mammalian Protein that Promotes Apoptosis by Binding to and Antagonizing IAP Proteins, 2000, Cell 102:43-53.

Hay, Understanding IAP function and regulation: a view from Drosophila, 2000, Cell Death and Diff. 7:1045-1056.

Chan et al., Fmoc Solid Phase Peptide Synthesis: A Practical Approach, 2000, Oxford University Press (TOC).

Boxrud et al., Streptokinase Binds to Human Plasmin with High Affinity, Perturbs the Plasmin Active Site, and Induces Expression of a Substrate Recognition Exosite for Plasminogen, 2000, J. Biol. Chem. 275(19):14579-14589.

Owenius et al., Properties of Spin and Fluorescent Labels at a Receptor-Ligand Interface, 1999, Biophys. J. 77:2237-2250.

Hiratsuka, ATP-induced Opposite Changes in the Local Environments around Cys$^{697}$ (SH2) and Cys$^{707}$ (SH1) of the Myosin Motor Domain Revealed by the Prodan Fluorescence, 1999, J. Biol. Chem. 274(41):29156-29163.

Wu et al., Structural basis of IAP recognition by Smac/DIABLO, 2000, Nature 408:1008-1012.

Brunger, X-PLOR, a System for Crystallography and NMR, Yale University Press, New Haven, CT, 1991.

Chen et al., Grim, a novel cell death gene in drospohila, 1996, Genes & Devel. 10:1773-1782.

Goyal et al., Induction of apoptosis by drosophila reaper, hid and grim through inhibition of IAP function, 2000, EMBO J. 19(4):589-597.

Jones et al., Improved methods for building protein models in electron density maps and thelocation of errors in these models, 1991, Acta Crystallogr. A47:110-119.

Kraulis, Molscript: a program to produce both detailed and schematic plots of protein structures, 1991, J. Appl. Crystallogr. 24:946-950.

Lisi et al., Diverse Domains of THREAD/DIAPI are Required to Inhibit Apoptosis Induced by REAPER and HID in Drosophila, 1999, Genetics Soc. Am. 154:669-678.

Liu, Structural basis for binding of Smac/DIABLO to the XIAP BIR3 domain, Dec. 2000, Nature, pp. 1004-1008.

McCarthy et al., Apoptosis induced by drosophila reaper and grim in a human system, 1999, J. Biol. Chem. 273(37):24009-24015.

Morgan et al., Approaches to the Discovery of Non-Peptide Ligands for Peptide Receptors and Peptidases. 1989, Ann. Rep. Med. Chem. 243-252.

Navaza, AmoRe: an Automated Package for Molecular Replacement, 1994, Acta Cryst. A50:157-163.

Nicholls et al., Protein folding and association: insights from the interfacial and thermodynamic properties of hydrocarbons, 1991, Proteins: Struct. Funct. & Genet. 11:281-296.

Srinivasula et al., A conserved XIAP-interaction motif in caspase-9 and Smac/DIABLO regulates caspase activity and apoptosis, 2001, Nature 410:112-116.

Sun et al., NMR Structure and Mutagenesis of the Third Bir Domain of the Inhibitor of Apoptosis Protein XIAP, 2000, J. Biol. Chem. 275(43):33777-33781.

Terwilliger et al., The CCP4 suite: Programs for protein crystallography, 1994, Acta Crystallogr. D50:760-763.

Terwilliger et al., Correlated Phasing of Multiple Isomorphous Replacement Data, 1996, Acta Crystallogr. D52:749-757.

Vucic et al., Inhibition of Reaper-induced apoptosis by interaction with inhibitor of apoptosis proteins (IAPS), 1997, Proc. Natl. Acad. Sci. USA 94:10183-10188.

Stellar, Mechanisms and Genes of Cellular Suicide, 1995, Science 267:1445-1449.

Jacobson et al., Programmed Cell Death in Animal Development, 1997, Cell 88:347-354.

Hengartner, Programmed cell death in invertebrates, 1996, Curr. Opin. Genet. Dev. 6:34-38.

Horvitz, Genetic Control of Programmed Cell Death in the Nematode Caenorhabditis elegans, 1999, Can. Res. 59:1701s-1706s.

Miller, An exegesis of IAPs: salvation and surprises from BIR motifs, 1999, Cell Biol. 9:323-328.

Deveraux et al., Cleavage of human inhibitor of apoptosis protein XIAP results in fragments with distinct specificities for caspases, 1999, EMBO J. 18(19):5242-5251.

Takahashi et al., A Single BIR Domain XIAP Sufficient for Inhibiting Caspases, 1998, J. Biol. Chem. 273(14):7787-7790.

Sun et al., NMR structure and mutagenesis of the inhibitor-of-apoptosis protein XIAP, 1999, Nature 40:818-822.

Shi, Survivin structure: crystal unclear, 2000, Nat. Str. Biol. 7(8):620-623.

Verdecia et al., Structure of the human anti-apoptotic protein surviving reveals a dimeric arrangement, 2000, Nat. Struc. Biol. 7(7):602-608.

Chantalat et al., Crystal Structure of Human Survivin Reveals a Bow Tie-Shaped Dimer with Two Unusual α-Helical Extensions, 2000, Mol. Cell. 6:183-189.

Wang et al., The Drosphila Caspase Inhibitor DIAP1 is Essential for Cell Survival and Is Negatively Regulated by HID, 1999, Cell 98:453-463.

Hirel et al., Extent of N-terminal methionine excision from *Escherichia coli* proteins is governed by the side-chain length of the penultimate amino acid, 1989, Proc. Natl. Acad. Sci. USA 86:8247-8251.

Freidinger et al., Synthesis of 9pflourenylmethyloxycarbobyl-protected n-alkyl amino acids by reductin of oxazolidinones, 1983, J. Org. Chem. 48:77-81.

Srinivasula et al., Molecular Determinants of the Caspase-promoting activity of Smac/DIABLO and its role in the death receptor pathway, 2000, J. Biol. Chem. 275(46):36152-36157.

Wu et al., Structural Analysis of a Functional DIAP1 Fragment Bound to Grim and Hid Peptides, 2001, Mol. Cell 8:95-104.

Oost et al., Discovery of Potent Antagonists of the Antiapoptotic Protein XIAP for the Treatment of Cancer, 2004, J. Med. Chem. 47:4417-4426.

Gennaro, Remington's Pharmaceutical Sciences, Mack Publ. Co., Easton, PA (TOC).

Vucic et al., Engineering ML-IAP to produce an extraordinarily potent caspase 9 inhibitor: implications for Smac-dependent anti-apoptotic activity of ML-IAP, 2005, Biochem. J. 385(1):11-20.

International Search Report and Written Opinion of ISA for PCT/US2007/074225.

International Preliminary Report on Patentability issued by the International Bureau of WIPO on Jan. 27, 2009.

Kohli et al., SMAC/Diablo-dependent apoptosis induced by nonsteroidal anti-inflammatory drugs (NSAIDs) in colon cancer cells, 2004, PNAS 101(48):16897-16902.

Ripka et al., Peptidomimetic design, 1998, Curr. Op. Chem. Biol. 2:441-452.

Hruby et al., Synthesis of oligopeptide and peptidomimetic libraries, 1997, Curr. Op. in Chem. Biol. 1:114-119.

Hruby et al., Conformational and Topographical Considerations in Designing Agonist Peptidomimetics from Peptide Leads, 2000, Curr. Med. Chem. 7(9):945-970.

Nikolovska-Coleska et al., Development and optimization of a binding assay for the XIAP BIR3 domain using fluorescence polarization, 2004, Anal. Biochem. 332:261-273.

Macor et al., The Synthesis of a Conformationally Restricted Analog of the Anti-Migraine Drug Sumatriptan, 1992, Tetrahedron Lett. 33(52):8011-8014.

Remington's Pharmaceutical Sciences, Mack Pub. Co., Easton, PA (TOC), 2005.

Craig et al., Modern Pharmacology with Clinical Applications, $6^{th}$ Ed., Lippincott Williams & Wilkins, Philadelphia, pp. 639-656, 2004.

Bockbrader et al., "A small molecule Smac-mimic compound induces apoptosis and sensitizes TRAIL—and etoposide-induced apoptosis in brease cancer cells," Oncogene, 2005, Vo. 24, No. 49, pp. 7381-7388.

Fotin-Mleczek et al., "Cationic cell-penetrating peptides interfere with TNF signalling by induction of TNF receptor internalization," Journal of Cell Science, 2005, vol. 118, No. 15, pp. 3339-3351.

Li et al., "A Small Molecule Smac Mimic Potentiates TRAIL—and TNF-α-Mediated Cell Death," Science, 2004, vol. 305, No. 5689, pp. 1471-1474.

* cited by examiner

DIMERIC IAP INHIBITORS

This application claims priority to and benefit of U.S. Provisional Application No. 60/820,156 entitled "Dimeric IAP Inhibitors" filed on Jul. 24, 2006; the entire contents of which is hereby incorporated by reference in its entirety.

Apoptosis (programmed cell death) plays a central role in the development and homeostasis of all multi-cellular organisms. Apoptosis can be initiated within a cell from an external factor such as a chemokine (an extrinsic pathway) or via an intracellular event such a DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPs (inhibitors of apoptosis proteins).

The IAP family of proteins suppresses apoptosis by preventing the activation of procaspases and inhibiting the enzymatic activity of mature caspases. Several distinct mammalian IAPs including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo. Smac/DIABLO-derived peptides have also been demonstrated to sensitize a number of different tumor cell lines to apoptosis induced by a variety of pro-apoptotic drugs.

In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids: the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis. Whereas cytochrome c induces multimerization of Apaf-1 to activate procaspase-9 and -3, Smac eliminates the inhibitory effect of multiple IAPs, Smac interacts with essentially all IAPs that have been examined to date including XIAP, c-IAP1, c-IAP2, ML-IAP, and survivin. Thus, Smac appears to be a master regulator of apoptosis in mammals.

It has been shown that Smac promotes not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

Current trends in cancer drug design focus on selective targeting to activate the apoptotic signaling pathways within tumors while sparing normal cells. The tumor specific properties of specific chemotherapeutic agents, such as TRAIL have been reported. The tumor necrosis factor-related apoptosis-inducing ligand (TRAIL) is one of several members of the tumor necrosis factor (TNF) superfamily that induce apoptosis through the engagement of death receptors. TRAIL interacts with an unusually complex receptor system, which in humans comprises two death receptors and three decoy receptors, TRAIL has been used as an anti-cancer agent alone and in combination with other agents including ionizing radiation. TRAIL can initiate apoptosis in cells that overexpress the survival factors Bcl-2 and Bcl-XL, and may represent a treatment strategy for tumors that have acquired resistance to chemotherapeutic drugs. TRAIL binds its cognate receptors and activates the caspase cascade utilizing adapter molecules such as TRADD. TRAIL signaling can be inhibited by overexpression of cIAP-1 or 2, indicating an important role for these proteins in the signaling pathway. Currently, five TRAIL receptors have been identified. Two receptors TRAIL-R1 (DR4) and TRAIL-R (DR5) mediate apoptotic signaling, and three non-functional receptors, DcR1, DcR2, and osteoprotegerin (OPG) may act as decoy receptors. Agents that increase expression of DR4 and DR5 may exhibit synergistic anti-tumor activity when combined with TRAIL.

The basic biology of how IAP antagonists work suggests that they may complement or synergize other chemotherapeutic/anti-neoplastic agents and/or radiation. Chemotherapeutic/anti-neoplastic agents and radiation would be expected to induce apoptosis as a result of DNA damage and/or the disruption of cellular metabolism.

Inhibition of the ability of a cancer cell to replicate and/or repair DNA damage will enhance nuclear DNA fragmentation and thus will promote the cell to enter the apoptotic pathway. Topoisomerases, a class of enzymes that reduce supercoiling in DNA by breaking and rejoining one or both strands of the DNA molecule, are vital to cellular processes, such as DNA replication and repair. Inhibition of this class of enzymes impairs the cells ability to replicate as well as to repair damaged DNA and activates the intrinsic apoptotic pathway.

The main pathways leading from topoisomerase-mediated DNA damage to cell death involve activation of caspases in the cytoplasm by proapoptotic molecules released from mitochondria, such as Smac. The engagement of these apoptotic effector pathways is tightly controlled by upstream regulatory pathways that respond to DNA lesions-induced by topoisomerase inhibitors in cells undergoing apoptosis. Initiation of cellular responses to DNA lesions-induced by topoisomerase inhibitors is ensured by the protein kinases which bind to DNA breaks. These kinases (non-limiting examples of which include Akt, JNK and P38) commonly called "DNA sensors" mediate DNA repair, cell cycle arrest and/or apoptosis by phosphorylating a large number of substrates, including several downstream kinases.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of cross-bridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDs appear to induce apoptosis via the release of Smac from the mitochondria (PNAS, Nov. 30, 2004, vol 101:16897-16902). Therefore, the use of NSAIDs in combination with Smac mimetics would be expected to increase the activity each drug over the activity of either drug independently.

Many naturally occurring compounds isolated from bacterial, plant, and animals can display potent and selective biological activity in humans including anticancer and antineoplastic activities. In fact, many natural products, or semi-synthetic derivatives thereof, which possess anticancer activity, are already commonly used as therapeutic agents; these include paclitaxel, etoposide, vincristine, and camptothecin amongst others. Additionally, there are many other classes of natural products such as the indolocarbazoles and epothilones that are undergoing clinical evaluation as anticancer agents. A reoccurring structural motif in many natural products is the attachment of one or more sugar residues onto an aglycone core structure. In some instances, the sugar portion of the natural product is critical for making discrete protein-ligand interactions at its site of action (i.e., pharmacodynamics) and removal of the sugar residue results in significant reductions in biological activity. In other cases, the sugar moiety or moieties are important for modulating the physical and pharmacokinetic properties of the molecule. Rebeccamycin and staurosporine are representative of the sugar-linked indolocarbazole family of anticancer natural products with demonstrated anti-kinase and anti-topoisomerase activity.

SUMMARY OF THE INVENTION

The present invention provides IAP antagonists that are peptidomimetic compounds that mimic the tertiary binding structure and activity of the N-terminal four amino acids of mature Smac to IAPs. The invention also provides methods of using these mimetics to modulate apoptosis and further for therapeutic purposes.

In one aspect of the present invention, an IAP antagonist that is a homodimeric or heterodimeric compound having the general formula (I), depicted below, and pharmaceutically acceptable salts thereof. Solvates including hydrates, stereoisomers including enantiomers, crystalline forms including polymorphs, and the like are encompassed within the scope of the invention.

Another embodiment of the present invention is the therapeutic combination of compounds of the present invention with TRAIL or other chemical or biological agents which bind to and activate the TRAIL receptor(s). TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, Smac mimetics increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The Smac mimetics disclosed herein bind to IAPs and inhibit their interaction with caspases, therein potentiating TRAIL-induced apoptosis.

Another embodiment of the present invention provides Smac mimetics which act synergistically with topoisomerase inhibitors to potentiate their apoptotic inducing effect. Topoisomerase inhibitors inhibit DNA replication and repair, thereby promoting apoptosis and have been used as chemotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors.

Topoisomerase inhibitors of both the Type I class (camptothecin, topotecan, SN-38 (irinotecan active metabolite) and the Type II class (etoposide) show potent synergy with the Smac mimetics of the invention in a multi-resistant glioblastoma cell line (T98G), breast cancer line (MDA-MB-231), and ovarian cancer line (OVCAR-3) among others. Further examples of topoisomerase inhibiting agents that may be used include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent may be a platinum containing compound. In one embodiment of the invention the platinum containing compound is cisplatin. Cisplatin can synergize with a Smac peptidomimetic and potentiate the inhibition of an IAP, such as but not limited to XIAP, cIAP-1, c-IAP-2, ML-IAP, etc. In another embodiment a platinum containing compound is carboplatin. Carboplatin can synergize with a Smac peptidomimetic and potentiate the inhibition of an IAP, including, but not limited to, XIAP, cIAP-1, c-IAP-2, ML-IAP, etc. In another embodiment a platinum containing compound is oxaliplatin. The oxaliplatin can synergize with a Smac peptidomimetic and potentiate the inhibition of an IAP, including, but not limited to, XIAP, cIAP-1, c-IAP-2, ML-IAP, etc.

In another embodiment of the invention, the chemotherapeutic/anti-neoplastic agent that synergizes with a compound according to the present invention is a taxane. Taxanes are anti-mitotic, mitotic inhibitors or microtubule polymerization agents. Taxanes include but are not limited to, docetaxel and paclitaxel.

Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. The unique mechanism of action of taxane is in contrast to other microtubule poisons, such as Vinca alkaloids, colchicine, and cryptophycines, which inhibit tubulin polymerization. Microtubules are highly dynamic cellular polymers made of alpha-beta-tubulin and associated proteins that play key roles during mitosis by participating in the organization and function of the spindle, assuring the integrity of the segregated DNA. Therefore, they represent an effective target for cancer therapy.

In another embodiment, any agent that activates the intrinsic apoptotic pathway and/or causes the release of Smac or cytochrome c from the mitochondria has the potential to act synergistically with a Smac mimetic.

A combination of a Smac peptidomimetic and a chemotherapeutic/anti neoplastic agent and/or radiation therapy of any type that activates the intrinsic pathway may provide a more effective approach to destroying tumor cells. Smac peptidomimetics interact with IAP's, such as XIAP, cIAP-1, cIAP-2, NIL-IAP, etc., and block the TAP mediated inhibition of apoptosis while chemotherapeutics/anti neoplastic agents and/or radiation therapy kills actively dividing cells by activating the intrinsic apoptotic pathway leading to apoptosis and cell death. As is described in more detail below, embodiments of the invention provide combinations of a Smac pepidomimetic and a chemotherapeutic/anti-neoplastic agent and/or radiation which provide a synergistic action against unwanted cell proliferation. This synergistic action between a Smac peptidomimetic and a chemotherapeutic/anti-neoplastic agent and/or radiation therapy can improve the efficiency of the chemotherapeutic/anti-neoplastic agent and/or radiation therapy. This will allow for an increase in the effectiveness of current chemotherapeutic/anti-neoplastic agents or radiation treatment allowing the dose of the chemotherapeutic/anti-neoplastic agent to be lowered, therein providing both a more effective dosing schedule as well as a more tolerable dose of chemotherapeutic/anti-neoplastic agent and/or radiation therapy.

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DEFINITIONS

"Alkyl" and "alkylene" mean a branched or unbranched, saturated or unsaturated (i.e. alkenyl, alkenylene, alkynyl, alkynylene) non-cyclic aliphatic hydrocarbon group, having up to 12 carbon atoms unless otherwise specified. (However, if alkenylene is specified but alkynylene is not, then alkynylene is excluded. E.g., "alkylene or alkenylene" excludes alkynylene.) When used as part of another term, for example, "alkylamino", the alkyl portion may be a saturated hydrocarbon chain, however also includes unsaturated hydrocarbon carbon chains such as "alkenylamino" and "alkynylamino". Examples of particular alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl", "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, optionally substituted alkyl groups may contain one, two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding-ethyl, -propyl, -butyl, -pentyl, -hexyl groups, etc. Particular substituted alkyls are substituted methyl groups. Examples of the substituted methyl group include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, bromomethyl and iodomethyl.

"Cycloalkyl" means a saturated or unsaturated cyclic aliphatic hydrocarbon group, having up to 12 carbon atoms unless otherwise specified and includes cyclic and polycyclic, including fused cycloalkyl.

"Amino" denotes primary (i.e., —$NH_2$), secondary (i.e., —NRH) and tertiary (i.e., —NRR) amines.

Particular secondary and tertiary amines are alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and disopropylamine.

"Aryl" when used alone or as part of another term means a carbocyclic aromatic group whether or not fused having the number of carbon atoms designated or if no number is designated, up to 14 carbon atoms. Particular aryl groups include phenyl, naphthyl, biphenyl, phenanthrenyl, naphthacenyl, and the like (see e.g., Lang's handbook of Chemistry (Dean, J. A., ed) 13th ed. Table 7-2 [1985]). In a particular embodiment an aryl group is phenyl. Optionally substituted phenyl or optionally substituted aryl denotes a phenyl group or aryl group that may be substituted with one, two, three, four or five substituents chosen, unless otherwise specified, from halogen (F, Cl, Br, I), hydroxy, protected hydroxy, cyano, nitro, alkyl (such as $C_1$-$C_6$ alkyl), alkoxy (such as $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di (halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono-or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group, for example, 4-cyanophenyl; a mono-or di (lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di (alkoxy) phenyl group, for example, 3,4-dimethoxyphenyl, 3-methoxy-4-benzyloxyphenyl, 3-methoxy-4-(1-chloromethyl) benzyloxy-phenyl, 3-ethoxyphenyl, 4-(isopropoxy)phenyl, 4-(t-butoxy) phenyl, 3-ethoxy-4-methoxyphenyl and the like; 3- or 4-trifluoromethylphenyl; a mono-or dicarboxyphenyl or (protected carboxy)phenyl group such 4-carboxyphenyl; a mono-or di(hydroxymethyl) phenyl or (protected hydroxymethyl)phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl)phenyl; or a mono-or di(N-(methylsulfonylamino)) phenyl such as 3-(N-methylsulfonylamino))phenyl; Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-enzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with the substituents specified herein, for example with 1, 2 or 3 substituents, in the same manner as substituted alkyl groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, non-aromatic ring systems having the number of atoms designated, generally from 5 to about 14 ring atoms, where the ring atoms are carbon and at least one heteroatom (nitrogen, sulfur or oxygen). In a particular embodiment the group incorporates 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles include morpholinyl(morpholino), pyrrolidinyl, oxiranyl, oxetanyl, tetrahydrofuranyl, 2,3-dihydrofuranyl, 2H-pyranyl, tetrahydropyranyl, aziridinyl, azetidinyl, 1-methyl-2-pyrrolyl, piperazinyl and piperidinyl. For the avoidance of doubt, "heterocycloalkyl includes heterocycloalkyl alkyl.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur (Lang's Handbook of Chemistry, supra). Included in the definition are any bicyclic groups where any of the above heteroaryl rings are fused to a benzene ring. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b] pyridazinyl and purinyl, as well as benzo-fused derivatives, for example benzoxazolyl, benzofuryl, benzothiazolyl, benzothiadiazolyl, benzotriazolyl, benzoimidazolyl and indolyl. Particularly "heteroaryls" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1,4-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5- dihydro-5-oxo-2-methyl-as-triazin-3-yl, 2,5-dihydro-5-oxo-2,6-dimethyl-as-triazin-3-yl, tetrazolo[1,5-b] pyridazin-6-yl and 8-aminotetrazolo[1, 5-b]-pyridazin-6-yl. An alternative group of "heteroaryl" includes: 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H- tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

For the avoidance of doubt, aryl includes fused aryl which includes, for example, naphthyl, indenyl; cycloalkyl includes fused cycloalkyl which includes, for example, tetrahydronaphthyl and indanyl; heteroaryl includes fused heteroaryl which includes, for example, indoyl, benzofuranyl, benzothienyl; fused heterocyclo includes fused heterocycloalkyl which includes, for example, indolinyl, isoindolinyl, tetrahydroquinolinyl, tetrahydroisoquinolinyl.

"Optionally substituted" means that a H atom can be, but is not necessarily, replaced by one or more different atoms. One of skill in the art will readily know, or can readily ascertain, what atoms or moieties can be substituted for a hydrogen atom or atoms in a given position. Typical optional substituents are any one or more of hydroxy, alkyl, lower alkyl, alkoxy, lower alkoxy, cycloalkyl, heterocycloalkyl, aryl, heteroaryl, halogen, pseudohalogen, haloalkyl, pseudohaloalkyl, carbonyl, carboxyl, mercapto, amino, nitro, and thiocarbonyl, but other moieties can also be optional substituents. So, for example, optionally substituted nitrogen can mean an amide, sulfonamide, urea, carbamate, alkylamines, dialkylamines, arylamines, etc; optionally substituted alkyl includes methyl, ethyl, propyl, isopropyl, t-butyl, etc.; optionally substituted aryl includes phenyl, benzyl, tolyl, pyridine, naphthyl, imidazole, etc. Reference to a group as "optionally substituted" encompasses that group when it is substituted as described above or, alternatively, when it is unsubstituted. When "optionally substituted" is used in front of or at the end of a listing of chemical groups, all such groups are optionally substituted (unless otherwise indicated by context.)

A "Linker" is a bond or linking group whereby two chemical moieties are directly covalently linked one to the other or are indirectly linked via a chemical moiety that covalently links the two chemical moieties, in either case, to form a homo- or heterodimer. A Linker (L), therefore, is a single, double, or triple covalent bond or is a contiguous chain, branched or unbranched, substituted or unsubstituted, of 1 to about 100 atoms, typically 1 to about 20 atoms and typically up to about 500 MW, e.g., alkyl, alkylene, alkylyne, alkyloxyalkyl, alkylarylalkyl, or optionally-substituted alkyl, alkylene, alkylyne, alkyloxyalkyl, alkylarylalkyl chain of 1 to 12 atoms. Illustrative Linkers are described, e.g., in US 20050197403 as well as in U.S. patent application Ser. No. 11/363,387 filed Feb. 27, 2006, both of which are incorporated herein by reference as though fully set forth.

"Pseudohalogens" are binary inorganic compounds of the general form XY, where X is a cyanide, cyanate, thiocyanate etc. group and Y is any of X, or a true halogen. Not all combinations are known to be stable. Examples include cyanogen, $(CN)_2$ and iodine cyanide, ICN. These anions behave as halogens and the presence of the internal double bonds or triple bonds do not appear to affect their chemical behavior.

"Inhibitor" or "antagonists" means a compound which reduces or prevents the binding of IAP proteins to caspase proteins or which reduces or prevents the inhibition of apoptosis by an IAP protein, or which binds to an IAP BIR domain in a manner similar to the amino terminal portion of Smac, thereby freeing Smac to inhibit the action of an IAP.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

DETAILED DESCRIPTION OF THE PREFERRED EMBODIMENTS

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the terms "pharmaceutically acceptable", "physiologically tolerable" and grammatical variations thereof, as they refer to compositions, carriers, diluents and reagents, are used interchangeably and represent that the materials can be administered to a human being.

As used herein "subject" or "patient" refers to an animal or mammal including, but not limited to, human, dog, cat, horse, cow, pig, sheep, goat, chicken, monkey, rabbit, rat, mouse, etc.

As used herein, the term "therapeutic" means an agent utilized to treat, combat, ameliorate, prevent or improve an unwanted condition or disease of a patient. Embodiments of the present invention are directed to promote apoptosis, and thus cell death.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively promote apoptosis, preferably by eliminating an IAP inhibition of apoptosis, more preferably by inhibiting an IAP binding to a caspase.

It has been demonstrated in accordance with the present invention that the IAP-binding compounds of the present invention are capable of potentiating apoptosis of cells. The following compounds are illustrative of dimers of the present invention.

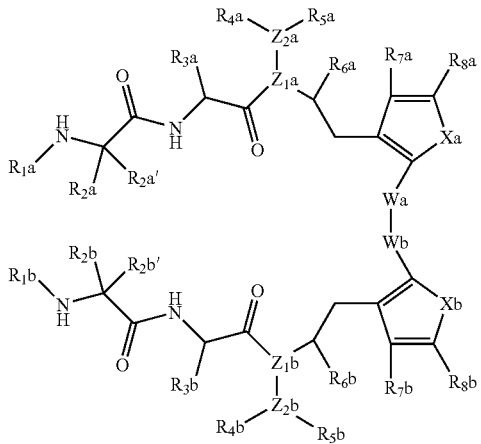

wherein $Z_1a$, $Z_2a$ $Z_1b$, and $Z_2b$ are independently CH or N;

$R_1a$ and $R_1b$ are independently H or optionally substituted hydroxyl, alkyl, cycloalkyl, heterocycloalkyl, aryl, arylalkyl, heteroaryl, or heteroarylalkyl; and when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_2a$, $R_2a'$, $R_2b$ and $R_2b'$ are independently H or optionally substituted alkyl, cycloalkyl, or heterocycloalkyl; or when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_3a$, $R_3b$, $R_4a$ and $R_4b$ are independently H or optionally substituted alkyl, cycloalkyl, heterocycloalkyl, aryl, arylalkyl, heteroaryl, or heteroarylalkyl; or, $R_4a$ and $R_3a$, or $R_4b$ and $R_3b$, or both, are carbon atoms linked by an optionally-substituted alkylene or alkenylene group of 1 to 8 carbon atoms where one to three carbon atoms can be replaced by N, O, S(O)n, or C=O;

$R_5a$, $R_6a$, $R_5b$, and $R_6b$ are independently H or optionally substituted hydroxyl, alkyl, cycloalkyl, heterocycloalkyl, aryl, arylalkyl, heteroaryl, or heteroarylalkyl; or $R_5a$ and $R_6a$ or $R_5b$ and $R_6b$, or both, are carbon atoms linked by an optionally-substituted alkylene or alkenylene group of 1 to 8 carbon atoms where one to three carbon atoms can be replaced by N, O, S(O)$_n$, or C=O;

$R_7a$, $R_7b$, $R_8a$, $R_8b$ are independently H or optionally substituted hydroxyl, alkyl, cycloalkyl, heterocycloalkyl, aryl, arylalkyl, heteroaryl, or heteroarylalkyl; or $R_7a$ and $R_8a$, or $R_7b$ and $R_8b$, or both, can be linked by an optionally-substituted alkylene or alkenylene group of 3 to 8 carbon atoms where one to three carbon atoms can be replaced by N, O, S(O)$_n$, or C=O to form an aromatic or non-aromatic ring, n can be the same or different in each usage and is 0, 1, or 2;

Xa is —O—, —N(La—$R_{10}$a)-, —S—, optionally-substituted —C(La—$R_{10}$a)=CH—, —C(O)—O—, —C(O)—N(La—$R_{10}$a)-, —N=C(La—$R_{10}$a)-;

Xb is —O—, —N(Lb-$R_{10}$b)-, —S—, optionally-substituted —C(Lb-$R_{10}$b)=CH—, —C(O)—O—, —C(O)—N(Lb-$R_{10}$b)-, —N=C(Lb-$R_{10}$b)-;

La and Lb are independently a covalent bond or $C_1$-$C_4$ alkylene;

Wa, Wb, $R_{10}$a, and $R_{10}$b are defined in paragraphs (a) through (e), which follow:

(a) when Wa and Wb together are a Linker, then Xa or Xb are independently —O—, —S—, or —C(O)—O—; $R_{10}$a and $R_{10}$b, respectively, are absent; or (b) when Wa and Wb together are a Linker; Xa is —N(La—$R_{10}$a)-, —C(La—$R_{10}$a)=CH—, —N=C(La—$R_{10}$a)-, or —C(O)—N(La—$R_{10}$a)-; Xb is —N(Lb-$R_{10}$b)-, —C(Lb-$R_{10}$b)=CH—, —N=C(Lb-$R_{10}$b)-, or —C(O)—N(Lb-$R_{10}$b)-; $R_{10}$a and $R_{10}$b are independently H or optionally substituted hydroxyl, alkyl, cycloalkyl, heterocycloalkyl, aryl, or heteroaryl; or (c) when Wa and Wb together are a Linker; Xa is —N(La—$R_{10}$a)-, —C(La—$R_{10}$a)=CH—, —N=C(La—$R_{10}$a)-, or —C(O)—N(La—$R_{10}$a)-; Xb is —N(Lb-$R_{10}$b)-, —C(Lb-$R_{10}$b)=CH—, —N=C(Lb-$R_{10}$b)-, or —C(O)—N(Lb-$R_{10}$b)-; $R_{10}$a and $R_{10}$b together are a Linker; or (d) when Wa and Wb are not covalently bound, Wa and Wb, are independently H, Cl, Br, F, CN, COOH, or optionally substituted hydroxyl, alkyl, cycloalkyl, heterocycloalkyl, aryl, or heteroaryl, Xa is —N(La—$R_{10}$a)-, —C(La—$R_{10}$a)=CH—, —N=C(La—$R_{10}$a)-, or —C(O)—N(La—$R_{10}$a)-; Xb is —N(Lb-$R_{10}$b)-, —C(Lb-$R_{10}$b)=CH—, —N=C(Lb-$R_{10}$b)-, or —C(O)—N(Lb-$R_{10b}$)-; $R_{10}$a and $R_{10}$b together are a Linker; or (e) when Wa and Wb are not covalently bound, Wa is H, C$_l$, Br, F, CN, COOH, or optionally substituted hydroxyl, alkyl, cycloalkyl, heterocycloalkyl, aryl, or heteroaryl; Xa is —N(La—$R_{10}$a)-, —C(La—$R_{10}$a)=CH—, —N=C(La—$R_{10}$a)-, or —C(O)—N(La—$R_{10}$a)-; Xb is —O—, —N(Lb-$R_{10}$b)-, —S—, —C(Lb-$R_{10}$b)=CH—, —C(O)—O—, —N=C(Lb-$R_{10}$b)-, —C(O)N(Lb-$R_{10}$b)-; and Lb is a covalent bond, and $R_{10}$b is absent or is H or optionally substituted hydroxyl, alkyl, cycloalkyl, heterocycloalkyl, aryl, or heteroaryl; and Wb and $R_{10}$a together are a Linker.

Illustrative compounds have formula (II):

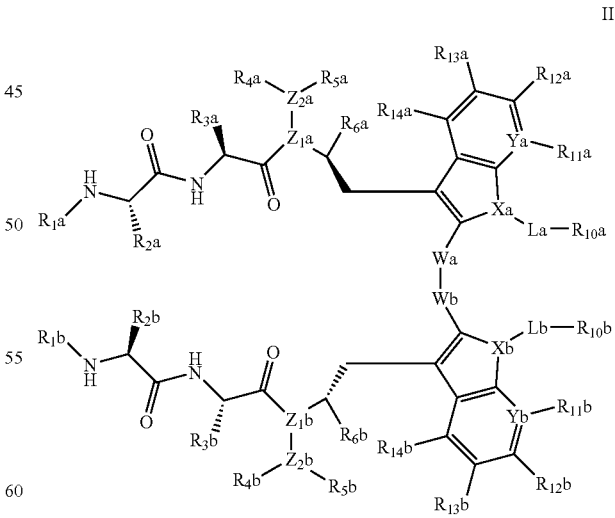

wherein

Xa is —N—, —C=C($R_{16}$a)-, —N=C— or —C(O)N—;

Xb is —N—, —C=C($R_{16}$b)-, —N=C— or —C(O)N—;

La and Lb are independently a covalent bond or $C_1$-$C_4$ alkylene;

Ya is —C—, —N—, or —N⁺—; such that,

When Ya is —C— then $R_{10}a$, $R_{11}a$, $R_{12}a$, $R_{13}a$, $R_{14}a$, $R_{15}a$, and $R_{16}a$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xa is —N— or —C(O)—N—, $L_1$-$R_{10}a$ is bound to the —N— atom; and, when Xa is —C=C($R_{16}a$)- or —N=C—, $L_1$-$R_{10}a$ is bound to the —C= atom; and When Ya is —N— or —N⁺—, then $R_{11}a$ is absent or —O—, and $R_{10}a$, $R_{11}a$, $R_{13}a$, $R_{14}a$, $R_{15}a$, and $R_{16}a$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, -$L_1$-$R_{10}$ is bound to the —N— atom; and, when X is —C=C($R_{16}a$)- or —N=C—, -$L_1$-$R_{10}a$ is bound to the —C= atom;

Yb is —C—, —N—, or —N⁺—; such that,

When Yb is —C— then $R_{10}b$, $R_{11}b$, $R_{12}b$, $R_{13}b$, $R_{14}b$, $R_{15}b$, and $R_{16}b$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xb is —N— or —C(O)—N—, -$L_1$-$R_{10}b$ is bound to the —N— atom; and, when Xb is —C=C($R_{16}b$)- or —N=C—, -L1-$R_{10b}$ is bound to the —C= atom; and When Yb is —N— or —N⁺—, then $R_{11}b$ is absent or —O—, and $R_{10}b$, $R_{12}b$, $R_{13}b$, $R_{14}b$, $R_{15}b$, and $R_{16}b$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xb is —N— or —C(O)—N—, -L1-$R_{10}b$ is bound to the —N— atom; and, when Xb is —C=C($R_{16}b$)- or —N=C—, -$L_1$-$R_{10}b$ is bound to the —C= atom Illustrative compounds have formula (IV):

In illustrative compounds of formula I, II, or IV, when $Z_1a$ is N and $Z_2a$ is CH, and $Z_1b$ is N and $Z_2b$ is CH, then at least one of the following is true:

(i) $R_5a$ and $R_5a$ are not both carbon atoms linked by a single covalent bond;

(ii) $R_5a$ and $R_6a$ are both carbon atoms linked by a single covalent bond and $R_5a$ is disubstituted;

(iii) $R_5a$ and $R_6a$ are both carbon atoms linked by a single covalent bond and $R_6a$ is mono- or disubstituted;

(iv) $R_5a$ and $R_6a$ are both carbon atoms linked by a single covalent bond and $R_3a$ and $R_4a$ are both carbon atoms linked by a covalent bond or by an optionally-substituted alkylene or alkenylene group of 1 to 8 carbon atoms where one to three carbon atoms can be replaced by N, O, $S(O)_n$, or C=O.

(v) $R_5a$ and $R_6a$ are both carbon atoms linked by a single covalent bond and neither $R_2a$ nor $R_2a'$ are H.

In illustrative embodiments of compounds of formula I, II, or IV, one or any two or more of the following limitations may apply:

$R_3a$, $R_4a$, $R_3b$, and $R_4b$ are independently selected from H, methyl, ethyl, isopropyl, isobutyl, sec-butyl, tert-butyl, cycloalkyl, heterocycloalkyl, aryl, arylalkyl, heteroaryl, or heteroarylalkyl, optionally-substituted with hydroxyl, mercapto, sulfonyl, alkylsulfonyl, halogen, pseudohalogen, amino, carboxyl, alkyl, haloalky, pseudohaloalkyl, alkoxy, or alkylthio; or $R_3a$, $R_4a$, $R_3b$, and $R_4b$ are independently optionally substituted lower alkyl or $C_3$-$C_8$ cycloalkyl wherein the optional substituents are hydroxy or lower alkoxy;

$R_2a$ and $R_2b$ are independently selected from —H, methyl, fluoromethyl, difluoromethyl, ethyl, fluoroethyl, hydroxyethyl, and cycloalkyl;

$R_1a$ and $R_1b$ are independently selected from H, methyl, allyl, propargyl, ethyl, hydroxyethyl, cycloalkyl, or cycloalkylmethyl;

Wa and Wb together are a covalent bond or optionally substituted alkylene, cycloalkyl, or aryl, of 2 to 20 carbon atoms where one or more carbon atoms can be replaced with N, O, or $S(O)_n$; and Xa and Xb are independently —O—, —S—, or —C(O)—O—; or Wa and Wb are not covalently bound, and Wa and Wb are inde-

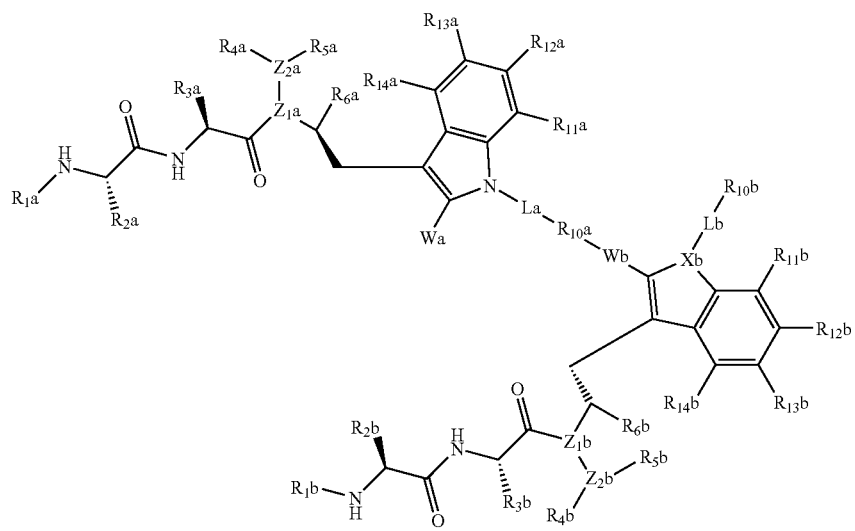

IV pendently H, Cl, Br, F, CN, COOH, or optionally substituted hydroxyl, alkyl, cycloalkyl, heterocycloalkyl, aryl, arylalkyl, heteroaryl, or heteroarylalkyl; or Wb and $R_{10}a$ (or Wa and $R_{10}b$) together are a covalent bond or optionally substituted alkylene, cycloalkyl or aryl, of 2 to 20 carbon atoms where one or more carbon atoms can be replaced with N, O, or $S(O)_n$;

La and Lb are each a covalent bond;

$R_{10}a$ and $R_{10}b$ are independently H or optionally substituted hydroxyl, alkyl, cycloalkyl, heterocycloalkyl, aryl, or heteroaryl; or $R_{10}a$ and $R_{10}b$ together are an optionally-substituted alkylene, cycloalkyl, or aryl of 2 to 20 carbon atoms where one or more carbon atoms can be replaced with N, O, or $S(O)_n$;

$Z_1a$ and $Z_1b$ are both N and $Z_2a$ and $Z_2b$ are both C;

$R_{10}a$ and $R_{10}b$ are not heterocycloalkyl or heteroaryl,

In illustrative embodiments, Wa, Wb, $R_{10}a$, and $R_{10}b$ are defined in paragraphs (a) through (e), which follow, (a) when Wa and Wb together are -L- and form, for example, a covalent bond, alkylene, cycloalkyl, heterocycloalkyl, aryl, or heteroaryl, or an optionally-substituted alkylene, chain of 2 to 20 carbon atoms where one or more carbon atoms can be replaced with N, O, or $S(O)_n$; and Xa and Xb are respectively —O—, —S—, or —C(O)—O—; $R_{10}a$ and $R_{10}b$ are absent;

(b) when Wa and Wb together are -L- and form, for example, a covalent bond, alkylene, cycloalkyl, heterocycloalkyl, aryl, arylalkylene, arylalkylalkylene, heteroaryl, heteroarylalkylene, or an optionally-substituted alkylene, chain of 2 to 20 carbon atoms where one or more carbon atoms can be replaced with N, O, or $S(O)_n$; and Xa and Xb are respectively —N(La—$R_{10}a$)-, optionally-substituted —C(La—$R_{10}a$)=CH—, or —(O)—N(La—$R_{10}a$)-, or —N(Lb-$R_{10}b$)-, optionally-substituted —C(Lb-$R_{10}b$)=CH—, or —C(O)—N(Lb-$R_{10}b$)-; $R_{10}a$ and $R_{10}b$ are independently H, hydroxyl, hydroxyalkyl, alkyl, alkoxy, cycloalkyl, heterocycloalkyl, aryl, or heteroaryl, in each case optionally-substituted; or (c) when Wa and Wb together are -L- and form, for example, a covalent bond, alkylene, cycloalkyl, heterocycloalkyl, aryl, or heteroaryl, or an optionally-substituted alkylene chain of 2 to 20 carbon atoms where one or more carbon atoms can be replaced with N, O, or $S(O)_n$; and Xa and Xb are respectively —N(La$R_{10}a$)-, optionally-substituted —C(La—$R_{10}a$)=CH—, or —(O)—N(La—$R_{10}a$)-, or —N(Lb-$R_{10}b$)-, optionally-substituted —C(Lb-$R_{10}b$)=CH—, or —C(O)—N(Lb-$R_{10}b$)-; $R_{10}a$ and $R_{10}b$ together are -L- and form, for example, an optionally-substituted alkylene, or alkyloxyalkylene chain of 2 to 20 carbon atoms where one or more carbon atoms can be replaced with N, O, or $S(O)_n$; or (d) when Wa and Wb are not covalently bound, Wa and Wb are independently H, Cl, Br, F, CN, $CO_2H$, alkyl, cycloalkyl, heterocycloalkyl, aryl, heteroaryl, or optionally-substituted alkyl, cycloalkyl, heterocycloalkyl, aryl, or heteroaryl; Xa and Xb are respectively —N(La—$R_{10}a$)-, optionally-substituted —C(La—$R_{10}a$)=CH—, or —C(O)—N(La—$R_{10}a$)-, or —N(Lb-$R_{10}b$)-, optionally-substituted —C(Lb-$R_{10}b$)=CH—, or —C(O)—N(Lb-$R_{10}b$)-; and $R_{10}a$ and $R_{10}b$ together are -L- and form, for example, an optionally-substituted alkylene, or alkyloxyalkylene chain of 2 to 20 carbon atoms where one or more carbon atoms can be replaced with N, O, or $S(O)_n$; or (e) when Wa and Wb are not covalently bound, Wa is H, Cl, Br, F, CN, $CO_2H$, alkyl, cycloalkyl, heterocycloalkyl, aryl, heteroaryl, or optionally-substituted alkyl, cycloalkyl, heterocycloalkyl, aryl, or heteroaryl; Xa is —N(La—$R_{10}a$)-, optionally-substituted —C(La—$R_{10}a$)=CH—, or C(O)—N(La—$R_{10}a$)-; Xb is —O—, —N(Lb-$R_{10}b$)-, —S—, optionally-substituted —C(Lb-$R_{10}b$)=CH—, —C(O)—O—, —C(O)—N(Lb-$R_{10}b$)-; and $R_{10}b$ is absent or H, hydroxyl, hydroxyalkyl, alkyl, alkoxy, alkoxyalkyl, cycloalkyl, heterocycloalkyl, aryl, or heteroaryl, in each case optionally-substituted; and Wb and $R_{10}a$ together are -L- and form, for example, a bond, alkylene, cycloalkyl, aryl, or heteroaryl, or an optionally-substituted alkylene, chain of 2 to 20 carbon atoms where one or more carbon atoms can be replaced with N, O, or $S(O)_n$.

Illustrative compounds are compounds having the formula

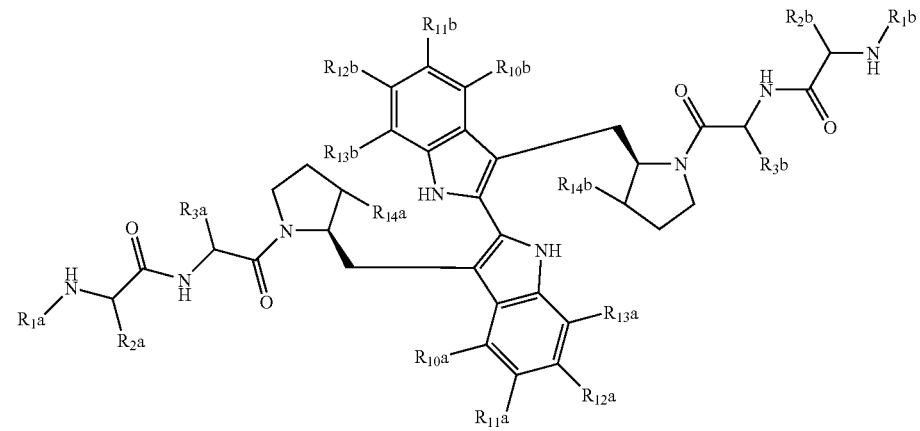

wherein $R_1a$, $R_1b$, $R_2a$, $R_2b$, $R_3a$, and $R_3b$ are independently lower alkyl, lower alkoxy, lower alkanol, or $C_3$-$C_6$ cycloalkyl; $R_{14}a$ and $R_{14}b$ are independently —OH, lower alkoxy or lower alkyl; $R_{11}a$, $R_{11}b$, $R_{12}a$, $R_{12}b$, $R_{13}a$, $R_{13}b$ are independently —H or halogen.

Illustrative compounds are compounds having the formula:

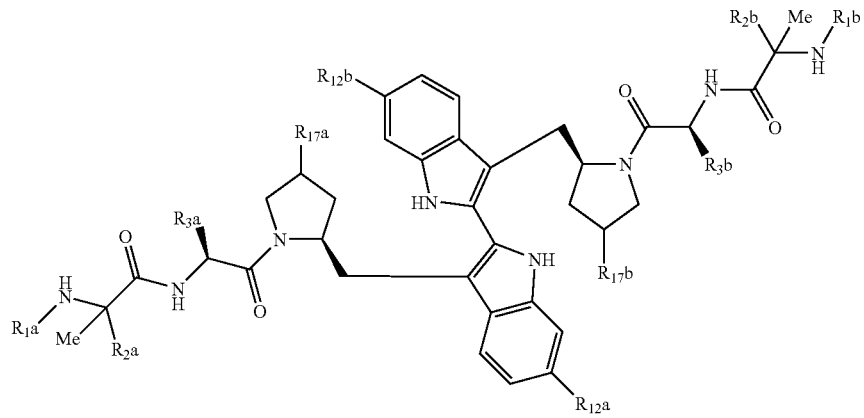

20 wherein $R_1a$, $R_1b$, $R_2a$, $R_2b$, $R_3a$, and $R_3b$ are independently lower alkyl, lower alkoxy, lower alkanol, or $C_3$-$C_6$ cycloalkyl; $R_{17}a$ and $R_{17}b$ are independently —OH, lower alkoxy or lower alkyl; $R_{12}a$ and $R_{12}b$ are independently —H or halogen.

Illustrative Chemistry Schemes:

Abbreviations used in the following preparations, which are illustrative of synthesis of compounds of the invention generally, are: Cbz: Benzyloxycarbonyl; Boc: tert-butyloxycarbonyl; THF: tetrahydrofuran; DCM: dichloromethane; DDQ:2,3-dichloro-5,6-dicyano-1,4-benzoquinone; NMP: N-methylpyrrolidinone; DMF: dimethylformamide; TFA: trifluoracetic acid; HOAc or AcOH: acetic acid; Hex: hexanes; HPLC: high performance liquid chromatography, TLC: thin layer chromatography; EtOAc: ethyl acetate; DIPEA: diisopropylethylamine; TEA: triethylamine; HATU: 2-(7-Aza-1H-benzotriazole-1-yl)-1,3,3-tetramethyluronium hexafluorophosphate.

Compounds of formula 8 can be prepared using methods outlined in Angiolini et al. (Eur. J. Org. Chem., 2000, 2571-2581), Harris et al. (Org. Lett. 2003, 5, 1847-1850), O'Neil et al. (Bioorg. Med. Chem. Lent. 2005, 15, 5434-5438), Grossmith et al. (Synlett 1999, 10, 1660-1662), and in U.S. Patent Application Publication Number 20060025347 and U.S. patent application Ser. No. 11/363,387 filed Feb. 27, 2006, all of which are incorporated by reference herein as though fully set forth, and described in Schemes I and II.

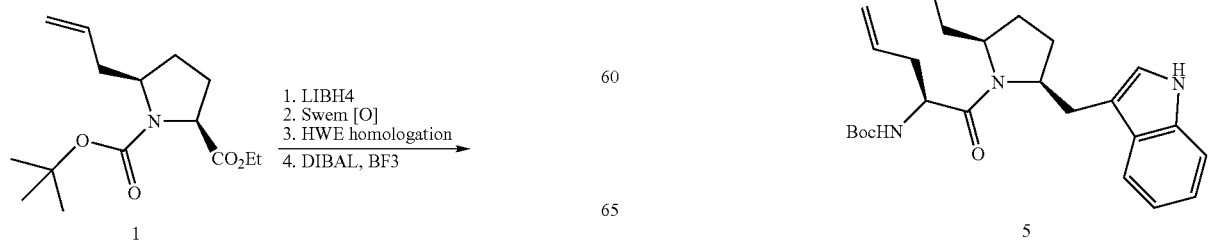

Scheme II

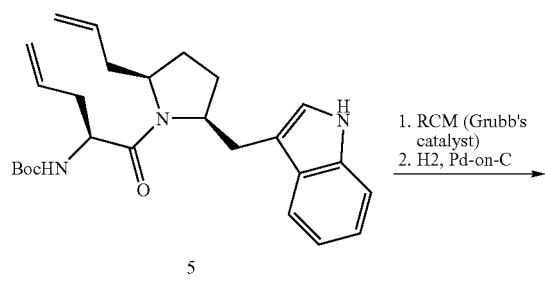
5

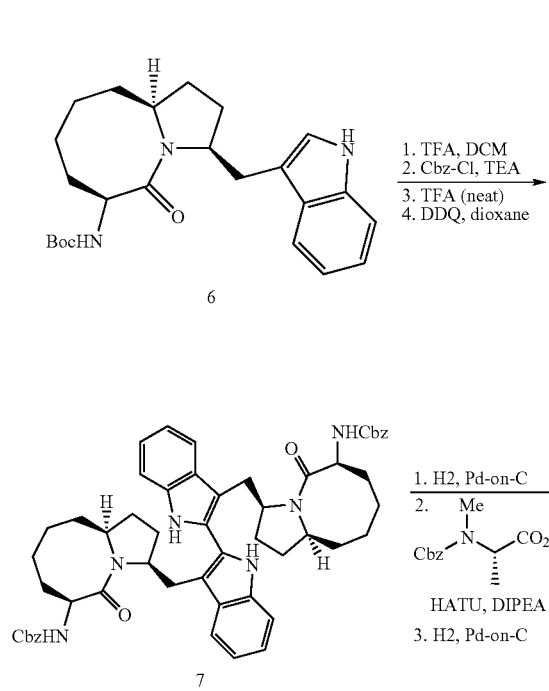

Compounds of formula 18 can be prepared using methods outlined in Schemes III and IV and described in Jako et al. (J. Org. Chem. 1991, 56, 5729-5733), Kozikowski et al. (J. Am. Chem. Soc. 1995, 117, 6666-6672), Sheppard et al. (J. Med. Chem. 1994, 37, 2011-2032), and in U.S. Patent Application Publication Number 20060025347 and U.S. patent application Ser. No. 11/363,387 flied Feb. 27, 2006, all of which are incorporated by reference herein as though fully set forth, and described in Schemes III and IV.

Scheme III

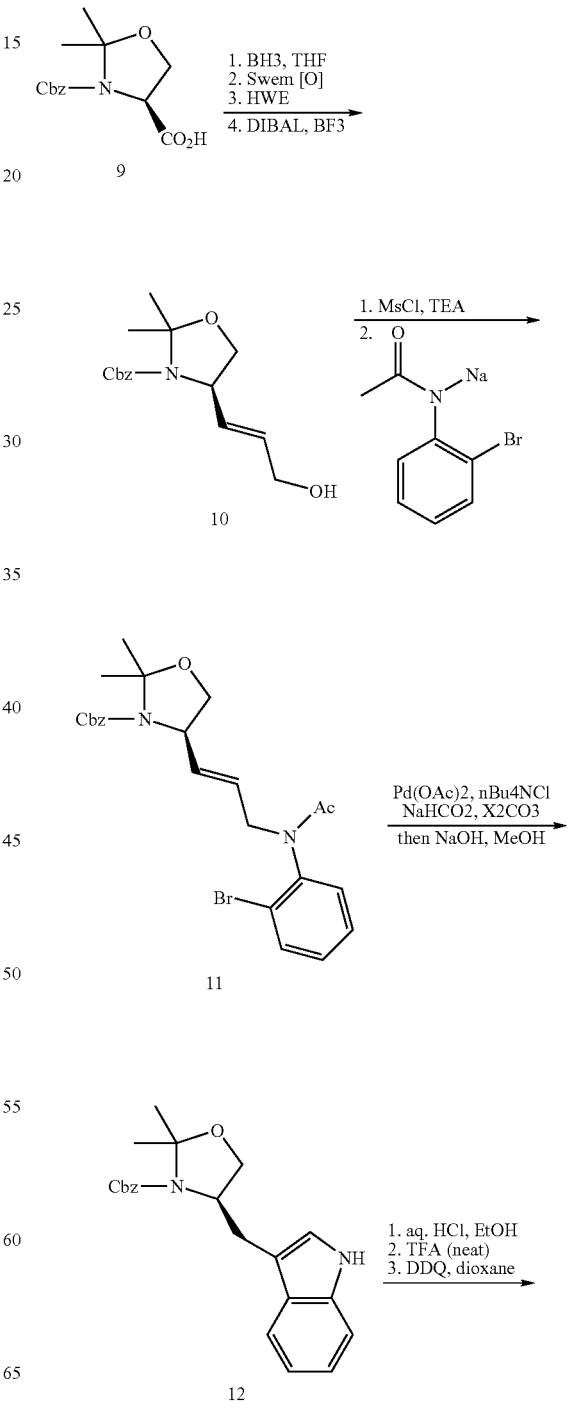

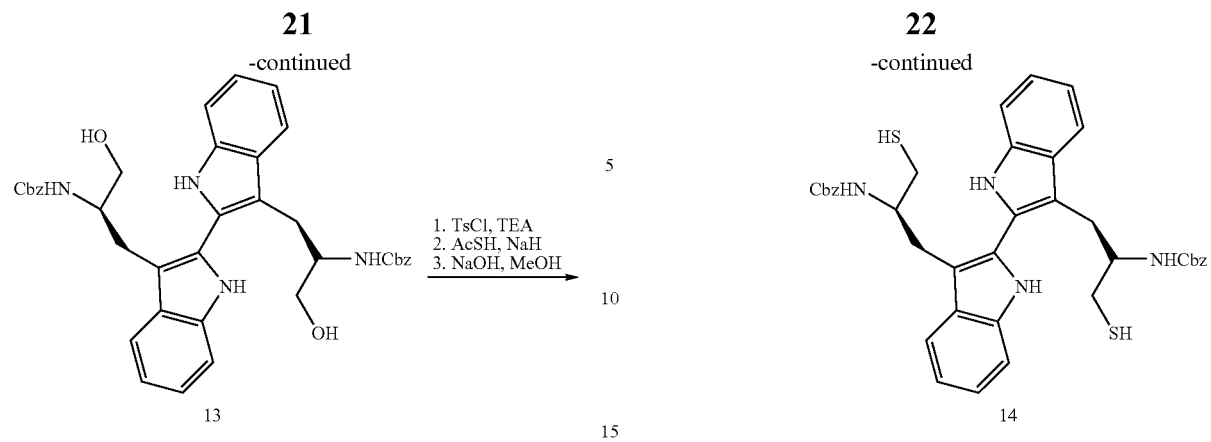
Scheme IV
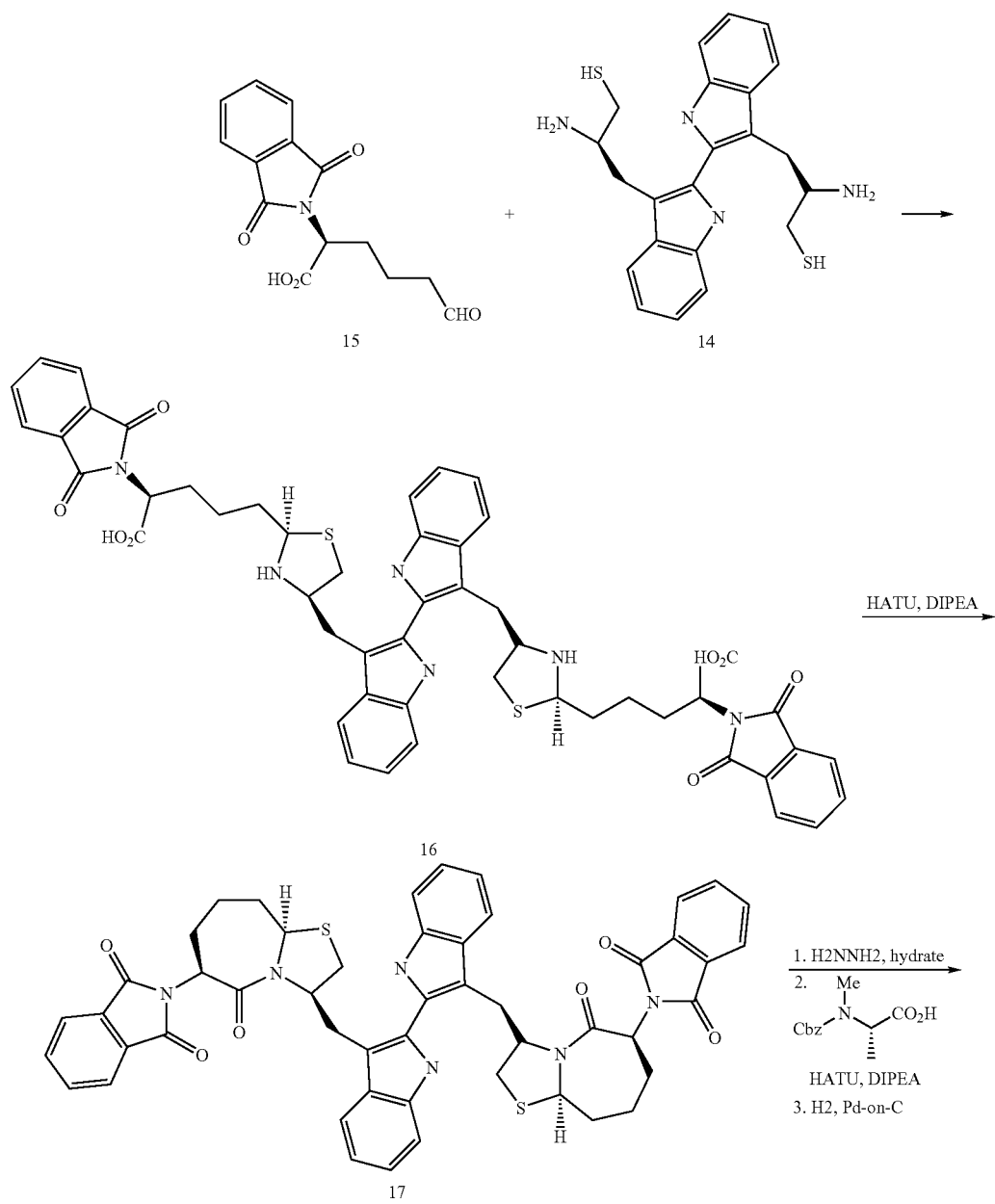

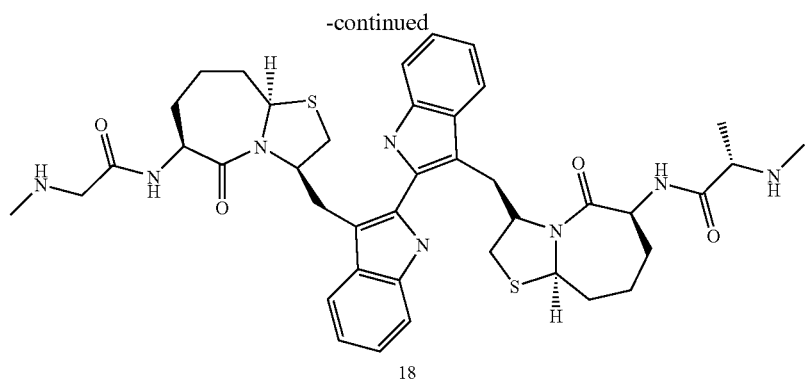
18
Compounds of formula 29 can be prepared using methods outlined in Liu et al., (Tetrahedron 2003, 59, 8515-8523), Mish et al. (J. Am. Chem. Soc. 1997, 119, 8379-8380), and in U.S. Patent Application Publication Number 20060025347 and U.S. patent application Ser. No. 11/363,387 filed Feb. 27, 2006, all of which are incorporated by reference herein as though fully set forth, and described in Schemes V and VI.
Scheme V
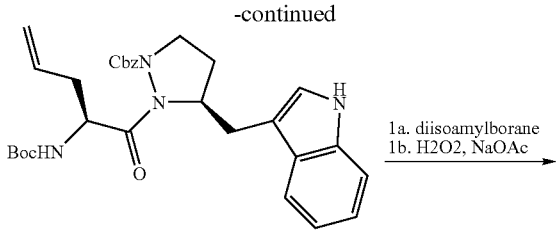
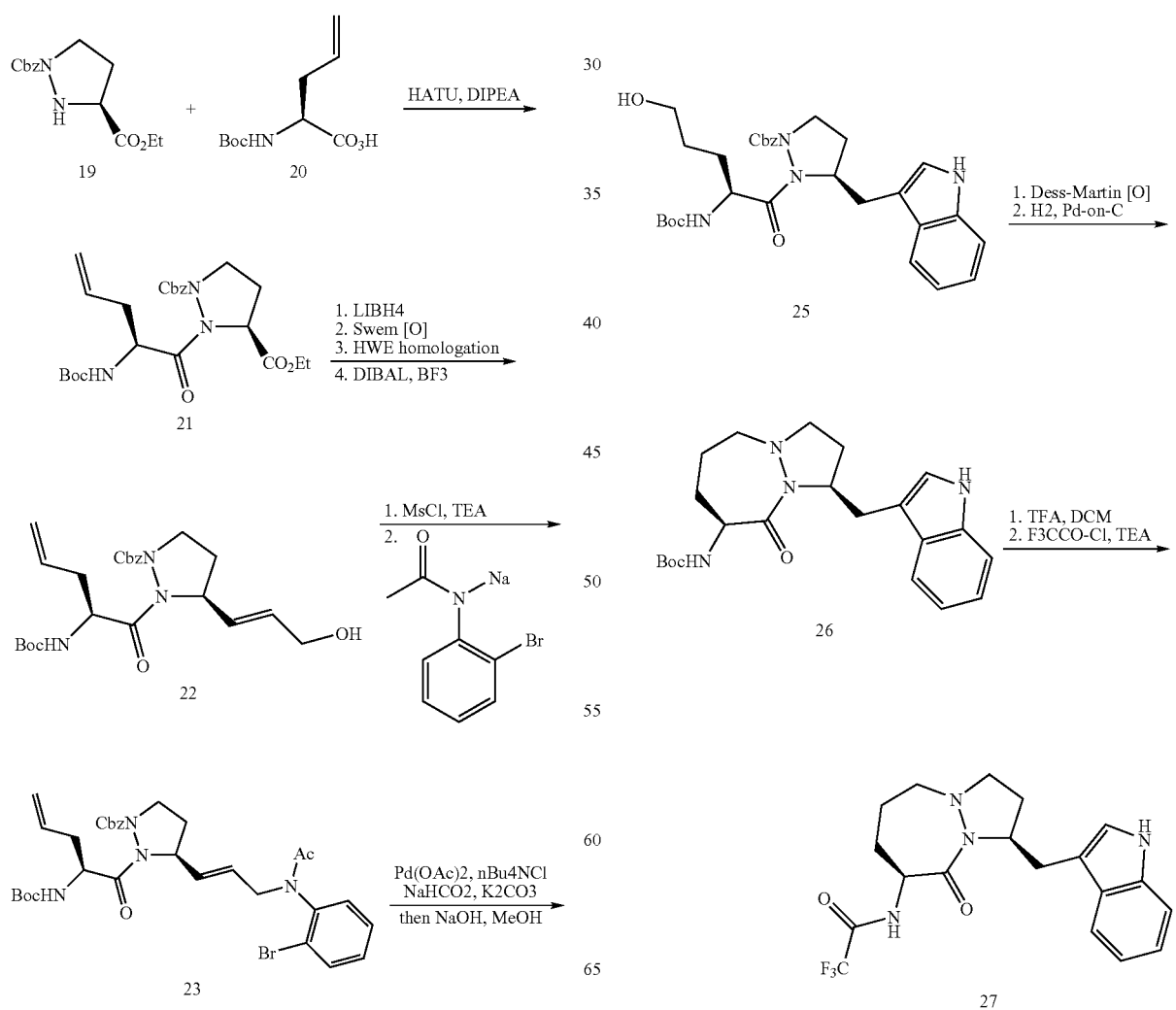

Scheme VI
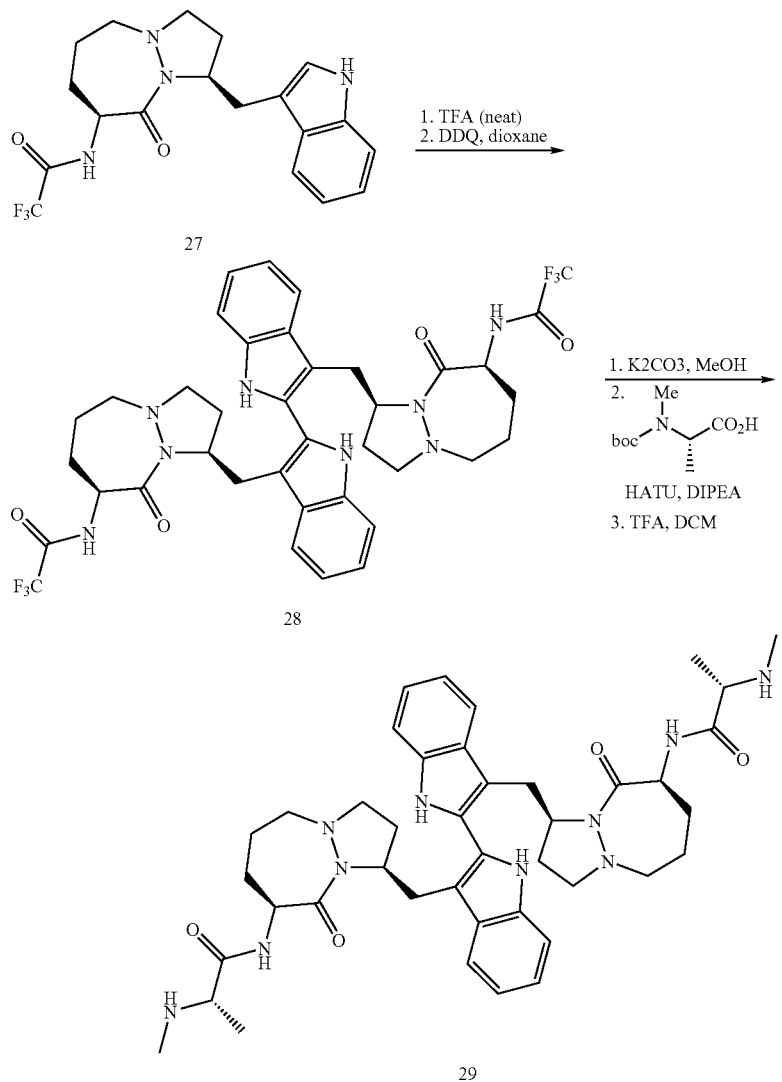
Compounds of formula 36 can be prepared using methods outlined in Hoffmann et al., (J. Org. Chem. 2003, 68, 62-69) and in U.S. Patent Application Publication Number 20060025347 and U.S. patent application Ser. No. 11/363,387 filed Feb. 27, 2006, all of which are incorporated by reference herein as though fully set forth, and described in Schemes VII and VIII.
Scheme VII
-continued
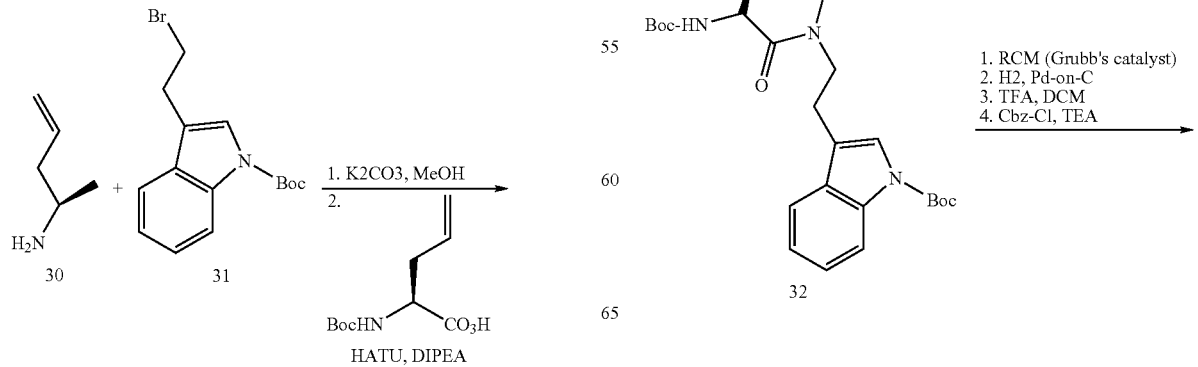

27
-continued
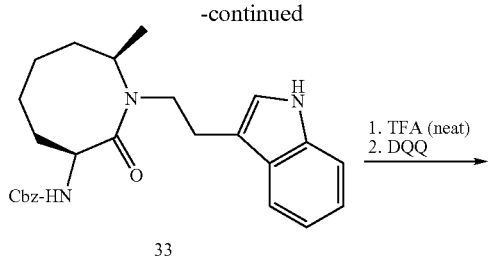
33
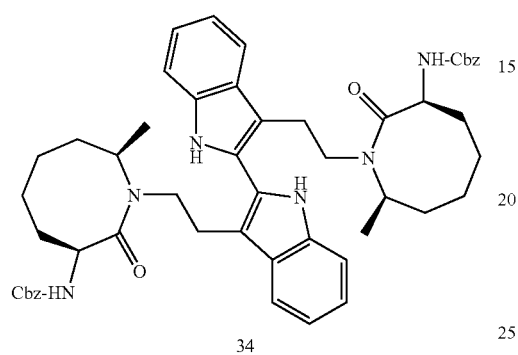
34
Scheme VIII
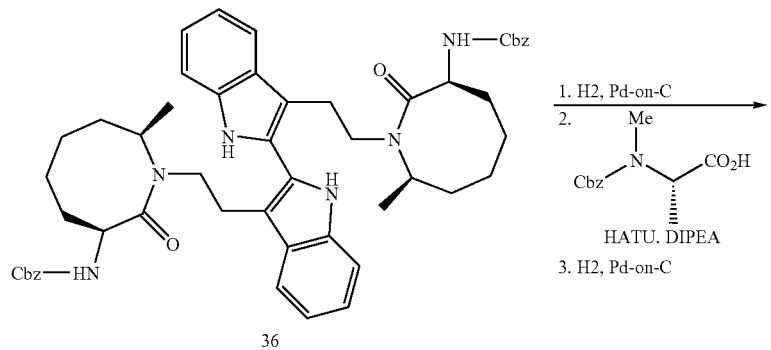
36
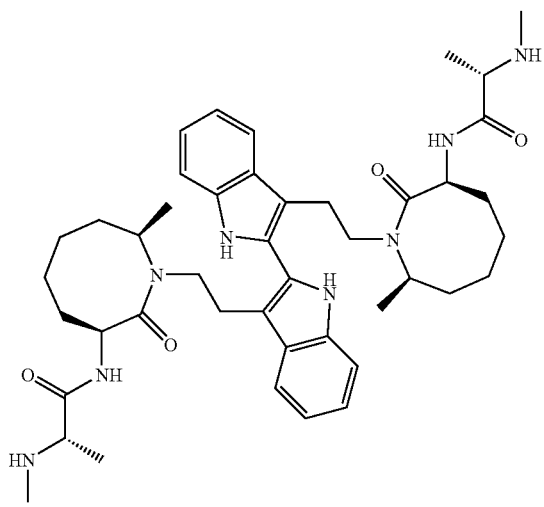
38
28
Additional compounds of the invention can be prepared can be prepared substantially as described in Schemes IX-XXIX, below.
Scheme IX
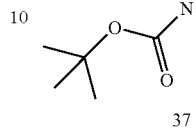
37
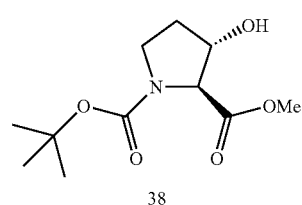
38
3-Hydroxypyrrolidine-1,2-dicarboxylic acid 1-tert-butyl ester 2-methyl ester (38): A solution containing 3-hydroxy-pyrrolidine-1,2-dicarboxylic acid 1-tert-butyl ester (37, 16 g, 71 mmol)[1] in DMF (100 mL) was cooled to 0° C. To this solution was added K$_2$CO$_3$ (16 g, 116 mmol) followed by iodomethane (5.4 mL, 87 mmol). The reaction mixture was slowly warmed to ambient temperature over 1 h at which time it became a yellow heterogeneous solution. This mixture was heated at 90° C. for 1 h and then cooled to ambient temperature. The solution was diluted with brine, extracted with diethyl ether, dried over anhydrous Na$_2$SO$_4$, filtered, and concentrated to afford 14.8 g (87%) of 38 as a yellow oil.[2]

[1]Hodges, J. A.; Raines, R. T. *J. Am. Chem. Soc.* 2005, 45, 15923.
[2]Demange, L.; Cluzeau, J.; Menez, A.; Dugave, C. *Tetrahedron Lett.* 2001, 42, 651.

3-(tert-Butyldimethylsilanyloxy)-2-hydroxymethylpyrrolidine-1-carboxylic acid tert-butyl ester (40): A solution containing 39 (12 g, 33 mmol) in THF (50 mL) was cooled to 0° C. LiBH$_4$ in THF (2M, 20 mL) was added in a dropwise fashion. After 1 h, the solution was warmed to ambient temperature. After 2 h, the solution was diluted with MeOH, then 120, and concentrated. The residue was extracted with EtOAc, washed with 1M HCl, saturated aqueous NaHCO$_3$, brine, dried over anhydrous Na$_2$SO$_4$, filtered, and concentrated to afford 9.5 g (87%) of 40 as a colorless oil.[3]

[3]Herdeis, C.; Hubmann, H. P.; Lotter, H. *Tetrahedron: Asymmetry*, 1994, 5, 119.

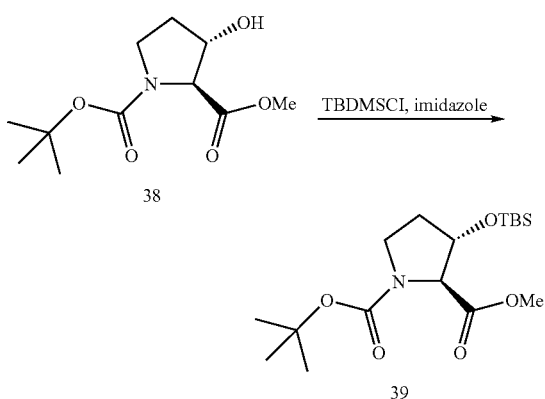

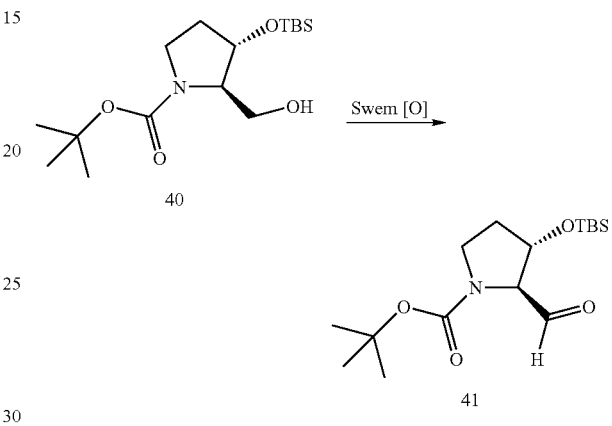

3-(tert-Butyldimethylsilanyloxy)pyrrolidine-1,2-dicarboxylic acid 1-tert-butyl ester 2-methyl ester (39): A solution containing alcohol 38 (14.8 g, 60 mmol) in DCM (150 mL) was cooled to 0° C. To this solution was added imidazole (5.4 g, 79 mmol) followed by t-butyl-dimethylsilyl-chloride (10 g, 66 mmol) in two portions. The reaction mixture was warmed to ambient temperature over 1 h. After 5 h, the solution was diluted with 1M HCl and extracted twice with DCM. The combined organic extracts were dried over anhydrous Na$_2$SO$_4$, filtered, and concentrated to afford 21.2 g (99%) of 39 as a yellow oil. $^1$H NMR (CDCl$_3$, 300 MHz) δ4.38-4.34 (m, 1H), 4.18 (bs, rotomers, 0.5H), 4.04 (app d, J, =2.1 Hz, rotomers, 0.5H), 3.74 (s, 3H), 3.62-3.50 (m, 2H), 2.04-1.96 (m, 1H), 1.85-1.78 (m, 1H), 1.46 (s, minor rotomer), 1.41 (s, 9H), 0.92 (s, minor rotomer), 0.86 (s, 9H), 0.11 (s, 6H), 0.09 (s, minor rotomer) ppm.

3-(tert-Butyldimethylsilanyloxy)-2-formylpyrrolidine-1-carboxylic acid tert-butyl ester (41): A solution containing 2M oxalyl chloride in DCM (22 mL) in DCM (40 mL) was cooled to −78° C. A solution containing DMSO (3.2 mL, 45 mmol) in DCM (20 mL) was added in a dropwise fashion. After 45 min, alcohol 40 (9.5 g, 29 mmol) in DCM (50 mL) was added in a dropwise fashion. After 45 min, TEA (16 mL, 115 mmol) was added in a dropwise fashion. The reaction mixture was warmed and maintained at 0° C. for 15 min. The solution was diluted with 1M HCl, extracted with DCM, washed with brine, dried over anhydrous Na$_2$SO$_4$, filtered, and concentrated to afford 9.5 g (100%) of 41 as a yellow oil. $^1$H NMR (CDCl$_3$, 300 MHz) δ9.53 (d, J=29 Hz, 1H), 4.39-4.36 (m, 1H), 4.24 (m, rotomer, 0.5H), 3.93 (m, rotomer, 0.5H), 3.73-3.49 (m, 2H), 1.98-1.86 (m, 2H), 1.47 (s, minor rotomer), 1.41 (s, 9H), 0.88 (s, 9H), 0.09 (s, 6H), 0.07 (s, minor rotomer) ppm.

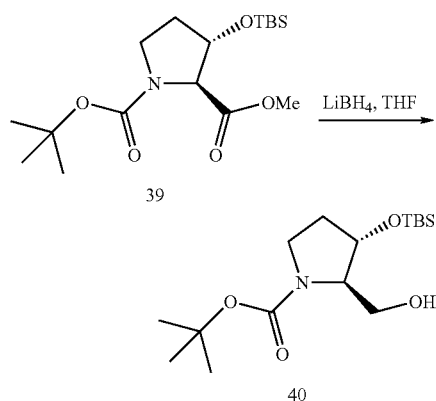

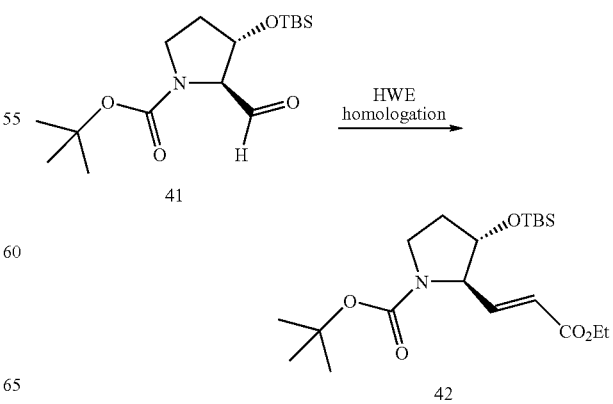

3-(tert-Butyldimethylsilanyloxy)-2-(2-ethoxycarbonylvinyl)pyrrolidine-1-carboxylic acid tert-butyl ester (42): To a suspension containing NaH (60%, 1.9 g, 46 mmol) in THF (50 mL) was slowly added triethylphosphonoacetate (7.5 mL, 38 mmol) in THF (20 mL) at 0° C. After 30 min, a solution containing aldehyde 41 (9.5 g, 29 mmol) in THF (40 mL) was then added in a dropwise fashion. The solution became orange-colored and stirring was continued for 0.5 h. The reaction mixture was diluted with brine, extracted with EtOAc, dried over anhydrous $Na_2SO_4$, filtered, and concentrated to afford 8.6 g (74%) of 42 as a yellow oil which was used without further purification. $^1$H NMR (CDCl$_3$, 300 MHz) δ6.82-6.72 (m, 1H), 5.87 (d, J=15.6 Hz, 1H), 4.24-4.11 (m, 4H), 3.67-3.46 (m, 2H), 1.94-1.89 (m, 1H), 1.79 (m, 1H), 1.48 (s, rotomer, 4.5H), 1.41 (s, rotomer, 4.5H), 1.31-1.24 (m, 3H), 0.91-0.88 (m, 9H), 0.09-0.07 (m, 6H) ppm.

Scheme XIV

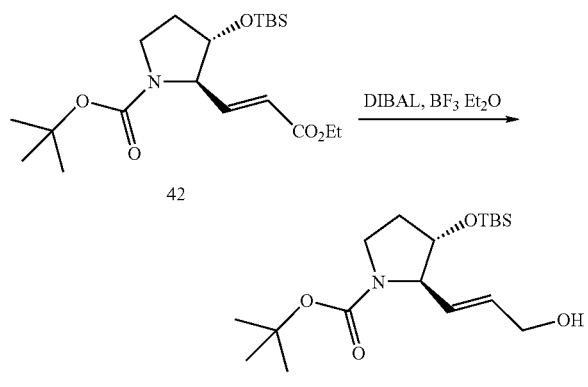

3-(tert-Butyldimethylsilanyloxy)-2-(3-hydroxypropenyl)pyrrolidine-1-carboxylic acid tert-butyl ester (43): A solution containing 42 (8.6 g, 22 mmol) in DCM (80 ml) was cooled to −78° C. To this solution was slowly added boron trifluoride etherate (2.8 mL, 22 mmol) followed by the addition of 1M DIBALH in DCM (60 mL). The solution was stirred at −78° C. for 1 h. The reaction mixture was then treated with EtOAc and stirred for 30 min. The reaction mixture was allowed to warm to −5° C. The reaction was quenched by the dropwise addition of 1M HCl. The mixture was diluted with DCM and H$_2$O and the layers were separated. The aqueous layer was extracted with DCM. The combined organic extracts were dried over anhydrous Na$_2$SO$_4$, filtered, and concentrated to afford 8.5 g of 43 as a light yellow oil which was used without further purification. $^1$H NMR (CDCl$_3$, 300 MHz) δ5.70 (m, 1H), 5.59-5.55 (m, 1H), 4.16-4.13 (m, 2H), 4.05 (m, 2H), 3.72-3.35 (m, 4H), 1.95-1.88 (m, 2H), 1.77-1.67 (m, 2H), 1.48-1.44 (m, 9H), 0.88 (s, 9H), 0.08-0.03 (m, 6H) ppm.

Scheme XV

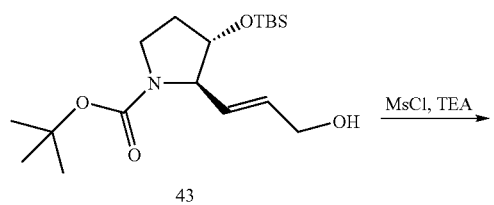

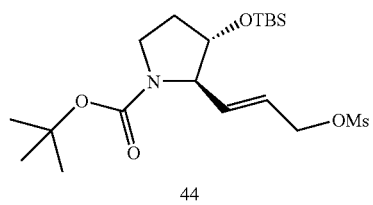

trans-2R-[3-(tert-Butyldimethylsilanyloxy)]-2-(3-methanesulfonyloxypropenyl)pyrrolidine-1-carboxylic acid tert-butyl ester (44): To a solution containing alcohol 43 (8.5 g, 24 mmol) in DCM (30 mL) was added triethylamine (4.0 mL, 29 mmol). The solution was cooled in an ice bath and methanesulfonyl chloride (2 mL, 26 mmol) was added in a dropwise fashion. The reaction mixture was stirred at ambient temperature for 30 min. Water (10 mL) was added and the product was extracted with DCM (3×50 mL). The organic extracts were combined and washed with 1M HCl, brine, dried over anhydrous Na$_2$SO$_4$, filtered, and concentrated to afford 8.9 g of 44 (92% over two steps) as an orange oil that was used without further purification. $^1$H NMR (CDCl$_3$, 300 MHz) δ5.73 (m, 1H), 4.71 (d, J=5.4 Hz, 1H), 4.30-4.15 (m, 1H), 4.06 (m, 1H), 3.54-3.33 (m, 2H), 3.02 (s, 3H), 1.94-1.89 (m, 1H), 1.79-1.78 (m, 1H), 1.45-1.43 (m, 9H), 0.92-0.87 (m, 9H), 0.09-0.07 (m, 6H) ppm.

Scheme XVI

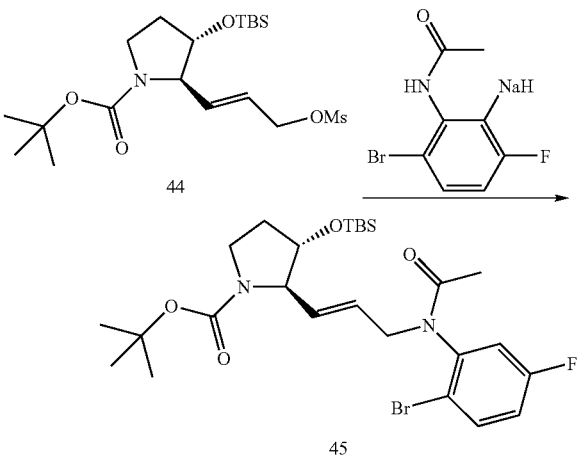

trans-2R-[2-{3-[Acetyl-(2-bromo-5-fluorophenyl)amino]propenyl}]-3-(tert-butyldimethylsilanyloxy)pyrrolidine-1-carboxylic acid tert-butyl ester (45): To a solution containing N-(2-bromo-5-fluorophenyl)acetamide (5.7 g, 24 mmol) in DMF (30 mL) was added NaH (60%, 1.2 g, 30 mmol) at 0° C. After 30 min, the solution was warmed and maintained at ambient temperature for 30 min. To this solution was slowly added mesylate 44 (8.9 g, 24 mmol) in DMF (30 mL) at 0° C. The reaction was allowed to slowly warm to ambient temperature over 1 h. After 2 h, the solution was diluted with brine, extracted with diethyl ether, washed twice with brine, dried over anhydrous Na$_2$SO$_4$, filtered, and concentrated to afford 12 g of crude 45 (the product contained unreacted acetanilide that co-eluted on TLC) which was used without further purification.

Scheme XVII

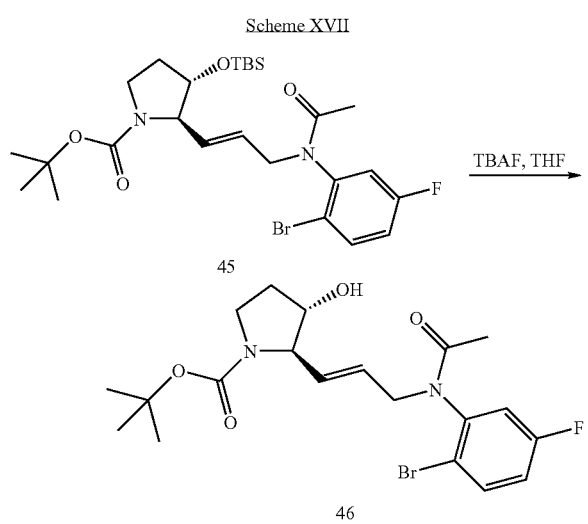

trans-2R-[2-{3-[Acetyl(2-bromo-5-fluorophenyl)amino]propenyl}]-3-hydroxypyrrolidine-1-carboxylic acid tert-butyl ester (46): To a solution containing crude 45 (11 g, approx., 19 mmol) in THF (30 mL) was added 1M TBAF/THF (25 mL) at ambient temperature. After 1 h, the solution was diluted with EtOAc, washed with 1M HCl, brine, dried over anhydrous $Na_2SO_4$, filtered, and concentrated. The residue was absorbed on silica gel and purified by flash silica gel chromatography (1:1 hexanes/EtOAc to 5% MeOH/DCM) to afford 4.2 g of alcohol 46 as an orange foam. $^1$H NMR ($CDCl_3$, 300 MHz) δ7.65 (m, 1H), 7.04-7.02 (m, 2H), 5.62 (m, 1H), 5.40-5.34 (m, 1H), 4.74-4.69 (m, 1H), 4.26-4.00 (m, 2H), 3.74-3.38 (m, 3H), 2.69-2.57 (m, 1H), 1.82 (s, 3H), 1.46 (s, 9H) ppm.

Scheme XVIII

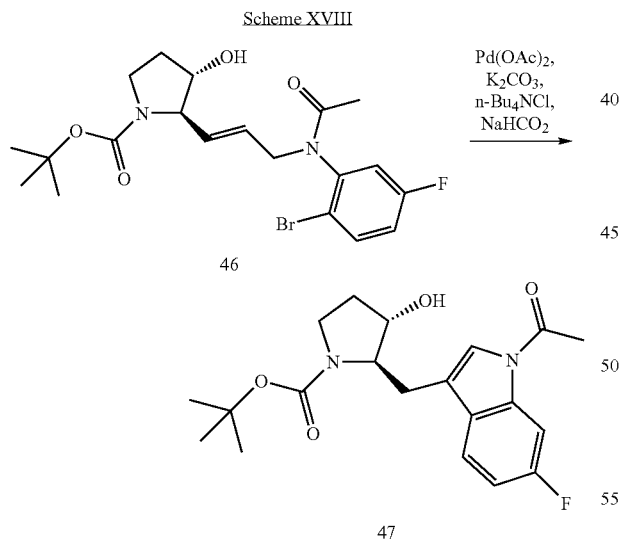

trans-2R-[2-(1-Acetyl-6-fluoro-1H-indol-3-ylmethyl)]-3-hydroxypyrrolidine-1-carboxylic acid tert-butyl ester (47): To a solution containing 46 (5.7 g, 12.5 mmol) in DMF (40 mL) was added $K_2CO_3$ (1.7 g, 12.3 mmol), sodium formate (0.86 g, 12.7 mmol) tetrabutylammonium chloride (3.5 g, 12.7 mmol), and $Pd(OAc)_2$ (0.32 g, 1.4 mmol) at ambient temperature. This reaction mixture was immersed in an oil bath preheated to 90° C. After 4 h, the reaction mixture was cooled in an ice bath, diluted with brine, extracted with EtOAc, washed twice with brine, dried over anhydrous $Na_2SO_4$, filtered, and concentrated to afford 4.5 g of crude indole 47 as an orange foam that was used without further purification.

Scheme XIX

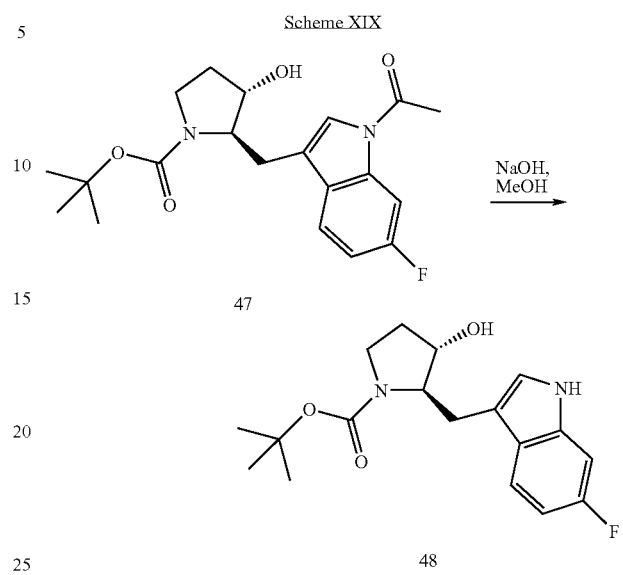

trans-2R-[2-(6-Fluoro-1H-indol-3-ylmethyl)]-3-hydroxypyrrolidine-1-carboxylic acid tert-butyl ester (48): To a solution containing acetate 47 (2.5 g, 6.6 mmol) in MeOH (15 mL) was added 1M NaOH (8 mL) at ambient temperature. After 40 min, the solution was concentrated, diluted with EtOAc, washed with brine, dried over anhydrous $Na_2SO_4$, filtered, and concentrated. The residue was purified by NP-HPLC ($SiO_2$, 40% EtOAc/hexanes increasing to EtOAc over 30 min) to afford 1.3 g of indole 48 as a light yellow foam. $^1$H NMR ($CDCl_3$, 300 MHz) δ8.75 (s, rotomer, 0.51H), 8.71 (s, rotomer, 0.5H), 7.52 (dd, J=9.0, 14.1 Hz, 1H), 7.03-6.81 (m, 3H), 4.15-4.08 (m, 2H), 3.96 (dd, J=3.3, 10.2 Hz, 1H), 3.57-3.33 (m, 2H), 3.22-3.09 (m, 1H), 2.60-2.49 (m, 2H), 2.01-1.91 (m, 1H), 1.79-1.75 (m, 1H), 1.50 (s, 9H) ppm.

Scheme XX

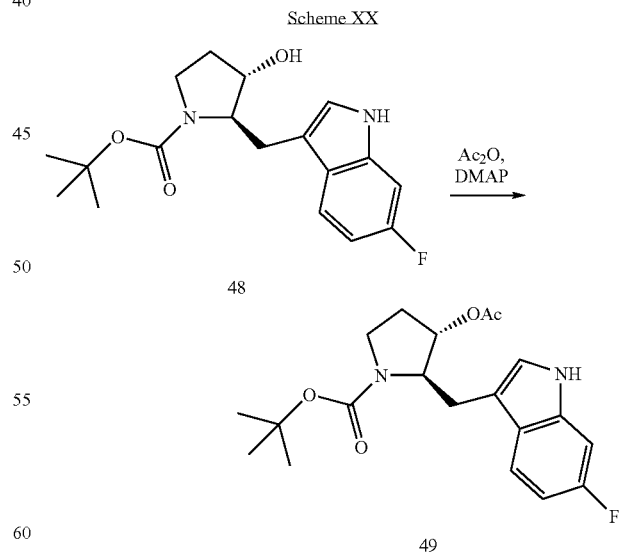

trans-2R-[3-Acetoxy-2-(6-fluoro-1H-indol-3-ylmethyl)]pyrrolidine-1-carboxylic acid tert-butyl ester (49): To a suspension containing indole 48 (0.35 g, 1.1 mmol) in DCM (10 mL) was added acetic anhydride (0.15 mL, 1.5 mmol) followed by DMAP (10 mg, 0.08 mmol) at ambient temperature. After 30 min, the solution became homogeneous, After 1 h, the solution was diluted with 1M HCl, extracted with DCM, dried over anhydrous Na$_2$SO$_4$, filtered, and concentrated to afford 0.36 g (87%) of 49 as a yellow oil. $^1$H NMR (CDCl$_3$, 300 MHz) δ8.62 (s, rotomer, 0.5H), 8.57 (s, rotomer, 0.5H), 7.62-7.51 (m, 1H), 7.03 (d, J=7.8 Hz, 1H), 6.98 (s, 1H), 6.90-6.85 (m, 1H), 5.05 (s, 1H), 4.18-4.08 (m, 1H), 3.51-3.11 (m, 3H), 2.90-2.44 (m, 1H), 2.23 (s, 3H), 1.86-1.84 (m, 2H), 1.53 (s, 9H) ppm.

(m, 1H), 3.44 (m, 1H), 3.07-3.00 (m, 21J), 2.82 (dd, J=8.1, 14.7 Hz, 1H), 2.14-2.03 (m, 2H), 2.03 (s, 3H), 1.82-1.79 (m, 1H) ppm.

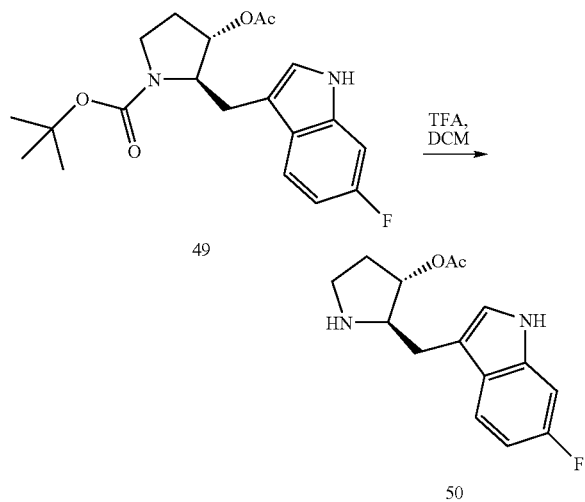

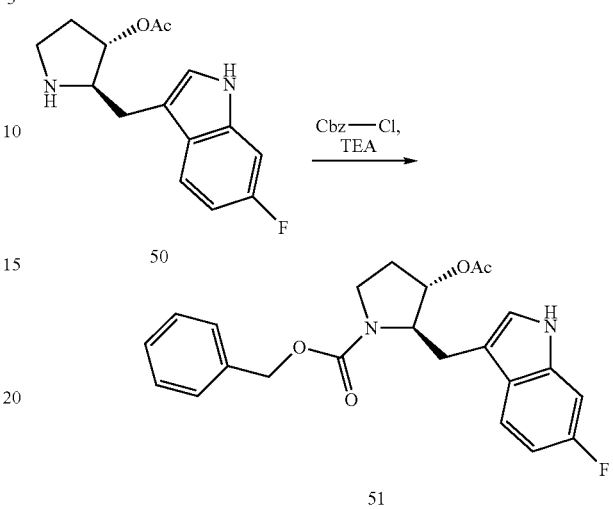

trans-2R-[Acetic acid 2-(6-fluoro-1H-indol-3-ylmethyl)] pyrrolidin-3-yl ester (50): To a solution containing carbamate 49 (0.48 g, 1.3 mmol) in DCM (15 mL) at 0° C. was added TFA (3 mL). After 15 min, the reaction was warmed and maintained at ambient temperature for 1 h. The solution was concentrated, diluted with EtOAc, washed with saturated NaHCO$_3$, dried over anhydrous Na$_2$SO$_4$, filtered, and concentrated to afford 0.32 g (89%) of amine 50 as an orange oil that was used without further purification. $^1$H NMR (CDCl$_3$, 300 MHz) δ8.25 (s, 1H), 7.52 (dd, J=5.4, 8.7 Hz, 1H), 7.03-6.91 (m, 2H), 6.88 (ddd, J=0.9, 8.7, 17.4 Hz, 1H), 5.01-4.98

Cbz-protected pyrrolidine (51): A solution containing amine 50 (0.65 g, 2.4 mmol) in DCM (25 mL) was treated with CbzCl (0.35 ml, 2.5 mmol) followed by TEA (0.5 mL, 1.4 mmol) at 0° C. After 15 min. the solution was warned to ambient temperature. After 1 h, the reaction mixture was diluted with 1M HCl and extracted with DCM. The combined organic extracts were dried over Na$_2$SO$_4$, filtered and concentrated. The residual oil was purified by preparative HPLC (SiO$_2$, 20-100% EtOAc/hexanes) to give 0.98 g (100%) of 51 as a yellow oil. $^1$H NMR (CDCl$_3$, 300 MHz): ~1:1 mixture of amide rotamers, δ8.27 (s, 1H), 7.62 (app q, J=5.4 Hz, 0.5H), 7.16 (app q, J=5.1 Hz, 0.5H), 7.44-7.37 (m, 5H), 6.89-6.92 (m, 1H), 6.83 (m, 0.5H), 6.65 (m, 0.5H), 5.30-5.16 (m, 2H), 5.09-5.07 (m, 1H), 4.23 (dd, J=3.3, 9 Hx, 0.5H), 4.12 (dd, J=3.6, 9.6 Hz, 0.5H), 3.58-3.45 (m, 2H), 3.30-3.12 (m, 1H), 2.85-2.64 (m, 1H), 1.99-1.86 (m, 5H) ppm.

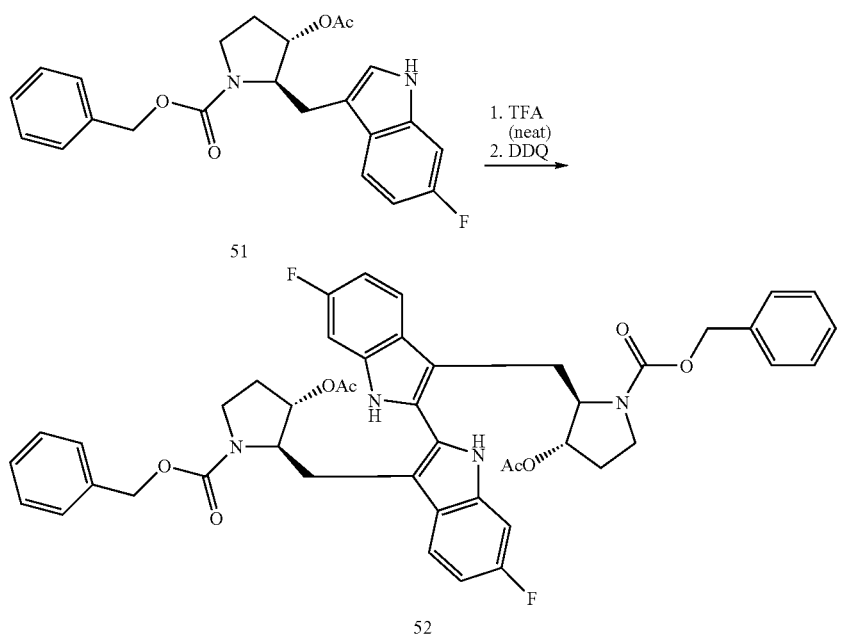

Biindole (52); Indole 51 (0.98 g, 2.4 mmol) was dissolved in TFA (20 mL) at 0° C. and the reaction was monitored by LC/MS analysis. After 5 h, the reaction mixture was diluted with cold saturated $K_2CO_3$, and extracted with EtOAc. The combined organic extracts were washed with saturated $NaHCO_3$ then brine, dried over anhydrous $Na_2SO_4$, filtered and concentrated to give 0.8 g of a yellow oil that was used without further purification. This oil was diluted with EtOAc (10 mL) and treated with DDQ (315 mg, 1.4 mmol) at ambient temperature. After 15 min, the dark green solution was diluted with saturated $NaHCO_3$, and extracted with EtOAc. The combined organic extracts were washed with saturated $NaHCO_3$, brine, dried over anhydrous $Na_2SO_4$, filtered and concentrated. The crude residue was absorbed on $SiO_2$ gel and purified by flash chromatography ($SiO_2$, 2:1 hexanes/EtOAc) to give 0.6 g (61%) of 52 as a light yellow foam. $^1$H NMR (CDCl$_3$, 300 MHz) δ 11.2 (s, 1H), 7.51-7.26 (m, 5H), 6.93 (app t, J=8.4 Hz, 1H), 5.36 (s, 2H), 5.24 (s, 1H), 4.17 (d, J=9.9 Hz, 1H), 3.74 (app t, J=9.6 Hz, 1H), 3.62-3.56 (m, 2H), 2.89 (app t, J=14.1 Hz, 1H), 2.24-2.17 (m, 1H), 1.85 (s, 3H) ppm. Mass spectrum, m/z 820.8 $(M^+H)^+$, 842.7 $(M^+Na)^+$.

Scheme XXIV

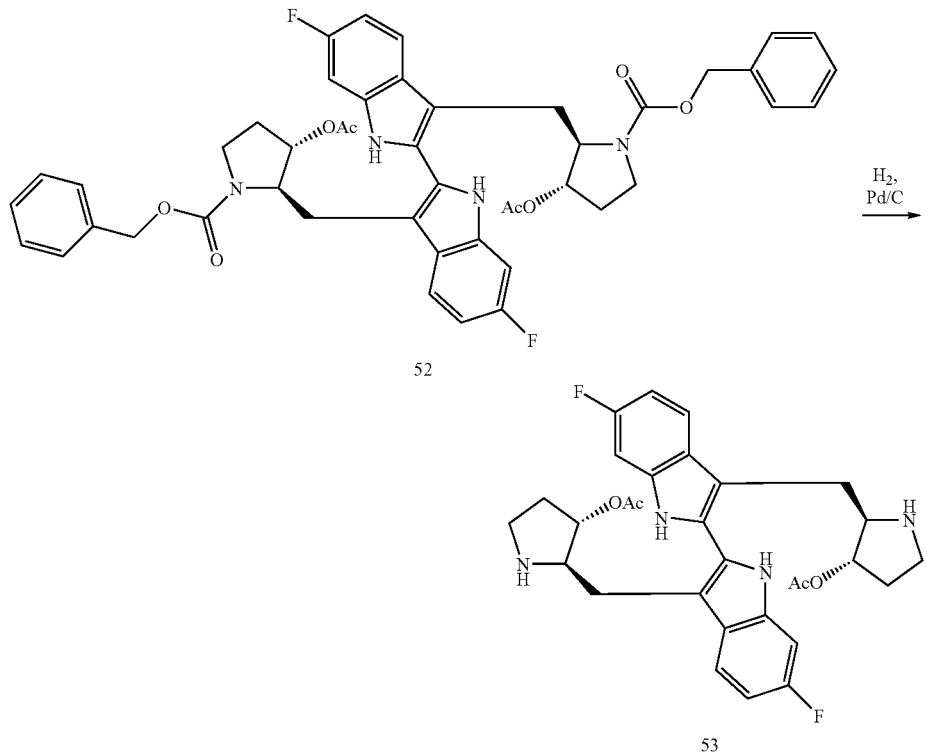

Bis-pyrrolidine (53): To a solution containing biindole 52 (0.6 g, 0.73 mmol) in MeOH (20 mL) was added 10% Pd/C (50 mg). The reaction mixture was shaken under $H_2$ using a Parr apparatus. After 3 h, the mixture was filtered through Celite®, and rinsed with MeOH and EtOAc. The filtrate was concentrated in vacuo to afford 0.32 g (80%) of 53 as an off-white solid that was used without further purification. Mass spectrum, m/z 550.4 $(M)^+$.

Scheme XXV

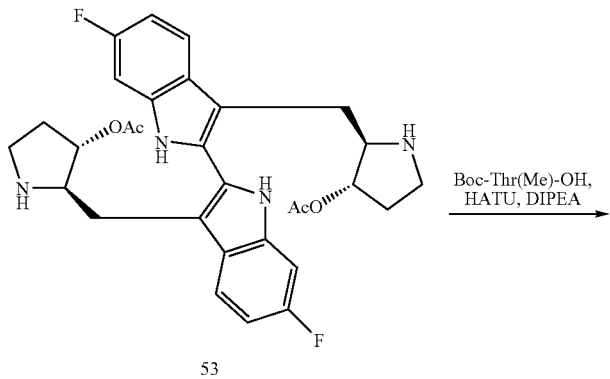

-continued

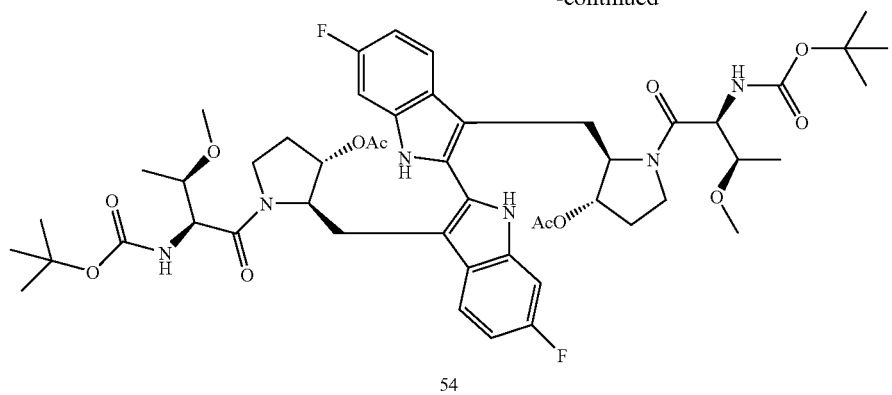

54

Boc-protected dimer (54): A solution containing N-Boc-Thr(Me)-OH (152 mg, 0.65 mmol) in NMP (4 mL) was cooled to 0° C. To this solution was added HATU (224 mg, 0.60 mmol) followed by DIPEA (0.15 mL, 0.80 mmol). After 5 min, diamine 53 (180 mg, 0.33 mmol) in NMP (5 mL) was added. The reaction mixture was warmed to room temperature. After 16 h, the reaction mixture was diluted with EtOAc, washed with 1M HCl, saturated NaHCO$_3$, brine, dried over anhydrous Na$_2$SO$_4$, filtered and concentrated to afford 290 mg of 54 as an orange oil that was used without further purification.

Diamine (55): A solution containing 54 (0.29 g, 0.3 mmol) in DCM (15 mL) was cooled to 0° C. To this solution was added TFA (3 mL). After 15 min, the reaction mixture was warmed to ambient temperature. After 1.5 h, the reaction mixture was concentrated, diluted with EtOAc, washed with saturated NaHCO$_3$, dried over anhydrous Na$_2$SO$_4$, filtered and concentrated to afford 0.19 g (82%) of diamine 55 as a light orange foam that was used without further purification, $^1$H NMR (CDCl$_3$, 300 MHz) δ 11.7 (s, 1H), 7.51 (dd, J=1.8, 11.7 Hz, 1H), 7.38-7.28 (m, 1H), 6.93 (app t, J=7.2 Hz, 1H), 5.30 (d, J=3.3 Hz, 1H), 4.40 (d, J=11.7 Hz, 1H), 4.01 (app t, J=9 Hz, 1H), 3.82 (app q, J=9.9 Hz, 1H), 3.68 (d, J=6.6 Hz, 1H), 3.56-3.50 (m, 1H), 3.46 (s, 3H), 2.92-2.80 (m, 2H), Scheme XXVI

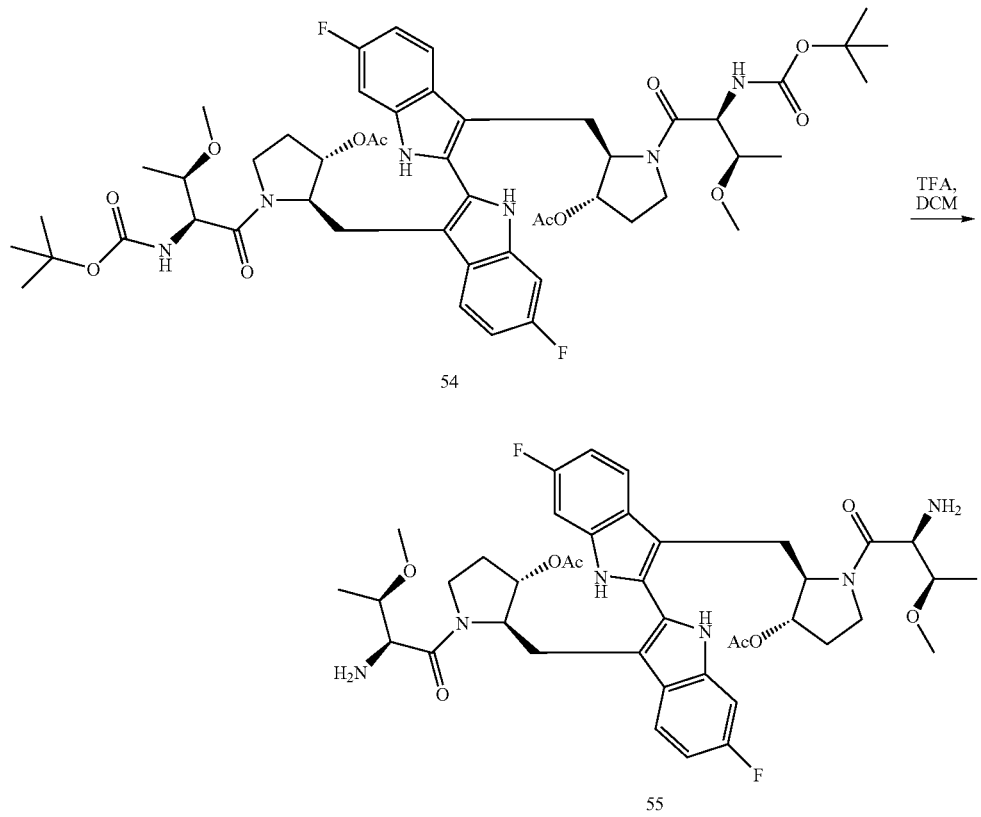

2.67-2.63 (m, 1H), 2.36-2.29 (m, 1H), 1.85 (s, 3H), 1.26-1.23 (m, 4H) ppm. Mass spectrum, m/z 780.8 (M)+·

Scheme XXVII

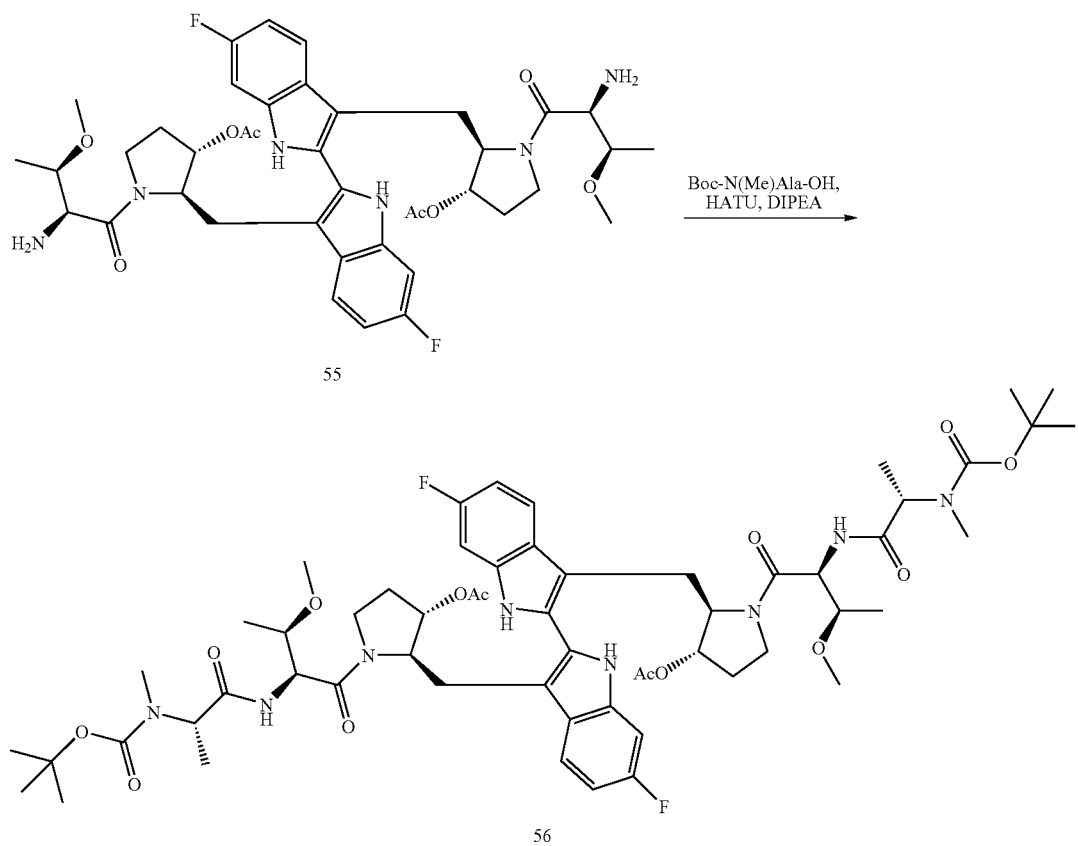

Boc-protected dipeptide (56): A solution containing N-Boc-N(Me)Ala-OH (58 mg, 0.28 mmol) in NMP (4 mL) was cooled to 0° C. To this solution was added HATU (106 mg, 0.28 mmol) followed by DIPEA (0.1 nit, 0.57 mmol). After 5 min, diamine 55 (110 mg, 0.14 mmol) in NMP (5 mL) was added dropwise. The reaction mixture was warmed to room temperature. After 16 h, the reaction mixture was diluted with EtOAc, washed with 1M HCl, saturated NaHCO₃, brine, dried over anhydrous Na₂SO₄, filtered and concentrated to afford 126 mg of 56 as an orange oil that was used without further purification.

Scheme XXVIII

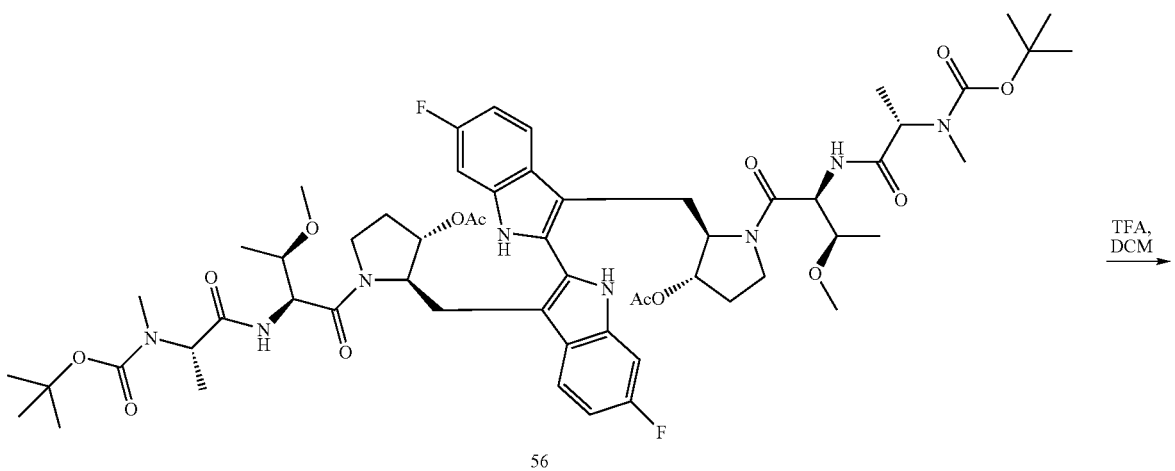

-continued

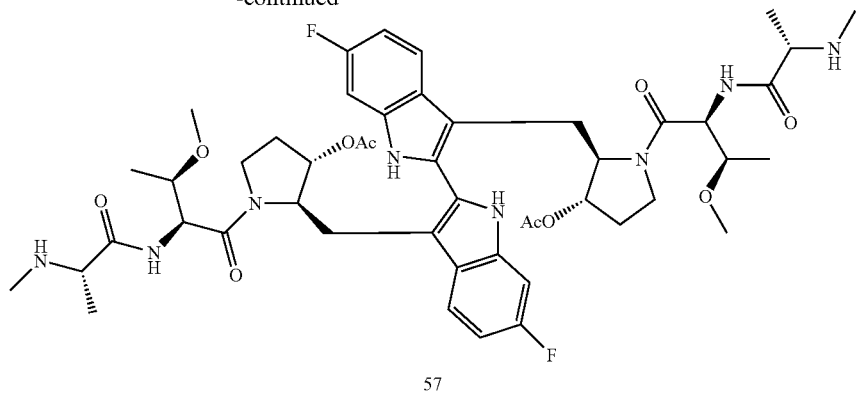

57

Dipeptide (57): A solution containing 56 (126 mg, 0.11 mmol) in DCM (15 mL) was cooled to 0° C. To this solution was added TFA (3 mL). After 15 min, the reaction was warmed to ambient temperature. After 1.5 h, the reaction mixture was concentrated, diluted with EtOAc, washed with saturated NaHCO$_3$, dried over anhydrous Na$_2$SO$_4$, filtered and concentrated to afford 100 mg (95%) of 57 as an orange oil that was used without further purification. $^1$H NMR (CDCl$_3$, 300 MHz) δ 11.73 (s, 1H), 8.49 (d, J=8.1 Hz, 1H), 7.60 (dd, J=2.1, 9.9 Hz, 1H), 7.39-7.34 (m, 1H), 6.94 (app t, J=9 Hz, 1H), 5.26 (d, J=3.6 Hz, 1H), 4.98 (app q, J=3.6 Hz, 1H), 4.38 (d, J=10.8 Hz, 1H), 4.19 (d, J=9.6 Hz, 1H), 3.88-3.73 (m, 2H), 3.61-3.56 (m, 1H), 3.45 (s, 3T), 3.15 (app q, J=6.9 Hz, 1H), 2.92-2.80 (m, 1H), 2.56 (s, 3H), 2.35-2.29 (m, 1H), 1.85 (s, 3H), 1.40 (d, J=6.9 Hz, 3H), 1.28-1.24 (m, 6H) ppm. Mass spectrum, m/z 951.0 (M$^+$H)$^{+\cdot}$ Scheme XXIX

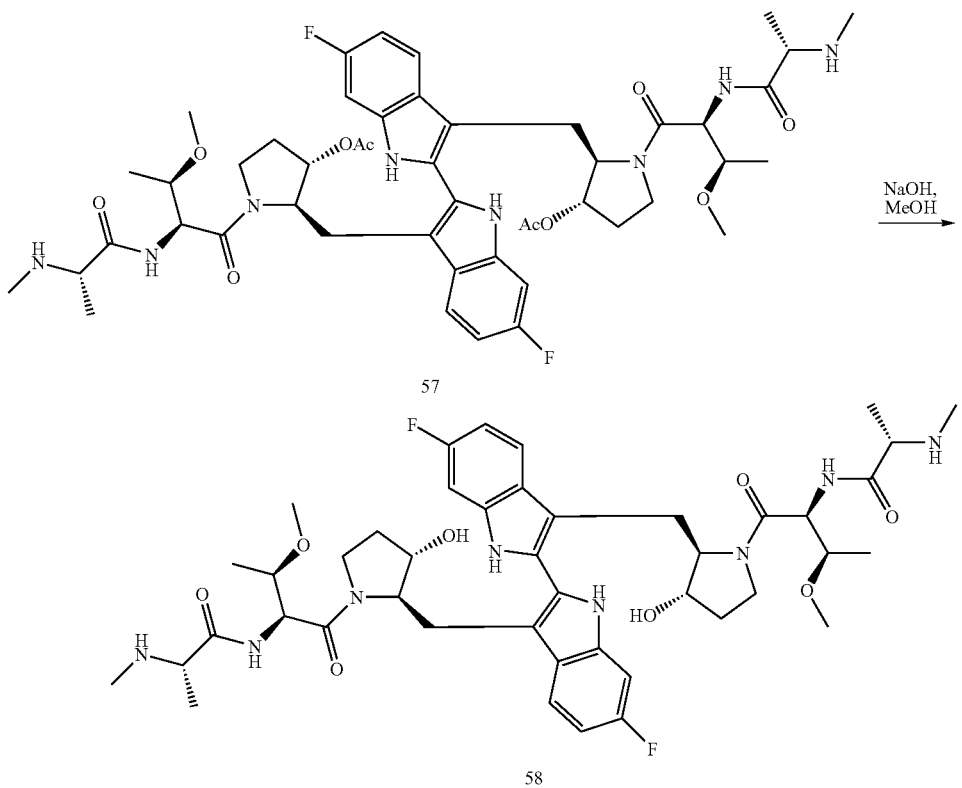

Bis-(3-OH-pyrrolidino)-dipeptide (58): A solution containing 57 (100 mg, 0.11 mmol) in MeOH (10 mL) was treated with 1M NaOH (1 mL) at ambient temperature. After 45 min, the solution was concentrated, diluted with HOAc and water and purified by RP-HPLC [Dynamax Microsorb C18 60 Å, 8 μ, 41.4 mm×25 cm; Flow: 40 mL/min; Detector: 272 nm; Solvent A: water v/v 0.1% HOAc, Solvent B: ACN v/v 0.1% HOAc; Method: 10-90% B over 30 min]. The product-containing fractions were combined, frozen, and lyophilized to afford 40 mg of 58 as a white solid. $^1$H NMR (CDCl$_3$, 300 MHz): ~4:1 mixture of rotamers, δ 11.77 (s, 1H), 10.78 (s, minor), 8.20 (d, J=7.8 Hz, 1H), 7.92 (d, J=9.9 Hz, minor), 7.54 (dd, J=1.8, 9.6 Hz, 1H), 7.04 (dd, 11.8, 9.9 Hz, minor), 7.38-7.25 (m, 2H), 6.92-6.87 (m, 1H), 5.0 (dd, J=3.9, 8.1 Hz, minor), 4.84 (dd, J=3.9, 8.1 Hz, 1H), 4.33 (d, J=2.4 Liz, 1H), 4.23 (d, J=10.8 Hz, 1H), 4.05-3.89 (m, 1H), 3.79-3.74 (m, 1H), 3.55 (app d, J=12.9 Hz, 1H), 3.44 (s, 3H), 3.16-3.05 (m, 2H), 2.82-2.69 (m, 2H), 2.47-2.37 (m, 6H), 2.14-2.08 (m, 1H), 1.94-1.85 (m, 1H), 1.40 (d, J=1-6.9 Hz, 1H), 1.28-1.23 (m, 4H) ppm. Mass spectrum, m/z 866.9 (M)$^{+\cdot}$ Additional IAP antagonists can be prepared using the chemistries outlined in the above Schemes employing the synthetic intermediates described in the following Schemes.

Scheme XXX

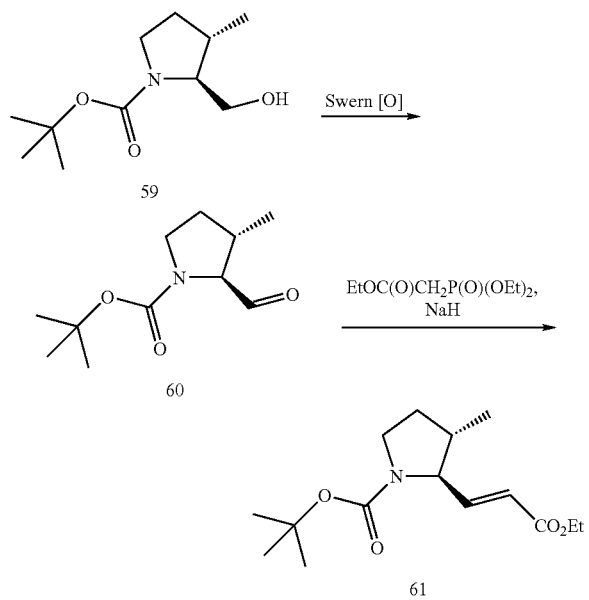

2-Formyl-3-methyl-pyrrolidine-1-carboxylic acid tert-butyl ester (60): A 500-mL three-necked flask equipped with an overhead stirrer and nitrogen inlet was charged with a 1M solution of oxalyl chloride DCM (20.5 mL, 0.041 mol) and anhydrous DCM (100 mL) and cooled to −78° C. A solution of anhydrous DMSO (3.45 mL, 0.044 mol) in DCM (20 mL) was added dropwise with stirring. After 30 min, alcohol 59 (7.35 g, 0.034 mol)[1] was added in DCM (40 mL) in a dropwise fashion. After 30 min, Et$_3$N (23.7 mL, 0.17 mol) was added resulting in the formation of a white suspension. The reaction mixture was transferred to a 0° C. ice/water bath and maintained for 30 min. The reaction mixture was quenched by the addition of water. The product was extracted with DCM and the combined organic extracts were washed successively with water, 1M HCl, and brine. The organic phase was dried over anhydrous Na$_2$SO$_4$, filtered, and concentrated to afford 7.05 g (99%) of aldehyde 60 which was used without further purification. $^1$H NMR (CDCl$_3$, 300 MHz) δ 9.45 (s, minor rotamer), 9.40 (s, 1H, major rotamer), 3.78-3.35 (m, 3H), 2.3-2.0 (m, 2H), 1.70-1.55 (m, 1H), 1.47 (s, minor rotamer), 1.42 (s, 9H, major rotamer), 1.15 (d, J=6 Hz, 3H) ppm.

[1]See: Herdeis, C.; Hubmann, H. P. *Tetrahedron Asymmetry* 1992, 3, 1213-1221; and, Ohfune, Y.; Tomita, M., *J. Am. Chem. Soc.* 1982, 104, 3511-3513.

2-(2-Ethoxycarbonyl-ethyl-3-methyl-pyrrolidine-1-carboxylic acid tert-butyl ester (61): A 500-mL, 3-neck round-bottomed flask was charged with sodium hydride (60%, 1.77 g, 0.044 mol) in anhydrous THF (100 mL) under nitrogen and cooled to 10° C. A solution of triethylphosphono acetate (9.15 g, 0.041 mol) in THF (50 mL) was added drop wise to the NaH/THF suspension. Following the addition, crude aldehyde 60 (7.25 g, 0.034 mol) in THF (15 mL) and added in a drop wise fashion. After ~1 h, the reaction was complete by TLC analysis [30% EtOAc/Hexanes, R$_f$(60)=0.7; R$_f$(61)=0.75]. The reaction mixture was quenched by the addition of saturated aqueous NH$_4$Cl. The product was extracted with EtOAc, washed with 1M HCl, water, brine, dried over anhydrous Na$_2$SO$_4$, filtered, and concentrated to afford 13.3 g of crude 61 (quant.) which was used without further purification. $^1$H NMR (CDCl$_3$, 300 MHz) δ 6.8 (m, 1H), 5.82 (m, 1H), 4.2 (m, 2H), 4.0-3.25 (m, 3H), 2.2-1.85 (m, 2H), 1.70-1.55 (m, 1H), 1.47 (s, minor rotamer), 1.42 (s, 9H, major rotamer), 1.15 (d, J=6 Hz, 3H) ppm.

Scheme XXXI

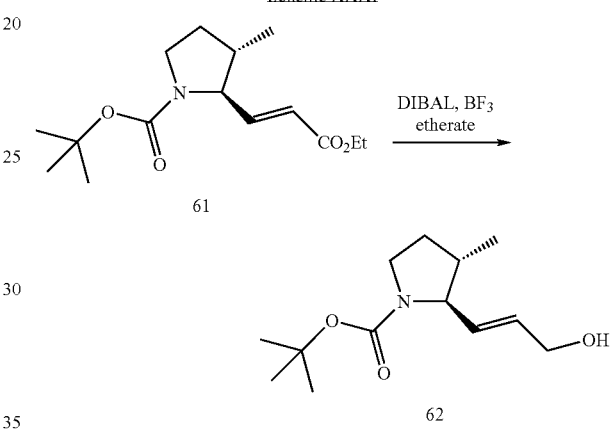

2-(3-hydroxy-propenyl)-3-methyl-pyrrolidine-1-carboxylic acid tert-butyl ester (62); A solution containing crude 61 (16.7 g, 0.059 mol) in DCM (150 mL) was cooled to −78° C. BF$_3$.Et$_2$O (8.9 mL, 0.07 mol) was added followed by the dropwise addition of DIBAL (2 M/DCM, 200 mL, 0.4 mol). After 2 h, TLC analysis indicated complete consumption of the 61 [TLC analysis: 1:1 hexane/EtOAc, R$_f$(62)=0.3]. EtOAc (40 mL) was added and the reaction mixture was warmed to −15° C. The reaction mixture was carefully quenched with 1M HCl until pH=2. The product was extracted with DCM. The organic extracts were washed with 1M HCl, water, and brine, dried over anhydrous Na$_2$SO$_4$, filtered, and concentrated. The crude 62 was purified by silica gel chromatography (2:1 hexanes/EtOAc) to afford 7.2 g (51%) of 62. $^1$H NMR (CDCl$_3$, 300 MHz) δ 5.8-5.5 (m, 2H), 4.18 (m, 2H), 4.0-3.25 (m, 3H), 2.2-1.85 (m, 2H), 1.55-1.3 (m. 1H), 1.43 (s, 9H), 1.15 (d, J=6 Hz, 3H) ppm.

Scheme XXXII

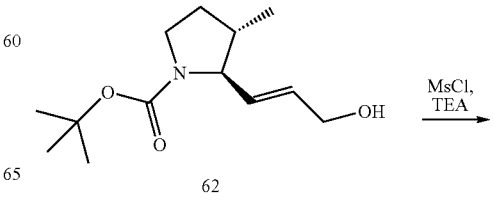

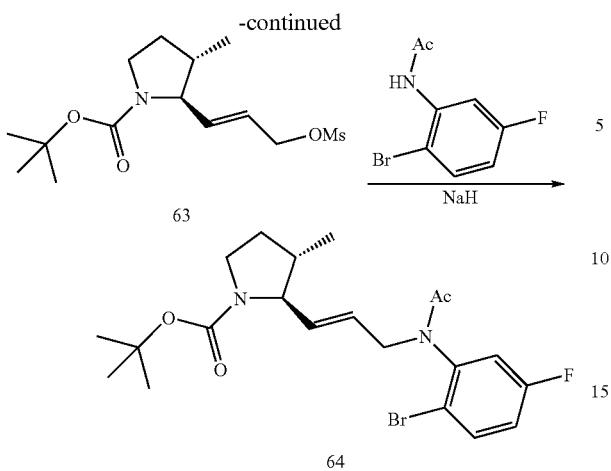

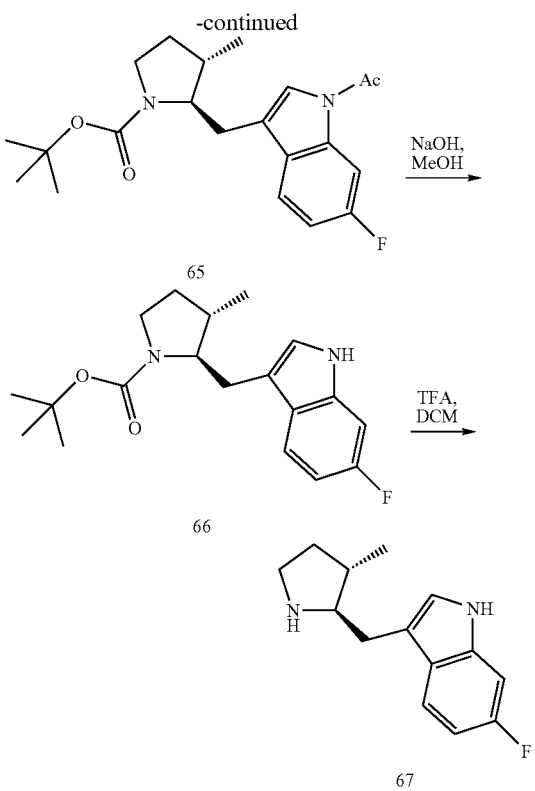

2-(3-Methanesulfonyloxy-propenyl)-3-methylpyrrolidine-1-carboxylic acid tert-butyl ester (63): To a solution containing 62 (6.0 g, 0.025 mol) in DCM (25 mL) at 0° C. was added Et$_3$N (4.5 mL, 0.032 mol). After 5 min, a solution containing methanesulfonylchloride (2.33 mL, 0.03 mol) in DCM (5 mL) was added drop wise. After 2 h, TLC analysis revealed complete consumption of 62 [1:1 hexanes/EtOAc, R$_f$(63)=0.5, R$_f$(62)=0.4]. The reaction mixture was poured onto ice-water and extracted with DCM. The organic extracts were washed with water, brine, and dried over anhydrous Na$_2$SO$_4$, filtered, and concentrated to afford 7.05 g (89%) of crude 63 as a pale brown oil which was used without further purification. $^1$H NMR (CDCl$_3$, 300 MHz) δ5.8-5.5 (m, 2H), 4.69 (d. J=6.15 Hz, 2H), 3.85-3.3 (m, 3H), 3.0 (s, 3H), 2.0-1.9 (m, 1H), 1.55-1.30 (m, 1H), 1.40 (s, 9H), 1.0 (d, J=6.74 Hz, 3H) ppm.

2-{3-[Acetyl-(2-bromo-5-fluoro-phenyl)-amino]-propenyl}-3-methyl-pyrrolidine-1-carboxylic acid (64): To a suspension of NaH (60%, 1.44 g, 0.036 mol) in DMF (15 mL) at 0° C. was added a solution containing 2-bromo-5-fluoroacetanilide (8.35 g, 0.036 mol) in DMF (10 mL). After 30 min, a solution containing crude 63 (9.58 g, 0.03 mol) in DMF (10 ml) was added and the reaction mixture was warmed to ambient temperature overnight. The reaction was quenched by pouring onto the ice-water containing 1M HCl. The product was extracted with diethyl ether, washed with water, brine, dried over anhydrous Na$_2$SO$_4$, filtered, and concentrated. The product was purified by flash silica gel chromatography (2:1 hexane/EtOAc) to afford 5.41 g (45%) of 64 as a pale brown viscous oil. $^1$H NMR (CDCl$_3$, 300 MHz) δ7.62 (m, 1H), 7.05 (m, 2H), 5.65-5.25 (m, 2H), 4.9-4.7 (m, 1H), 4.3-4.1 (m, 1H), 3.85-3.3 (m, 4H), 2-1.9 (m, 1H), 1.8 (s, 3H) 1.55-1.3 (m, 1H), 1.43 (s, 9H), 0.96 (d, J=6.15 Hz, 3H) ppm. Mass spectrum, m/z 354.36 (M-Boc)$^{+}$.

Scheme XXXII

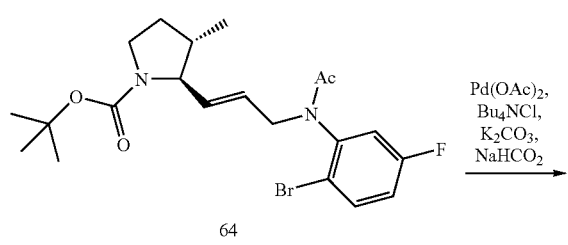

2-(1-Acetyl-6-fluoro-1H-indol-3-ylmethyl)-3-methyl-pyrrolidine-1-carboxylic acid tert-butyl ester (65): A solution containing 64 (5 g, 0.011 mol), n-Bu$_4$NCl (3.3 g, 0.012 mol), K$_2$CO$_3$ (1.65 g, 0.012 mol), and NaHCO$_2$ (0.81 g, 0.012 mol) in DMF (20 mL) was degassed under high vacuum. Palladium acetate (0.49 g, 0.002 mol) was added and the heterogeneous reaction mixture was immersed in a preheated (80-85° C.) oil bath. After 3 h, TLC analysis revealed complete consumption of 64 [1:1 hexane/EtOAc, R$_f$(64)=0.4, R$_f$(65)=0.5]. The reaction mixture was cooled in an ice bath and diethyl ether (100 mL) was added. The mixture was filtered through Celite® and the solids were washed with diethyl ether. The filtrate was washed with water, brine, dried over anhydrous Na$_2$SO$_4$, filtered, and concentrated. The crude product was purified by normal phase HPLC (10-100% EtOAc/hexane over 50 min) to afford 2.2 g (54%) of 65 as brown, viscous oil. $^1$H NMR (CDCl$_3$, 300 MHz) δ8.22-8.1 (m, 1H), 7.7-7.5 (m, 1H), 7.15-6.97 (m, 2H), 3.8-2.65 (m, 4H), 2.6 (s, 3H), 2.12-1.85 (m, 1H), 1.62 (s, 1H), 1.42 (s, 9H, major rotamer), 1.4 (s, minor rotamer), 0.9 (d, J=6 Hz, 3H) ppm. Mass spectrum, m/z=274.5 (M-BOC)$^{+}$.

2-{6-Fluoro-1H-indol-3-ylmethyl)-3-methyl-pyrrolidin-1-carboxylic acid tert-butyl ester (66): To a solution containing 65 (2.2 g, 0.006 mol) in MeOH (15 mL) was added 1M NaOH (6 mL, 0.006 mol) at 0° C. After 30 min, TLC analysis revealed complete consumption of 65 [EtOAc/hexanes 1:1, R$_f$(65) 0.6; R$_f$(66)=0.5]. The solvent was removed in vacuo and the residue was dissolved in EtOAc. The organic phase was washed with 1M HCl, water, brine, dried over anhydrous Na$_2$SO$_4$, filtered, and concentrated to afford 2.11 g (quant.) of crude 66 which was used in the next step without further purification. $^1$H NMR (CDCl$_3$, 300 MHz) δ9.0 (s, 1H, major rotamer), 8.85 (s, minor rotamer), 7.62-7.5 (m, 1H), 7.1-6.72 (m, 3H), 3.8-2.7 (m, 5H), 2.15-1.3 (m, 3H), 1.55 (s, 9H), 0.85 (d, J=7 Hz, 3H) ppm.

6-Fluoro-3-(3-methyl-pyrrolidin-2-ylmethyl)-1H-indole (67): To solution containing 66 (0.89 g, 0.0024 mol) in DCM (20 mL) at 0° C. was added TFA (4 mL). After 2 h, TLC analysis revealed complete consumption of 66 [10% MeOH/DCM, Rf(66)=0.7, $R_f$(67)=0.3]. The reaction mixture was concentrated in vacuo, diluted with DCM, washed with aqueous NaHCO₃, brine, dried over anhydrous Na₂SO₄, filtered, and concentrated to afford 0.6 g (86%) of 67 which was used without further purification. ¹H NMR (CDCl₃, 300 MHz) δ9.0 (br s, 1H), 7.6-7.35 (m, 1H), 7.1-6.7 (m, 3H), 4.2 (br m, 1H), 3.2-2.5 (m, 5H), 2.1-1.2 (m, 3H), 1.05 (d, J=6.74 Hz, 3H) ppm.

Scheme XXXIII

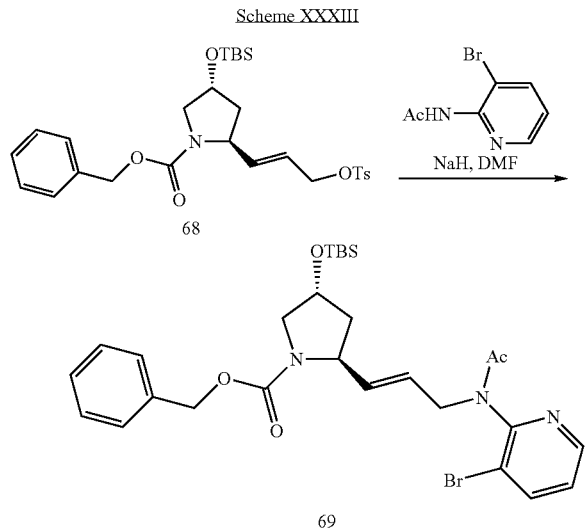

2-{3-[Acetyl-(3-bromo-pyridin-2-yl)-amino]-propenyl}-4-(tert-butyl-dimethyl-silanyloxy)-pyrrolidine-1-carboxylic acid benzyl ester (69): Under a nitrogen atmosphere at 0° C., NaH (0.89 g, 23.0 mmol) was added in portions to a solution containing 2-acetylamino-3-bromopyridine (4.12 g, 19.2 mmol) in DMF (30 mL). After 15 min at 0° C. for and 1 h at ambient temperature the reaction mixture was recooled to 0° C. and a solution containing 68 (8.99 g, 19.2 mmol) in DMF (10 mL) was added dropwise. The reaction mixture was then stirred at ambient temperature for 2 h at which point TLC analysis revealed complete consumption of 68 [1:1 hexanes/EtOAc, $R_f$(68)=0.6; $R_f$(69)=0.3]. The reaction mixture was cooled to 0° C. followed by the dropwise addition of saturated aqueous NH₄Cl. The product was extracted with diethyl ether. The combined ether extracts were washed with water, brine, dried over anhydrous Na₂SO₄, filtered and concentrated. The crude product was purified by flash silica gel chromatography (20% EtOAc/hexanes) to afford 6.0 g (54%) of 69 as an white solid. ¹H NMR (CDCl₃, 300 MHz) δ7.4-7.2 (m, 1H), 5.6-5.4 (m, 2H), 5.0 (s, 2H), 4.4-4.2 (m, 4H), 3.5-3.2 (m, 2H), 1.8 (s, 3H), 1.6 (s, 2H), 0.9 (s, 6H), 0.1 (s, 9H) ppm.

Scheme XXXIV

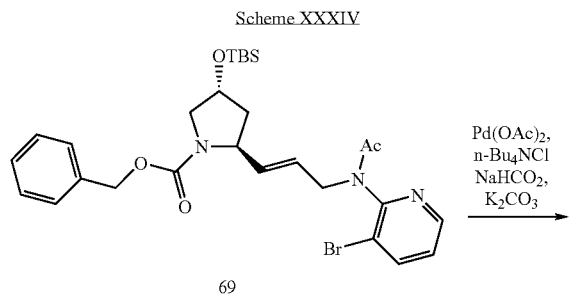

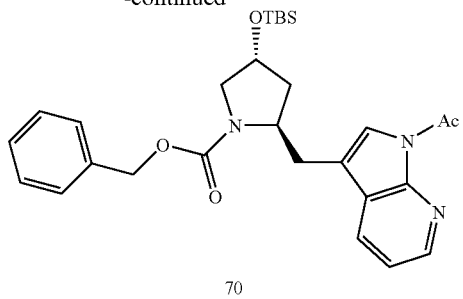

4-Acetoxy-2-(1-acetyl-1H-pyrrolo[2,3-b] pyridine-3-ylmethyl)-pyrrolidine-1-carboxylic acid benzyl ester (70): Under a nitrogen atmosphere a solution containing 69 (5.92 g, 10.1 mmol) in anhydrous DMF (50 mL) was charged with (n-Bu)₄NCl (2.8 g, 10.1 mmol), K₂CO₃ (1.4 g, 10.1 mmol), NaHCO₂ (0.68 g, 10.1 mmol), and Pd(OAc)₂ (0.045 g, 0.20 mmol) at ambient temperature. The heterogeneous mixture was immersed in a pre-heated (85° C.) oil bath. After 3 h, TLC analysis revealed some 69 remained therefore additional catalyst (0.01 g) was added. After an additional 1 h of heating, 69 was completely consumed by TLC analysis [1:1 EtOAc/hexanes, $R_f$(69) 0.3; $R_f$(70)=0.8]. The warm reaction mixture was cooled in an ice bath then diluted with diethyl ether and filtered through a pad of celite. The solids were washed with diethyl ether and the filtrate was washed several times with water to remove excess DMF, then washed once with brine, dried over anhydrous Na₂SO₄, filtered, and concentrated to afford 5.1 g of crude 70 which was purified by flash silica gel chromatography (20% EtOAc/hexanes) to afford 3.0 g (59%) of 70 as a white solid. ¹H NMR (CDCl₃, 300 MHz) δ5.18 (m, 1H), 7.60 (m, 1H), 7.18 (m, 1H), 7.05 (dt, J=2.4, 8.7 Hz, 1H), 4.13 (m, 1H), 3.41 (m, 1H), 3.33 (m, 2H), 3.17 (app dd, J=14.1, 38.1 Hz, 1H), 2.61 (s, 3H), 1.83 (m, 3H), 1.69 (m, 1H), 1.49 (s, 94) ppm.

Scheme XXXV 2-(1-Acetyl-1H-pyrrolo[2,3-b] pyridine-3-ylmethyl)-4-hydroxy-pyrrolidine-1-carboxylic acid benzyl ester (71): To a solution containing 70 (2.99 g, 5.88 mmol) in THF (20 ml) at 0° C. was added a solution of TBAF (1M in THF, 11.8 mL, 11.8 mmol) in a dropwise fashion. After 1.5 h, TLC analysis revealed complete consumption of 70 [1:1 hexanes EtOAc, R$_f$(70)=0.64; R$_f$(71)=0.3]. The solvent was removed in vacuo and the residue was dissolved in EtOAc and washed with water, brine, dried over anhydrous Na$_2$SO$_4$, filtered, and concentrated to afford 2.11 g of crude 71 which was used without further purification.

Scheme XXXVI

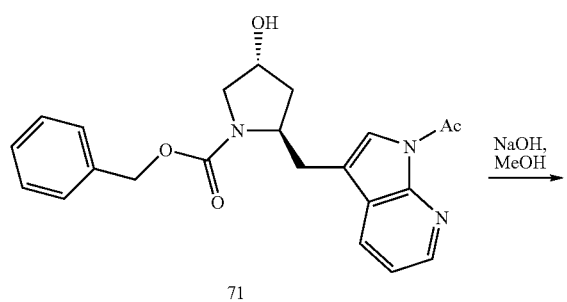

4-Hydroxy-2-(1H-pyrrolo[2,3-b] pyridin-3-ylmethyl)-pyrrolidine-1-carboxylic acid benzyl ester (72): To a solution containing 71 (2.11 g, 5.36 mmol) in MeOH (30 mL) at 0° C. was added 1M NaOH (8.1 mL, 8.05 mmol) in a dropwise fashion. After 1 h, TLC analysis revealed complete consumption of 71 [EtOAc, R$_f$(71)=0.4; R$_f$(72)=0.2]. The MeOH was removed in vacuo and the residue was dissolved in EtOAc, washed with dilute aqueous HCl, water, brine, dried over anhydrous Na$_2$SO$_4$, filtered and concentrated to afford 1.99 g of crude 72 which was used in the next step without further purification.

Scheme XXXVII

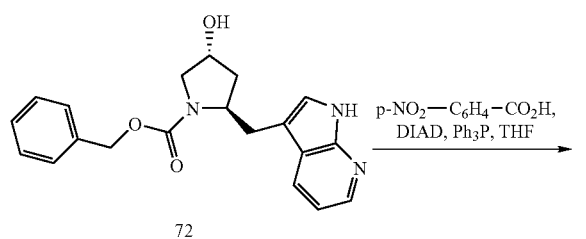

4-(4-Nitro-benzoyloxy)-2-(1H-pyrrolo[2,3-b] pyridine-3-ylmethyl)-pyrrolidine-1-carboxylic acid benzyl ester (73): To a solution containing 72 (1.99 g, 5.66 mmol), p-nitrobenzoic acid (1.23 g, 7.36 mmol), and Ph$_3$P (2.07 g, 7.92 mmol) in THF (35 mL) at 0° C. was added DIAD (1.6 mL, 8.2 mmol). After the addition was complete, the ice bath was removed and the reaction mixture was stirred at ambient temperature for 2 h at which point TLC analysis revealed complete consumption of 72 [EtOAc, R$_f$(72)=0.2; R$_f$(73)=0.6]. The solvent was removed in vacuo and the residue was dissolved in EtOAc, washed with saturated aqueous NaHCO$_3$, brine, dried over anhydrous Na$_2$SO$_4$, filtered, and concentrated to afford 7 g of crude 73 which was purified by flash silica gel chromatography (20% EtOAc/hexanes) to obtained 2.68 g of 73 (95%) as a white solid $^1$H NMR (CDCl$_3$, 300 MHz): δ8.3 (d, J=35 Hz, 2H), 7.6 (d, J=35 Hz, 2H), 7.2 (m, 5H), 7.0 (s, 1H), 5.2 (s, 2H), 4.4-3.2 (m, 3H), 3.0-2.9 (m, 1H), 2.2 (s, 2H), 1.9 (s, 2H) ppm.

Scheme XXXVIII

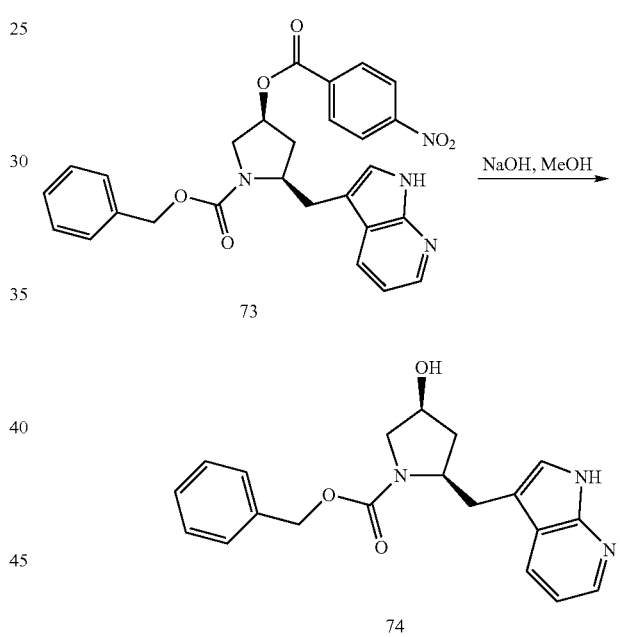

4-Hydroxy-2-(1H-pyrrolo[2,3-b] pyridine-3-ylmethyl)-pyrrolidine-1-carboxylic acid benzyl ester (74) To a solution containing 73 (2.8 g, 5.6 mmol) in a 3:1 mixture of MeOH/DCM (40 mL) at 0° C. was added 1N NaOH (8.5 mL) and the reaction mixture was stirred at ambient temperature for 15 min when TLC analysis revealed complete consumption of 73 [1:1 EtOAc/hexanes; R$_f$(73)=0.3; R$_f$(74)=0.02]. The solvent was removed in vacuo and the residue was dissolved in EtOAc, washed with dilute aqueous HCl, water, brine, dried over anhydrous Na$_2$SO$_4$, filtered, and concentrated to afford 2.7 g of crude 74 which was purified by flash silica gel chromatography (50% EtOAc/hexanes) to obtained 1.6 g of 74 (94%) as a white solid. $^1$H NMR (CDCl$_3$, 300 MHz): δ8.5 (m, 2H), 7.4 (s, 5H), 7.0 (m, 2H), 5.2 (s, 2H), 4.3 (s, 1H), 4.2 (m, 1H), 3.65-3.8 (m, 1H), 3.5-3.3 (m, 2H), 3.2-3.0 (m, 1H), 1.9-2.0 (m, 31-1) ppm.

TABLE 1

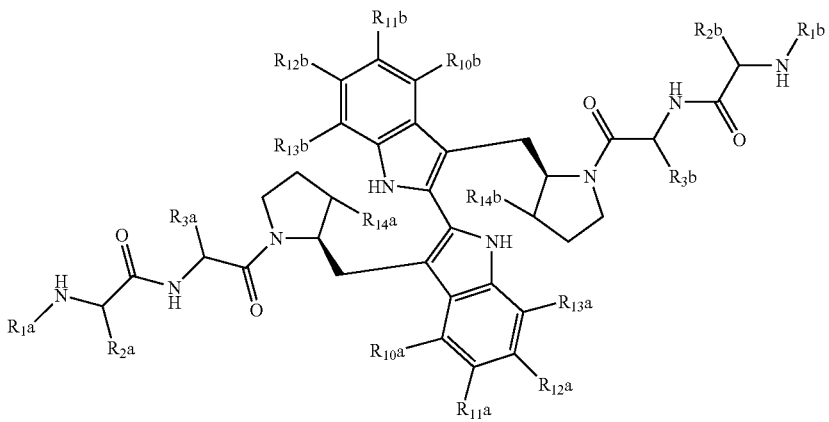

| Compound | R1a | R2a | R3a | R14a | R14b | R3b | R2b | R1b | R11a/R11b | R12a/R12b | R13a/R13b | Kd μM |
|---|---|---|---|---|---|---|---|---|---|---|---|---|
| A | Me | S-Me | S-(2R-MeCHOMe) | S-OH | S-OH | S-(2R-MeCHOMe) | S-Me | Me | H | F | H | A |
| B | Me | S-CH₂OH | S-(2R-MeCHOMe) | S-OH | S-OH | S-(2R-MeCHOMe) | S-CH₂OH | Me | H | F | H | A |
| C | Me | S-Me | S-tBu | S-OH | S-OH | S-tBu | S-Me | Me | H | F | H | A |
| D | Me | S-Et | S-tBu | S-OH | S-OH | S-tBu | S-Et | Me | H | F | H | A |
| E | Et | S-Me | S-(2R-MeCHOMe) | S-OH | S-OH | S-(2R-MeCHOMe) | S-Me | Et | H | F | H | A |
| F | Me | S-Et | S-(2R-MeCHOMe) | S-OH | S-OH | S-(2R-MeCHOMe) | S-Et | Me | H | F | H | A |
| G | Me | S-Me | S-(2R-MeCHOMe) | S-OMe | S-OMe | S-(2R-MeCHOMe) | S-Me | Me | H | F | H | A |
| H | Me | S-Et | S-(2R-MeCHOMe) | S-OMe | S-OMe | S-(2R-MeCHOMe) | S-Et | Me | H | F | H | A |
| I | Me | S-Me | S-tBu | S-OMe | S-OMe | S-tBu | S-Me | Me | H | F | H | A |
| J | Me | S-Et | S-tBu | S-OMe | S-OMe | S-tBu | S-Et | Me | H | F | H | B |
| K | Et | S-Me | S-(2R-MeCHOMe) | S-OMe | S-OMe | S-(2R-MeCHOMe) | S-Me | Et | H | F | H | A |
| L | Et | S-Me | S-tBu | S-OMe | S-OMe | S-tBu | S-Me | Et | H | F | H | A |
| M | Me | S-Me | S-(2R-MeCHOMe) | S-Me | S-Me | S-(2R-MeCHOMe) | S-Me | Me | H | F | H | A |

The binding affinities of the compounds listed in Table I to an IAP were determined substantially as described by Nikolovska-Coleska, Z. et. al. (Analytical Biochemistry (2004), vol. 332:261-273) using a variety of fluorogenic substrates and is reported as a Kd value. Briefly, various concentrations of IAP antagonists were mixed with 5 nM fluorescently labeled peptide (AbuRPF-K(5-Fam)-NH$_2$) and 40 nM of an IAP-BIR3 for 15 min at RT in 100 mL of 0.1M Potassium Phosphate buffer, pH 7.5 containing 100 mg/ml bovine g-globulin. Following incubation, the polarization values (mP) were measured on a Victor 2V using a 485 nm excitation filter and a 520 nm emission filter. IC50 values were determined from the plot using nonlinear least-squares analysis using GraphPad Prism. The compounds described herein afford Kd values in the ranges of: Kd<0.1 μM (A), Kd=0.1-1 μM (B), and Kd 1-10 μM (C). The reported Kd values are the lower of the Kd for XIAP BIR-3 and cIAP-1 BIR-3.

The following compound of the invention was also made and tested. The reported Kd value is the lower of the Kd for XIAP BIR-3 and cIAP-1 BIR-3.

TABLE 4

| Compound | R1a/R1b | R2a/R2b | R3a/R3b | R17a/R17b | R12a/R12b | Kd (μM) |
|---|---|---|---|---|---|---|
| N | Me | Me | R-(Me)CHOMe | (S)-OH | 6-F | B |

In mammalian cells, activation of the caspases is achieved through at least two independent mechanisms which are initiated by distinct caspases, but result in the activation of common executioner (effector) caspases. In addition to the cytochrome c activated mechanism (sometimes referred to as the 'intrinsic death pathway') is a mechanism by which the caspase cascade is activated via activation of a death receptor located on the cell membrane (sometimes referred to as the 'extrinsic death pathway'). Examples of death receptors include CD-95 and TNF-R1 (as well as other members of the TNF group of cytokine receptors). The corresponding ligands are CD-95L and TNF-alpha, respectfully. Binding of pro-caspase-8 to the death receptor induces auto-activation wherein the inhibitory pro-domain of pro-caspase-8 is cleaved and removed. Caspase-8 is released from the receptor and can then activate effector caspases (caspase-3, -6, -7), and, as in the caspase-9 initiated pathway, the result is the proteolytic cleavage of cellular targets by the effector caspases and the induction of apoptosis.

The present invention is directed generally to Smac peptidomimetics and the uses of Smac peptidomimetics. In one embodiment the Smac peptidomimetics act as chemopotentiating agents. The term "chemopotentiating agent" refers to an agent that acts to increase the sensitivity of an organism, tissue, or cell to a chemical compound, or treatment namely "chemotherapeutic agents" or "chemo drugs" or radiation treatment. One embodiment of the invention is the therapeutic composition of a Smac peptidomimetic. A further embodiment of the invention is the therapeutic composition of a Smac peptidomimetic, which can act as a chemopotentiating agent (herein referred to as Smac mimetic), and a biological or chemotherapeutic agent or radiation. Another embodiment of the invention is a method of inhibiting tumor growth in vivo by administering a Smac peptidomimetic. Another embodiment of the invention is a method of inhibiting tumor growth in vivo by administering a Smac mimetic and a biologic or chemotherapeutic agent or chemoradiation. Another embodiment of the invention is a method of treating a patient with a cancer by administering Smac mimetics of the present invention alone or in combination with a chemotherapeutic agent or chemoradiation.

In an embodiment of the present invention, the cells are in situ, in an individual, and the contacting step is effected by administering a pharmaceutical composition comprising a therapeutically effective amount of the Smac mimetic wherein the individual may be subject to concurrent or antecedent radiation or chemotherapy for treatment of a neoproliferative pathology. The pathogenic cells are of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

As described in U.S. Pat. No. 7,244,851, IAP antagonists can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erthematosus or rheumatoid arthritis.

In an embodiment the pathogenic cells are those of any autoimmune disease or diseases which are resistant to apoptosis due to the expression of IAPs or members of the Bcl-2 family. Examples of such autoimmune diseases are collagen diseases such as rheumatoid arthritis, systemic lupus erythematosus, Sharp's syndrome, CREST syndrome (calcinosis, Raytnaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-1 diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome), stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

The subject compositions encompass pharmaceutical compositions comprising a therapeutically effective amount of a Smac mimetic in dosage form and a pharmaceutically acceptable carrier, wherein the Smac mimetic inhibits the activity of an Inhibitor of Apoptosis protein (IAP), thus promoting apoptosis. Another embodiment of the present invention are compositions comprising a therapeutically effective amount of a Smac mimetic in dosage form and a pharmaceutically acceptable carrier, in combination with a chemotherapeutic and/or radiotherapy, wherein the Smac mimetic inhibits the activity of an Inhibitor of Apoptosis protein (IAP), thus promoting apoptosis and enhancing the effectiveness of the chemotherapeutic and/or radiotherapy.

In an embodiment of the invention a therapeutic composition for promoting apoptosis can be a therapeutically effective amount of a Smac peptidomimetic which binds to at least one IAP. In one embodiment the IAP can be XIAP. In another embodiment the IAP can be ML-IAP. In another embodiment the IAP can cIAP-1 or cIAP-2. In a further embodiment the IAP can be multiple IAP types.

Embodiments of the invention also include a method of treating a patient with a condition in need thereof wherein administration of a therapeutically effective amount of a Smac peptidomimetic is delivered to the patient, and the Smac peptidomimetic binds to at least one IAP. In one embodiment the IAP can be XIAP. In another embodiment the IAP can be ML-IAP. In another embodiment the IAP can cIAP-1 or cIAP-2. In a further embodiment the IAP can be multiple IAP types.

The method may further include the concurrent administration of another chemotherapeutic agent. The chemotherapeutic agent can be, but is not limited to, alkylating agents, antimetabolites, anti-tumor antibiotics, taxanes, hormonal agents, monoclonal antibodies, glucocorticoids, mitotic inhibitors, topoisomerase I inhibitors, topoisomerase II inhibitors, immunomodulating agents, cellular growth factors, cytokines, and nonsteroidal antis inflammatory compounds Administration of Smac peptidomimetics The Smac peptidomimetics can be administered in effective amounts. An effective amount is that amount ova preparation that alone, or together with further doses, produces the desired response. This may involve only slowing the progression of the disease temporarily, although preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The administration of the Smac peptidomimetic can occur simultaneous with, subsequent to, or prior to chemotherapy or radiation so long as the chemotherapeutic agent or radiation sensitizes the system to the Smac peptidomimetic.

In general, routine experimentation in clinical trials will determine specific ranges for optimal therapeutic effect for each therapeutic agent and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the Smac peptidomimetic potencies, the duration of the treatment and the severity of the disease being treated. For example, a dosage regimen of the Smac peptidomimetic can be oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

Embodiments of the invention also include a method of treating a patient with cancer by promoting apoptosis wherein administration of a therapeutically effective amount of a Smac peptidomimetic, and the Smac peptidomimetic binds to at least one TAP. In one embodiment the IAP can be XIAP. In another embodiment the IAP can be ML-IAP. In another embodiment the IAP can cIAP-1 or cIAP-2. In a further embodiment the IAP can be multiple IAP types. The method may further include concurrent administration of a chemotherapeutic agent. The chemotherapeutic agent can be, but is not limited to, alkylating agents, antimetabolites, anti-tumor antibiotics, taxanes, hormonal agents, monoclonal antibodies, glucocorticoids, mitotic inhibitors, topoisomerase I inhibitors, topoisomerase II inhibitors, immunomodulating agents, cellular growth factors, cytokines, and nonsteroidal anti-inflammatory compounds.

Routes of administration A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous) intramuscular, or infusion, Intravenous or intramuscular routes are particularly suitable for purposes of the present invention.

In one aspect of the invention, a Smac peptidomimetic as described herein, with or without additional biological or chemotherapeutic agents or radiotherapy, does not adversely affect normal tissues, while sensitizing tumor cells to the additional chemotherapeutic/radiation protocols. While not wishing to be bound by theory, it would appear that because of this tumor specific induced apoptosis, marked and adverse side effects such as inappropriate vasodilation or shock are minimized. Preferably, the composition or method is designed to allow sensitization of the cell or tumor to the chemotherapeutic or radiation therapy by administering at least a portion of the Smac peptidomimetic prior to chemotherapeutic or radiation therapy. The radiation therapy, and/or inclusion of chemotherapeutic agents, may be included as part of the therapeutic regimen to further potentiate the tumor cell killing by the Smac peptidomimetic.

Pharmaceutical compositions In one embodiment of the invention, an additional chemotherapeutic agent (infra) or radiation may be added prior to, along with, or following the Smac peptidomimetic. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The delivery systems of the invention are designed to include time-released, delayed release or sustained release delivery systems such that the delivering of the Smac peptidomimetic occurs prior to, and with sufficient time, to cause sensitization of the site to be treated. A Smac peptidomimetic may be used in conjunction with radiation and/or additional anti-cancer chemical agents (infra). Such systems can avoid repeated administrations of the Smac peptidomimetic compound, increasing convenience to the subject and the physician, and may be particularly suitable for certain compositions of the present invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The pharmaceutical compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous preparation of a chemopotentiating agent (e.g. Smac peptidomimetic), which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. which is incorporated herein in its entirety by reference thereto.

Additional chemotherapeutic agents Chemotherapeutic agents suitable, include but are not limited to the chemotherapeutic agents described in "Modern Pharmacology with Clinical Applications", Sixth Edition, Craig & Stitzel, Chpt. 56, pg 639-656 (2004), herein incorporated by reference. This reference describes chemotherapeutic drugs to include alkylating agents, antimetabolites, anti-tumor antibiotics, plant-derived products such as taxanes, enzymes, hormonal agents such as glucocorticoids, miscellaneous agents such as cisplatin, monoclonal antibodies, immunomodulating agents such as interferons, and cellular growth factors. Other suitable classifications for chemotherapeutic agents include mitotic inhibitors and nonsteroidal anti-estrogenic analogs. Other suitable chemotherapeutic agents include toposiomerase I and II inhibitors and kinase inhibitors.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide acetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also comprise other members, i.e., other than TRAIL, of the TNF superfamily of compounds.

Radiotherapy protocols Additionally, in several method embodiments of the present invention the Smac peptidomimetic therapy may be used in connection with chemo-radiation or other cancer treatment protocols used to inhibit tumor cell growth.

For example, but not limited to, radiation therapy (or radiotherapy) is the medical use of ionizing radiation as part of cancer treatment to control malignant cells is suitable for use in embodiments of the present invention. Although radiotherapy is often used as part of curative therapy, it is occasionally used as a palliative treatment, where cure is not possible and the aim is for symptomatic relief, Radiotherapy is commonly used for the treatment of tumors. It may be used as the primary therapy. It is also common to combine radiotherapy with surgery and/or chemotherapy. The most common tumors treated with radiotherapy are breast cancer., prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation sources external is outside the body, while sealed and unsealed source radiotherapy has radioactive material delivered internally. Brachytherapy sealed sources are usually extracted later, while unsealed sources are injected into the body. Administration of the Smac peptidomimetic may occur prior to, concurrently with the treatment protocol. Annexin V/Propidium Iodide Staining— To show the ability of Smac mimetics to induce apoptosis, Annexin V-fluorescein isothiocyanate staining was performed as per manufacturer's protocol (Invitrogen, Carlsbad, Calif.). Briefly, cells were exposed to various concentrations of Smac mimetics for 18-24 hrs. and then removed from the assay plate by trypsinization. Cells were then pelleted and resuspended in assay buffer (supplied by manufacturer), Annexin V and propidium iodide were added to the cell preparations and incubated for 1 hour in the dark at room temperature. Following the incubation additional buffer (200 µl) was then added to each tube, and the samples were analyzed immediately by flow cytometry. In the presence of Smac mimetics apoptosis was strongly promoted, as assessed by annexin/PI staining and analyzed by flow cytometry. The amplification in the number of apoptotic cells (Annexin V positive/propidium iodide negative—lower right quadrant) by IAP antagonists as compared to control was dose dependent and due to the induction of apoptosis and not via increasing the proportion of necrotic cells.

Biological and chemotherapeutics/anti-neoplastic agents and radiation induce apoptosis by activating the extrinsic or intrinsic apoptotic pathways, and, since Smac mimetics relieve inhibitors of apoptotic proteins (IAPs) and, thus, remove the block in apoptosis, the combination of chemotherapeutics/anti-neoplastic agents and radiation with Smac mimetics should work synergistically to facilitate apoptosis.

The relevance of this potent synergy is that it makes possible the use of the Smac peptidomimetics, which are IAP antagonists, to improve the efficacy of the marketed platinum containing compounds (cisplatin and carboplatin). This may be accomplished by lowering the required dose of the poorly tolerated platinum containing compounds and/or by improving the response rate at the marketed dose.

The present invention is not limited to the embodiments described and exemplified above, hut is capable of variation and modification within the scope of the appended claims.

What is claimed is:
1. A compound of formula (I):

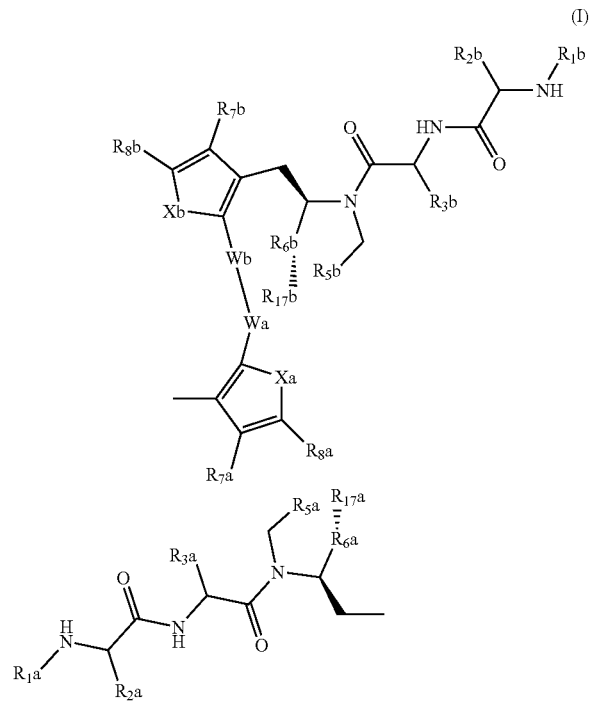

wherein
$R_1a$ and $R_1b$ are independently H or optionally substituted hydroxyl, alkyl, cycloalkyl, heterocycloalkyl, aryl, or heteroaryl;

$R_2a$, and $R_2b$ are independently H or optionally substituted alkyl, cycloalkyl, or heterocycloalkyl;

$R_3a$, and $R_3b$ are independently H or optionally substituted alkyl, cycloalkyl, heterocycloalkyl, aryl, or heteroaryl;

both $R_5a$ and $R_6a$, and $R_5b$ and $R_6b$, are carbon atoms linked by a covalent bond or by an optionally-substituted alkylene or alkenylene group of 1 to 8 carbon atoms where one to three carbon atoms can be replaced by N, O, $S(O)_n$, or C=O;

$R_{17}a$ and $R_{17}b$ are independently —OH, lower alkoxy, or lower alkyl;

$R_7a$, $R_7b$, $R_8a$, $R_8b$ are independently H or optionally substituted hydroxyl, alkyl, cycloalkyl, heterocycloalkyl, aryl, or heteroaryl; or $R_7a$ and $R_8a$, or $R_7b$ and $R_8b$, or both, can be linked by an optionally-substituted alkylene or alkenylene group of 3 to 8 carbon atoms where one to three carbon atoms can be replaced by N, O, $S(O)_n$, or C=O;

each n can be the same or different and is 0, 1, or 2;

Xa is —O—, —N(La—$R_{10}a$)-, —S—, optionally-substituted —C(La—$R_{10}a$)=CH—, —C(O)—O—, —C(O)—N(La—$R_{10}a$)-, —N=C(La—$R_{10}a$)-;

Xb is —O—, —N(Lb-$R_{10}b$)-, —S—, optionally-substituted —C(Lb-$R_{10}b$)=CH—, —C(O)—O—, —C(O)—N(Lb-$R_{10}b$)-, —N=C(Lb-$R_{10}b$)-;

La and Lb are independently a covalent bond or $C_1$—$C_4$ alkylene;

Wa, Wb, $R_{10}a$, and $R_{10}b$ are defined in paragraphs (a) through (c), which follow:

(a) when Wa and Wb together are a Linker, then Xa or Xb are independently —O—, —S—, or —C(O)—O—; $R_{10}a$ and $R_{10}b$, respectively, are absent; or (b) when Wa and Wb together are a Linker; Xa is —N(La—$R_{10}a$)-, —C(La—$R_{10}a$)=CH—, —N=C(La—$R_{10}a$)-, or —C(O)—N(La—$R_{10}a$)- ; Xb is —N(Lb- R$_{10}$b)-, —C(Lb-R$_{10}$b)=CH—, —N=C(Lb-R$_{10}$b)-, or —C(O)—N(Lb-R$_{10}$b)-; R$_{10}$a and R$_{10}$b are independently H or optionally substituted hydroxyl, alkyl, alkenyl, alkynyl, cycloalkyl, heterocycloalkyl, aryl, or heteroaryl; or (c) when Wa and Wb together are a Linker; Xa is —N(La—R$_{10}$a)-, —C(La—R$_{10}$a)=CH—, —N=C(La—R$_{10}$a)-, or —C(O)—N(La—R$_{10}$a)-; Xb is —N(Lb-R$_{10}$b)-, —C(Lb-R$_{10}$b)=CH—, —N=C(Lb-R$_{10}$b)-, or —C(O)—N(Lb-R$_{10}$b)-; R$_{10}$a and R$_{10}$b together are a Linker;

or a pharmaceutically acceptable salt thereof.

2. The compound of claim 1, wherein R$_3$a, R$_4$a, R$_3$b, and R$_4$b are independently H, methyl, ethyl, isopropyl, isobutyl, sec-butyl, tert-butyl, cycloalkyl, heterocycloalkyl, aryl, or heteroaryl, optionally-substituted with hydroxyl, mercapto, sulfonyl, alkylsulfonyl, halogen, pseudohalogen, amino, carboxyl, alkyl, haloalky, pseudohaloalkyl, alkoxy, or alkylthio.

3. The compound of claim 1 wherein R$_2$a and R$_2$b are independently H, methyl, fluoromethyl, difluoromethyl, ethyl, fluoroethyl, hydroxyethyl, or cycloalkyl.

4. The compound of claim 1 wherein R$_1$a and R$_1$b are independently H, methyl, allyl, propargyl, ethyl, hydroxyethyl, cycloalkyl, or cycloalkylmethyl.

5. The compound of claim 1 wherein R$_3$a, and R$_3$b are independently optionally substituted lower alkyl or C$_3$-C$_8$ cycloalkyl wherein the optional substituents are hydroxy or lower alkoxy.

6. The compound of claim 1 wherein Wa and Wb together are a covalent bond or optionally substituted alkylene, cycloalkyl, or aryl, of 2 to 20 carbon atoms where one or more carbon atoms can be replaced with N, O, or S(O)$_n$; and Xa and Xb are independently —O—, —S—, or —C(O)—O—.

7. The compound of claim 1 wherein Wa and Wb together are a covalent bond or optionally substituted alkylene, cycloalkyl, or aryl, of 2 to 20 carbon atoms where one or more carbon atoms can be replaced with N, O, or S(O)$_n$; Xa is —N(La—R$_{10}$a)-, —C(La—R$_{10}$a)=CH—, or —C(O)—N(La—R$_{10}$a)-; Xb is —N(Lb-R$_{10}$b)—, —C(Lb-R$_{10}$b)=CH—, or —C(O)—N(La—R$_{10}$a)-; Xb is —N(Lb-R$_{10}$b)-; —C(Lb-R$_{10}$b)=CH—, or —C(O)—N(Lb-R$_{10}$b)-; R$_{10}$a and R$_{10}$b are independently H or optionally substituted hydroxyl, alkyl, cycloalkyl, heterocycloalkyl, aryl, or heteroaryl.

8. The compound of claim 1 wherein Wa and Wb together are a covalent bond or optionally substituted alkylene, cycloalkyl, or aryl, of 2 to 20 carbon atoms where one or more carbon atoms can be replaced with N, O, or S(O)$_n$; Xa is —N(La—R$_{10}$a)-, —C(La—R$_{10}$a)=CH—, or —C(O)—N(La—R$_{10}$a)-; Xb is —N(Lb-R$_{10}$b)-,—C(Lb-R$_{10}$b)=CH—, or —C(O)—N(Lb-R$_{10}$b)—; R$_{10}$a and R$_{10}$b together are an optionally-substituted alkylene, cycloalkyl, or aryl of 2 to 20 carbon atoms where one or more carbon atoms can be replaced with N, O, or S(O)$_n$.

9. The compound of claim 1 wherein Wa and Wb are not covalently bound, and Wa and Wb are independently H, Cl, Br, F, CN, COOH, or optionally substituted hydroxyl, alkyl, cycloalkyl, heterocycloalkyl, aryl, or heteroaryl; Xa is —N(La—R$_{10}$a)-, —C(La—R$_{10}$a)=CH—, or —C(O)—N(La—R$_{10}$a)-; Xb is —N(Lb-R$_{10}$b)-,—C(Lb-R$_{10}$b)=CH—, or —C(O)—N(Lb-R$_{10}$b)-; R$_{10}$a and R$_{10}$b together are an optionally-substituted alkylene, cycloalkyl, or aryl of 2 to 20 carbon atoms where one or more carbon atoms can be replaced with N, O, or S(O)$_n$.

10. The compound of claim 1 wherein Wa and Wb are not covalently bound, Wa is H, Cl, Br, F, CN, COOH, or optionally substituted hydroxyl, alkyl, cycloalkyl, heterocycloalkyl, aryl, or heteroaryl; Xa is —N(La—R$_{10}$a)-, —C(La—R$_{10}$a)=CH—, or —C(O)—N(La—R$_{10}$a)-; Xb is —O—, —N(Lb-R$_{10}$b)-, —S—, —C(Lb-R$_{10}$b)=CH—, —C(O)—O—, —C(O)—N(Lb-R$_{10}$b)-; and R$_{10}$b is H or optionally-substituted alkyl; and Wb and R$_{10}$a together are a covalent bond or optionally substituted alkylene, cycloalkyl, or aryl, of 2 to 20 carbon atoms where one or more carbon atoms can be replaced with N, O, or S(O)$_n$.

11. The compound of claim 1 wherein Wa and Wb are not covalently bound, Wb is H, Cl, Br, F, CN, COOH, or optionally substituted hydroxyl, alkyl, cycloalkyl, heterocycloalkyl, aryl, or heteroaryl; Xb is —N(Lb-R$_{10}$b)-, —C(Lb-R$_{10}$b)=CH—, or —C(O)—N(Lb-R$_{10}$b)-; Xa is —O—, —N(La—R$_{10}$a)-, —S—, —C(La—R$_{10}$a)=CH—, —C(O)—O—, —C(O)—N(La—R$_{10}$a)-; and R$_{10}$a is H or optionally-substituted alkyl; and Wa and R$_{10}$b together are a covalent bond or optionally substituted alkylene, cycloalkyl, or aryl, of 2 to 20 carbon atoms where one or more carbon atoms can be replaced with N, O, or S(O)$_n$.

12. The compound of claim 1 wherein Z$_1$a and Z$_1$b are both N and Z$_2$a and Z$_2$b are both C and wherein R$_3$a and R$_4$a, and R$_3$b and R$_4$b, are each carbon and are linked by a covalent bond or by an optionally-substituted alkylene or alkenylene group of 1 to 8 carbon atoms where one to three carbon atoms can be replaced by N, O, S(O)$_n$, or C=O.

13. The compound of claim 1 wherein R$_{10}$a and R$_{10}$b are not heterocycloalkyl or heteroaryl.

14. The compound of claim 1 having formula (II):

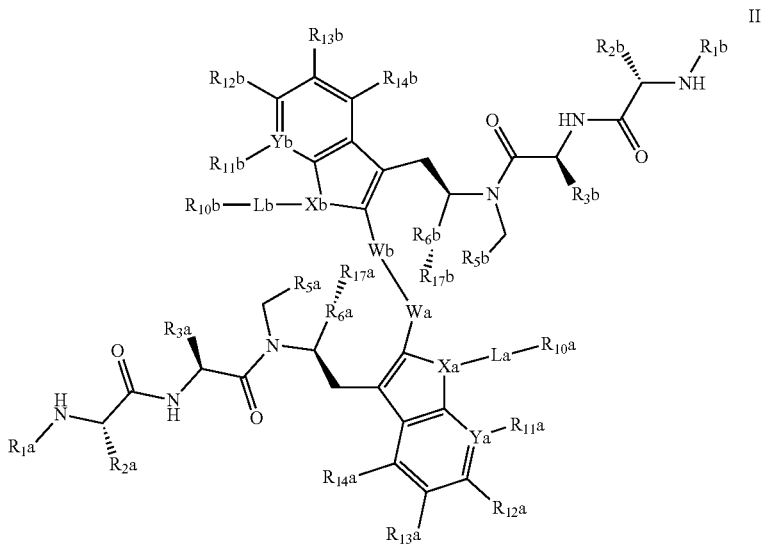

II wherein
Xa is —N—, —C═C($R_{16}$a)-, —N═C— or —C(O)N—;
Xb is —N—, —C═C($R_{16}$b)-, —N═C— or —C(O)N—;
La and Lb are independently a covalent bond or $C_1$-$C_4$ alkylene;
Ya is —C—, —N—, or —N$^+$—; such that,
When Ya is —C— then $R_{10}$a, $R_{11}$a, $R_{12}$a, $R_{13}$a, $R_{14}$a, $R_{15}$a, and $R_{16}$a are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xa is —N— or —C(O)—N—, —$L_1$—$R_{10}$a is bound to the —N— atom; and, when Xa is —C═C($R_{16}$a)- or —N═C—, —$L_1$—$R_{10}$a is bound to the —C═atom; and
When Ya is —N— or —N$^+$—, then R11 a is absent or —O—, and $R_{10}$a, $R_{11a}$, $R_{13}$a, $R_{14}$a, $R_{15}$a, and $R_{16}$a are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, —$L_1$—$R_{10a}$ is bound to the —N—atom; and, when X is —C═C($R_{16}$a)- or —N═C—, —$L_1$—$R_{10}$a is bound to the —C═ atom;
Yb is —C—, —N—, or —N$^+$—; such that,
When Yb is —C— then $R_{10}$b, $R_{11}$b, $R_{12}$b, $R_{13}$b, $R_{14}$b, $R_{15}$b, and $R_{16}$b are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xb is —N— or —C(O)—N—, —$L_1$—$R_{10}$b is bound to the —N— atom; and, when Xb is —C═C($R_{16}$b)- or —N═C—, —$L_1$—$R_{10}$b is bound to the —C═ atom; and
when Yb is —N— or —N$^+$—, then $R_{11}$b is absent or —O—, and $R_{10}$b, $R_{12}$b, $R_{13}$b, $R_{14}$b, $R_{15}$b, and $R_{16}$b are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when Xb is —N— or —C(O)—N—, —$L_1$—$R_{10}$b is bound to the —N— atom; and, when Xb is —C═C($R_{16}$b)- or —N═C—, —$L_1$—$R_{10}$b is bound to the —C═atom.

15. The compound of claim 14 wherein (i) $R_5$a and $R_6$a, and $R_5$b and $R_6$b, are each carbon and are linked by a covalent bond or by an optionally-substituted alkylene or alkenylene group of 1 to 8 carbon atoms where one to three carbon atoms can be replaced by N, O, S(O)$_n$, or C═O.

16. The compound of claim 14 wherein $R_3$a and $R_4$a, and $R_3$b and $R_4$b, are carbon atoms and are linked by a covalent bond or by an optionally-substituted alkylene or alkenylene group of 1 to 3 carbon atoms of which one or more can be replaced by N, O, S(O)$_n$, or C═O.

17. The compound of claim 14 wherein
$R_4$a and $R_3$a or $R_4$b and $R_3$b, or both, are linked by an alkylene or alkenylene group of 1 to 3 atoms;
$R_2$a and $R_2$b are independently selected from methyl, fluoromethyl, difluoromethyl, ethyl, fluoroethyl, and cycloalkyl;
Wa and Wb together are a covalent bond or optionally substituted alkylene, cycloalkyl, or aryl, of 2 to 20 carbon atoms where one or more carbon atoms can be replaced with N, O, or S(O)$_n$; and Xa and Xb are independently —O—, —S—, or —C(O)—; or
Wa and Wb together are a covalent bond or optionally substituted alkylene, cycloalkyl, or aryl, of 2 to 20 carbon atoms where one or more carbon atoms can be replaced with N, O, or S(O)$_n$; Xa is —N(La—$R_{10}$a)-, —C(La—$R_{10}$a)═CH—, or —C(O)—N(La—$R_{10}$a)-; Xb is —N(Lb-$R_{10}$b)-, —C(Lb-$R_{10}$b)═CH—, or —C(O)—N(Lb-$R_{10}$b)-; $R_{10}$a and $R_{10}$b are independently H or optionally substituted hydroxyl, alkyl, cycloalkyl, heterocycloalkyl, aryl, or, heteroaryl.

18. The compound of claim 14 wherein $R_{10}$a and $R_{10}$b are not optionally substituted 5-, 6-, or 7-membered heterocycloalkyl or heteroaryl.

19. The compound of claim 1 having formula (IV), or a pharmaceutically acceptable salt thereof:

IV

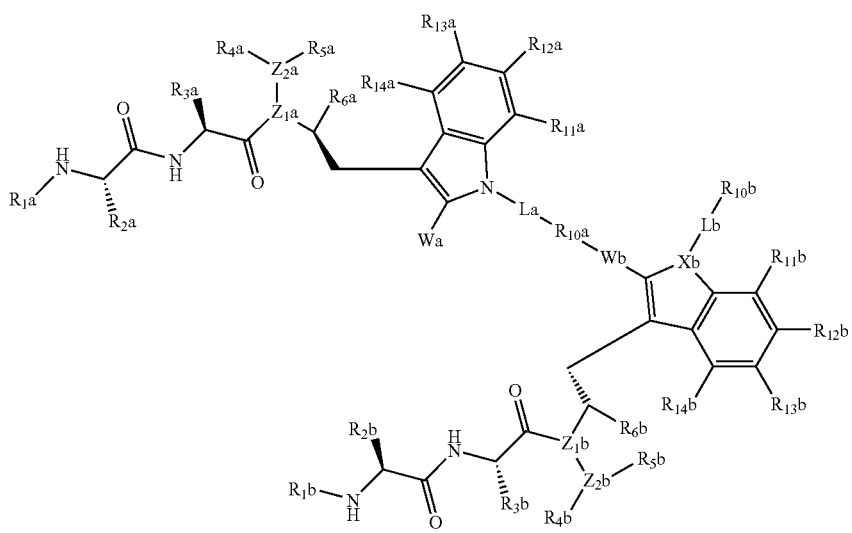

wherein —La—$R_{10}$a-Wb- is a covalent bond.

20. The compound of claim 1 that is selected from compounds A through M, as follows:

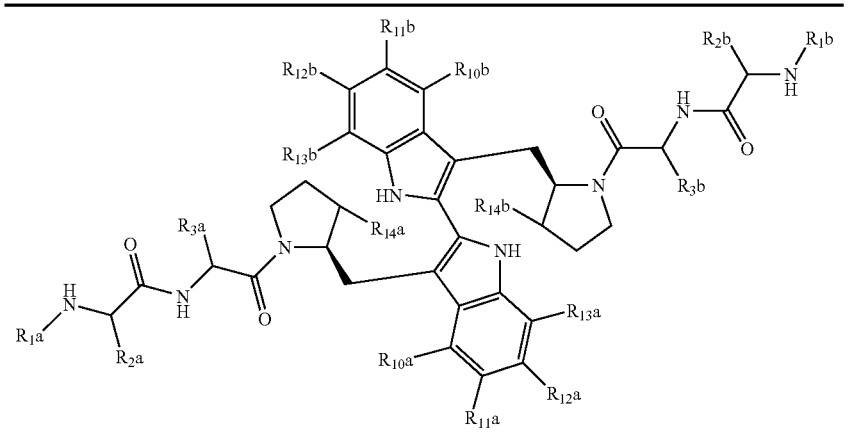

| Compound | R1a | R2a | R3a | R17a | R17b | R3b | R2b | R1b | R13a/R13b | R12a/R12b | R11a/R11b |
|---|---|---|---|---|---|---|---|---|---|---|---|
| A | Me | S-Me | S-(2R-MeCHOMe) | S-OH | S-OH | S-(2R-MeCHOMe) | S-Me | Me | H | F | H |
| B | Me | S-CH$_2$OH | S-(2R-MeCHOMe) | S-OH | S-OH | S-(2R-MeCHOMe) | S-CH$_2$OH | Me | H | F | H |
| C | Me | S-Me | S-tBu | S-OH | S-OH | S-tBu | S-Me | Me | H | F | H |
| D | Me | S-Et | S-tBu | S-OH | S-OH | S-tBu | S-Et | Me | H | F | H |
| E | Et | S-Me | S-(2R-MeCHOMe) | S-OH | S-OH | S-(2R-MeCHOMe) | S-Me | Et | H | F | H |
| F | Me | S-Et | S-(2R-MeCHOMe) | S-OH | S-OH | S-(2R-MeCHOMe) | S-Et | Me | H | F | H |
| G | Me | S-Me | S-(2R-MeCHOMe) | S-OMe | S-OMe | S-(2R-MeCHOMe) | S-Me | Me | H | F | H |
| H | Me | S-Et | S-(2R-MeCHOMe) | S-OMe | S-OMe | S-(2R-MeCHOMe) | S-Et | Me | H | F | H |
| I | Me | S-Me | S-tBu | S-OMe | S-OMe | S-tBu | S-Me | Me | H | F | H |
| J | Me | S-Et | S-tBu | S-OMe | S-OMe | S-tBu | S-Et | Me | H | F | H |
| K | Et | S-Me | S-(2R-MeCHOMe) | S-OMe | S-OMe | S-(2R-MeCHOMe) | S-Me | Et | H | F | H |
| L | Et | S-Me | S-tBu | S-OMe | S-OMe | S-tBu | S-Me | Et | H | F | H |
| M | Me | S-Me | S-(2R-MeCHOMe) | S-Me | S-Me | S-(2R-MeCHOMe) | S-Me | Me | H | F | H |

21. The compound of claim 1 having the formula

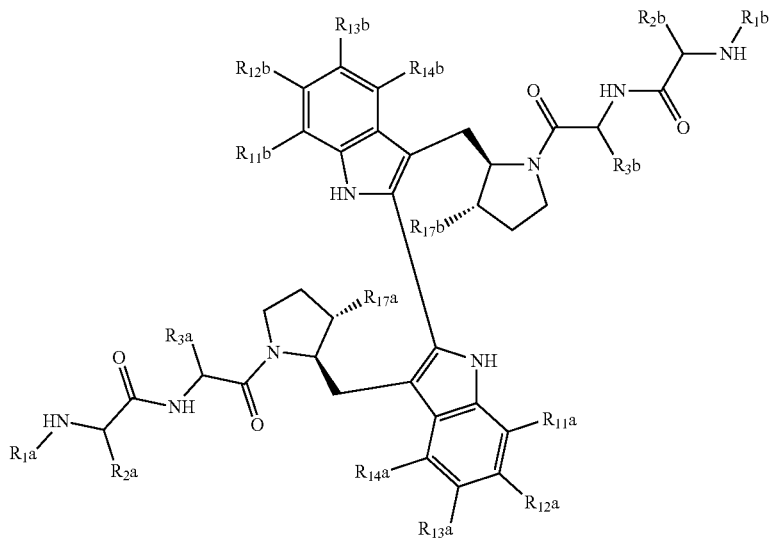

wherein R₁a, R₁b, R₂a, R₂b, R₃a, and R₃b are independently lower alkyl, lower alkoxy, lower alkanol, or C₃-C₆ cycloalkyl; R₁₇a and R₁₇b are independently —OH, lower alkoxy or lower alkyl; R₁₁a, R₁₁b, R₁₂a, R₁₂b, R₁₃a, R₁₃b, R₁₄a, and R₁₄b are independently —H or halogen.

22. A method for inducing apoptosis in a cell comprising contacting the cell with a compound of claim 1 in an amount sufficient to induce apoptosis in the cell.

23. The method of claim 22, wherein said cell is neoplastic.

24. The method of claim 22, wherein said cell overexpresses an inhibitor of caspase.

25. The method of claim 22, wherein the inhibitor inhibits activation or activity of one or more of a caspase selected from caspase-3, caspase-7 and caspase-9.

26. A method of stimulating apoptosis in a cell comprising contacting the cell with a compound of claim 1 in an amount sufficient to stimulate apoptosis in the cell.

27. The method of claim 26, wherein said cells are cancer cells.

28. A method of enhancing apoptosis of pathogenic cells in vivo in an individual comprising administering to the individual a therapeutically effective amount of a compound of claim 1.

29. The method of claim 28 further comprising administering a second therapy selected from radiation, chemotherapy, immunotherapy, photodynamic therapy and combinations thereof.

30. A method of treating a disease associated with the overexpression of IAP in an individual comprising administering to said individual an effective amount of a compound of claim 1.

31. A method of treating cancer comprising administering a therapeutically effective amount of a compound of claim 1.

32. A pharmaceutical composition comprising: a compound selected from a compound of claim 1 and a pharmaceutically acceptable excipient.

33. The composition of claim 32 further comprising a second chemotherapeutic agent.

34. The composition of claim 33, wherein said second chemotherapeutic agent is selected from alkylating agents, plant alkaloids, antitumor antibiotics, antimetabolites, topoisomerase inhibitors and combinations thereof.

35. The composition of claim 34, wherein said chemotherapeutic agent is selected from altretamine, busulfan, carboplatin, carmustine, chlorambucil, cisplatin, cyclophosphomide, dacarbazine, hexamethylmelamine, ifosfamide, lomustine, melphalan, mechlorethamine, oxaliplatin, procarbazine, streptozocin, temozolomide, thiotepa, uramustine, docetaxel, etoposide, irinotecan, paclitaxel, tenisopide, topotecan, vincristine, vinblastine, vindesine, vinorelbine, bleomycin, dactinomycin, daunorubicin, epirubicin, hydroxyurea, idarubicin, mitomycin, mitoxantrone, plicamycin, azathioprine, capecitabine, cladribine, cytarabine, fludarabine, fluorouracil, floxuridine, gemcitabine, mercaptopurine, methotrexate, nelarabine, pemetrexed, pentostatin, thioguanine, camptothecan, irinotecan, topotecan, BNP 1350, SN 38, 9-amino-camptothecan, lurtotecan, gimatecan, diflomotecan, an anthracycline, anthraquinone, podophyllotoxin, doxorubicin, epirubicin, idarubicin, nemorubicin, mitoxantrone, loxoxantrone, etoposide, teniposide and combinations thereof 36. The compound of claim 1 wherein Xa is —N(La—R₁₀a)-, —C(La—R₁₀a)=CH—, —N=C(La—R₁₀a)-, or —C(O)—N(La—R₁₀a)-; Xb is —N(Lb-R₁₀b)-, —C(Lb-R₁₀b)=CH—, —N=C(Lb-R₁₀b)-, or —C(O)—N(Lb-R₁₀b)-; R₁₀a and R₁₀b are independently H or optionally substituted hydroxyl, alkyl, alkenyl, alkynyl, cycloalkyl, heterocycloalkyl, aryl, or heteroaryl.

37. The compound of claim 21 wherein R11a, R11b, R13a, R13b, R18a, and R18b are —H and R12a and R12b are halogen.

38. The compound of claim 37 wherein R1a and R1b are lower alkyl and R2a and R2b are lower alkyl or lower alkanol.

39. The compound of claim 1 having the formula

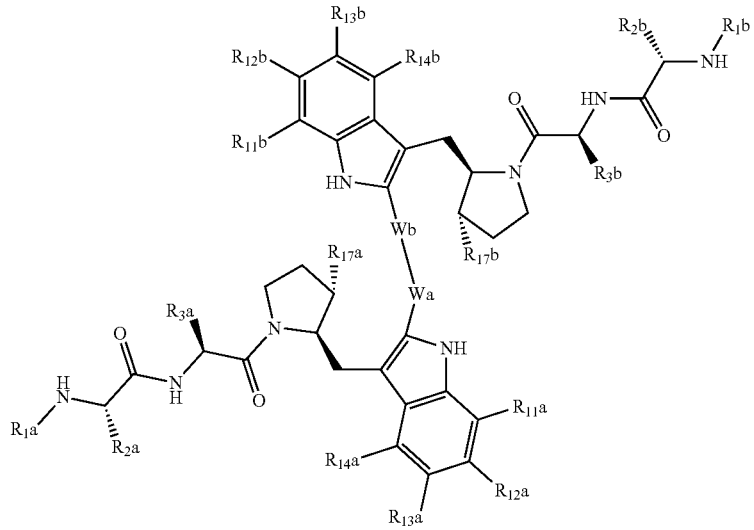

or a pharmaceutically acceptable salt thereof.

40. The compound of claim 39 or a pharmaceutically acceptable salt thereof wherein R₁a and R₁b are independently H, methyl, allyl, propargyl, ethyl, hydroxyethyl, cycloalkyl, or cycloalkylmethyl;

R₂a and R₂b are independently H, methyl, fluoromethyl, difluoromethyl, ethyl, fluoroethyl, hydroxyethyl, or cycloalkyl;

$R_3a$, and $R_3b$ are independently optionally substituted lower alkyl or $C_3$-$C_8$ cycloalkyl wherein the optional substituents are hydroxy or lower alkoxy;

Wa and Wb together are a covalent bond or optionally substituted alkylene, cycloalkyl, or aryl, of 2 to 20 carbon atoms where one or more carbon atoms can be replaced with N, O, or $S(O)_n$;

$R_{17}a$ and $R_{17}b$ are independently —OH, lower alkoxy or lower alkyl; and $R_{11}a$, $R_{11}b$, $R_{12}a$, $R_{12}b$, $R_{13}a$, $R_{13}b$, $R_{14}a$, and $R_{14}b$ are independently H or halogen.

* * * * *

UNITED STATES PATENT AND TRADEMARK OFFICE
CERTIFICATE OF CORRECTION

PATENT NO. : 7,985,735 B2
APPLICATION NO. : 11/782360
DATED : July 26, 2011
INVENTOR(S) : Stephen M. Condon et al.

Page 1 of 1

It is certified that error appears in the above-identified patent and that said Letters Patent is hereby corrected as shown below:

Column 62, Claim 1, Figure 1:
Please replace the current figure with the following:

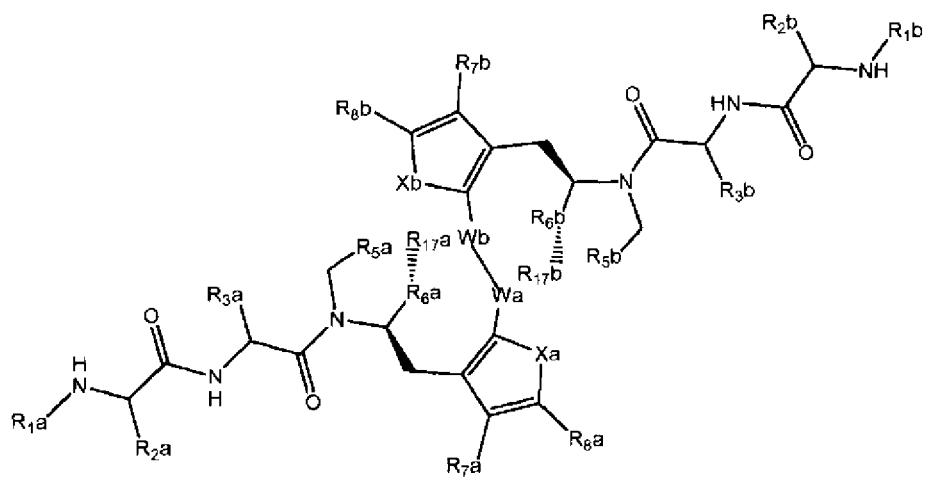

Column 63, Claim 7, Lines 39-40:
Please delete "Xb is –N(Lb-$R_{10}$b)–; C(Lb-$R_{10}$b)=CH–, or –C(O)–N(La–$R_{10}$a)–".

Column 66, Claim 17, Line 28:
Please delete "-C(O)-;" and insert -- -C(O)-O-; --.

Column 67, Claim 20, Chart:
Please delete "R17a R17b" and insert -- R14a R14b --.

Signed and Sealed this
Twenty-fifth Day of September, 2012

David J. Kappos
*Director of the United States Patent and Trademark Office*